US005798228A

United States Patent [19]

Himmler et al.

[11] Patent Number: 5,798,228
[45] Date of Patent: Aug. 25, 1998

[54] RECOMBINANT PRODUCTION OF DOG AND HORSE TYPE I INTERFERONS

[75] Inventors: Adolf Himmler, Vienna; Rudolf Hauptmann, Ebreichsdorf, both of Austria; Norbert Hauel, Schemmerhofen, Germany; Günther Adolf; Peter Swetly, both of Vienna, Austria

[73] Assignee: Boehringer Ingelheim International GmbH, Ingelheim am Rhein, Germany

[21] Appl. No.: 805,165

[22] Filed: Feb. 24, 1997

Related U.S. Application Data

[62] Division of Ser. No. 302,391, Sep. 8, 1994, Pat. No. 5,605,688, which is a continuation of Ser. No. 851,691, Mar. 13, 1992, abandoned, which is a division of Ser. No. 5,300, Dec. 17, 1986, abandoned, which is a continuation of Ser. No. 810,377, Dec. 18, 1985, abandoned.

[30] Foreign Application Priority Data

| Dec. 18, 1984 | [DE] | Germany | 34 46 122.1 |
| Dec. 18, 1984 | [DE] | Germany | 34 46 124.8 |
| Aug. 16, 1985 | [DE] | Germany | 35 29 262.8 |
| Oct. 2, 1985 | [DE] | Germany | 35 35 115.2 |
| Dec. 17, 1985 | [DE] | Germany | 35 44 520.3 |

[51] Int. Cl.$^6$ .................... C12N 15/21; C12N 15/20; C07K 14/56; C07K 14/555

[52] U.S. Cl. .................... 435/69.51; 536/23.52; 435/320.1; 435/325; 435/252.3; 435/252.31; 435/252.33; 435/254.11; 435/254.21

[58] Field of Search .................... 536/23.52; 435/69.51, 435/320.1, 325, 252.3, 252.31, 252.33, 254.4, 254.21

[56] References Cited

U.S. PATENT DOCUMENTS

| 4,262,090 | 4/1981 | Colby, Jr. et al. | 435/91.33 |
| 4,606,917 | 8/1986 | Eppstein | 424/85.6 |
| 4,656,131 | 4/1987 | Kitano et al. | 435/69.51 |
| 4,689,224 | 8/1987 | Bull et al. | 424/233.1 |
| 5,605,688 | 2/1997 | Himmler et al. | 424/85.4 |

FOREIGN PATENT DOCUMENTS

| B-22832/83 | 6/1984 | Australia . |
| 0 036 776 | 9/1981 | European Pat. Off. . |
| 0 042 246 | 12/1981 | European Pat. Off. . |
| 0 080 848 | 6/1983 | European Pat. Off. . |
| 0 088 622 | 9/1983 | European Pat. Off. . |
| 0 093 619 | 11/1983 | European Pat. Off. . |
| 0 115 613 | 8/1984 | European Pat. Off. . |
| WO 80/02375 | 11/1980 | WIPO . |

OTHER PUBLICATIONS

Beltz, G.A. et al., "Isolation of Multigene Families and Determination of Homologies by Filter Hybridization Methods," *Meth. Enzymol.* 100:266–285 (Jun. 1983).
Bishop, J.O., "DNA-RNA Hybridization," *Acta endocrinologica* 168:247–276 (1972).
Blin, N. and D.W. Stafford, "A general method for isolation of high molecular weight DNA from eukaryotes," *Nucl. Ac. Res.* 3(9):2303–2308 (1976).
Capon, D.J. et al., "Two Distinct Families of Human and Bovine Interferon–α Genes Are Coordinately Expressed and Encode Functional Polypeptides," *Mol. Cell. Biol.* 5(4):768–779 (1985).
Dijkema, R. et al., "Structure and expression in *Escherichia coli* of a cloned rat interferon–α gene," *Nucl. Ac. Res.* 12(2):1227–1242 (1984).
Dworkin-Rastl, E. et al., "Molecular Cloning of Human Alpha and Beta Interferon Genes from Namalwa Cells," *J. Interfer. Res.* 2(4):575–585 (1982).
Feinstein, S.I. et al., "Family of Human α–Interferon–Like Sequences," *Mol. Cell. Biol.* 5(3):510–517 (1985).
Gillespie, D., "The Formation and Detection of DNA-RNA Hybrids," *Meth. Enzymol.* 12(B):641–668 (1968).
Goeddel, D.V. et al., "Human leukocyte interferon produced by *E. coli* is biologically active," *Nature* 287(5781):411–416 (1980).
Goeddel, D.V. et al., "The structure of eight distinct cloned human leukocyte interferon cDNAs," *Nature* 290(5):20–26 (1981).
Grunstein, M. and J. Wallis, "Colony Hybridization," *Meth. Enzymol.* 68:379–389 (1979).
Hauptmann, R. and P. Swetly, "A novel class of human type I interferons," *Nucl. Ac. Res.* 13(13):4739–4749 (1985).
Henco, K. et al., "Structural Relationship of Human Interferon Alpha Genes and Pseudogenes," *J. Mol. Biol.* 185(2):227–260 (1985).
Higashi, Y. et al., "Structure and Expression of a Cloned cDNA for Mouse Interferon–β," *J. Biol. Chem.* 258(15):9522–9529 (Aug. 1983).
Himmler, A. et al., "Molecular Cloning and Expression in *Escherichia coli* of Equine Type I Interferons," *DNA* 5(5):345–356 (1986).
Johnson, J.L., "DNA Reassociation and RNA Hybridisation of Bacterial Nucleic Acids," *Meth. Microbiol.* 18:33–74 (1985).
Kafatos, F.C. et al., "Determination of nucleic acid sequence homologies and relative concentrations by a dot hybridization procedure," *Nuc. Ac. Res.* 7(6):1541–1552 (1979).
Lawn, R.M. et al., "DNA sequence of a major human leukocyte interferon gene," *Proc. Natl. Acad. Sci.* 78(9):5435–5439 (1981).
Leung, D.W. et al., "The Structure and Bacterial Expression of Three Distinct Bovine Interferon–β Genes," *Bio/Tech.* 25:458–464 (May 1984).
Ley, K.D. et al., "Equine Interferon: Characterization of a Viral Inhibitor Induced in Equine Kidney Cell Culture with Statolon," *J. Infect. Dis.* 121(3):335–338 (1970).

(List continued on next page.)

*Primary Examiner*—David L. Fitzgerald
*Attorney, Agent, or Firm*—Sterne, Kessler, Goldstein & Fox, PLLC

[57] ABSTRACT

This invention relates to a process for preparing recombinant horse and dog interferons and the interferons themselves.

31 Claims, 74 Drawing Sheets

OTHER PUBLICATIONS

Ohmann, H.B. et al., "Effect of Recombinant DNA-produced Bovine Interferon Alpha (BoIFN-$\alpha_1$) on the Interaction between Bovine Alveolar Macrophages and Bovine Herpesvirus Type 1," *J. Gen. Virol.* 65:1487–1495 (Sep. 1984).

Owen, R.J. and D. Pitcher, "Current Methods for Estimating DNA Base Composition and Levels of DNA-DNA Hybridization," in: *Chem. Meth. Bacter. System.*, Goodfellow, M. and D.E. Minnikin, eds., New York: Academic Press pp.67–93 (1985).

Shaw, G.D. et al., "Structure and expression of cloned murine IFN-$\alpha$ genes," *Nucl. Ac. Res.* 11(3):555–573 (Feb. 1983).

Skup, D. et al., "Molecular cloning of partial cDNA copies of two distinct mouse IFN-$\beta$ mRNAs," *Nucl. Ac. Res.* 10(10):3069–3084 (1982).

Todokoro, K. et al., "Two non-allelic human interferon alpha genes with identical coding regions," *EMBO J.* 3(8):1809–1812 (Aug. 1984).

Tovey, M.G. et al., "Antiviral Activity of Bovine Interferons on Primate Cells," *J. Gen. Virol.* 36:341–344 (1977).

Tsai, S.C. and M.J. Appel, "Hyporesponsiveness to Dog Interferon Induction in vitro," *J. Gen. Virol.* 64:2007–2012 (Sep. 1983).

Velan, B. et al., "Bovine Interferon $\alpha$ Genes," *J. Biol. Chem.* 260(9):5498–5504 (1985).

Wilson, V. et al., "A Comparison of Vertebrate Interferon Gene Families Detected by Hybridization with Human Interferon DNA," *J. Mol. Biol.* 166:457–475 (Jun. 1983).

Yilma, T. et al., "Preliminary Characterization of Equine Interferons and their Antiviral Activities on Bovine, Ovine, and Human Cells," *J. Interfer. Res.* 2(3):363–370 (1982).

Zwarthoff, E.C. et al., "Organization, structure and expression of murine interferon alpha genes," *Nucl. Ac. Res.* 13(3):791–804 (1985).

Dialog World Patent Index File 351 English Language Abstract for EP 0 115 613.

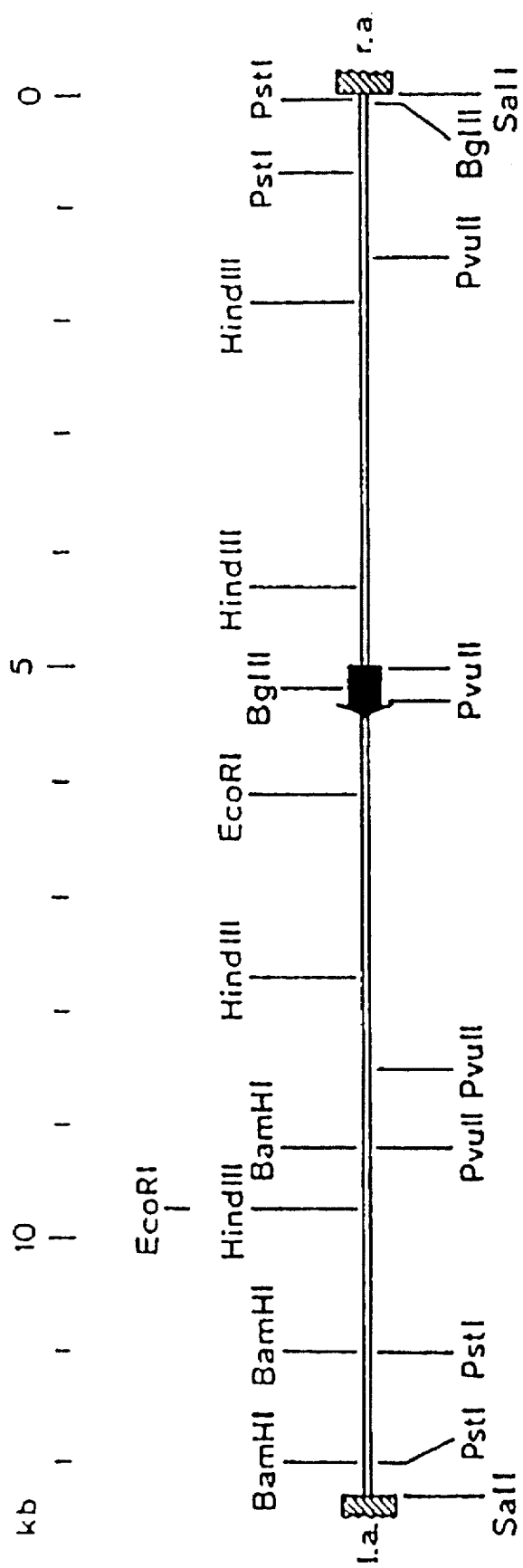

pAH 50

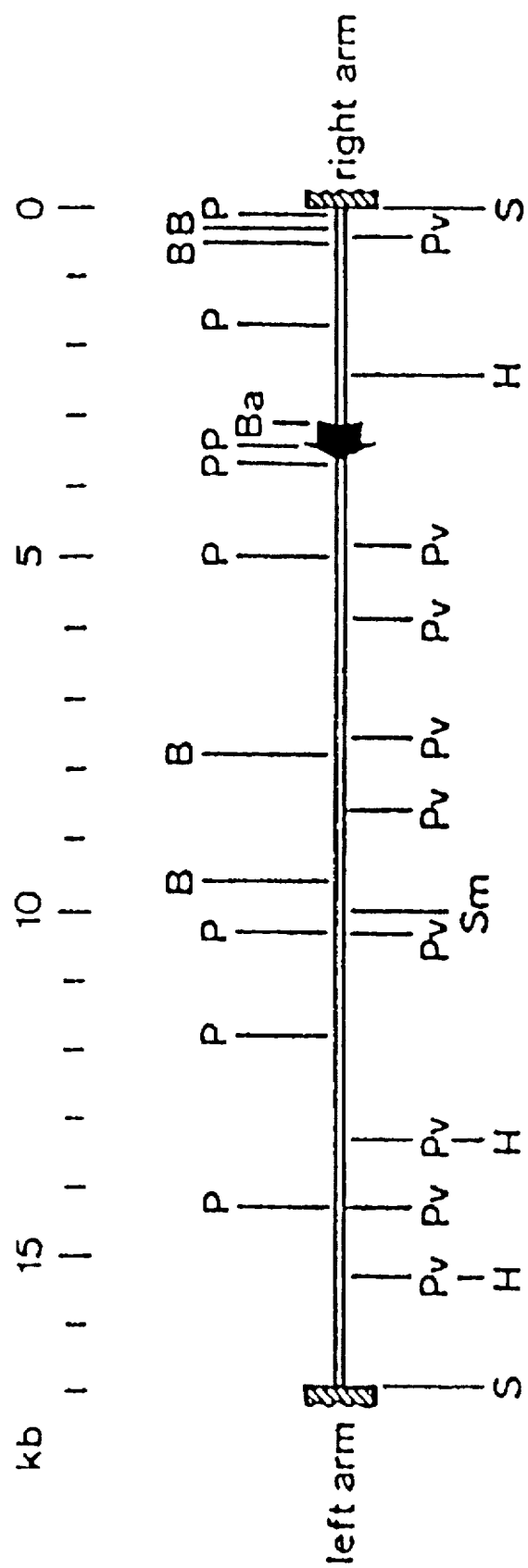

```
                                                                                AAGCTT AAAATTTAGATCATTCTTAAT                                          28
CTTGCAGTGAAGAAAAAGAGTAAAGTTACACTTTCTTTTTCTAAGTATAAAGTAGGCGATAGGCAGGGTGCACATAAACAGATACCGTATCTGTG                                                      127
TTACTAAGTTTTCTGAGGGCTTCAATTAGGAAACATCTAAAAAGAGTCTGGCAGGAGGCAATAACAACGACAAAATATGGTCAAGAAACAC                                                         226
TGCCCTACAACCACCACATCAACTCTACTTCATATAGAAAGCACATAAAGAAACTAAGAAACATAAAAACATGCAGAAAATGGAAACT                                                            325
AGTTCCCTATTTAAGACACATGCACAAAGGAAGGTCTTCAGAGAACCCAGGACCAAGGTCACCACCAGCACCATCTGCAAGATCCCCA                                                             424

-20                           -15                            -10                           -5                       -1  1
                    Met Ala Leu Pro Val Ser Leu Leu Met Ala Leu Val Val Leu Ser Cys His Ser Ile Cys Ser Leu Gly Cys Asp
                    ATG GCT CTG CCT GTT TCC CTA CTG ATG GCC CTG GTG GTG CTC AGC TGC CAC TCC ATC TGC TCT CTG GGA TGT GAC       499

5                             10                            15                            20                        25
Leu Pro His Thr His Ser Leu Pro Gly Asn Thr Arg Val Leu Met Leu Gly Gln Met Arg Ile Ser Pro Phe
CTG CCT CAC ACC CAT AGC CTG CCT GGC AAC ACA AGG GTC TTG ATG CTC GGG CAA ATG AGG ATA TCC CCC TTC                                                       574

30                            35                            40                            45
Ser Cys Leu Lys Asp Arg Asn Asp Phe Gly Gln Glu Val Phe Pro Gln Ile Gln Asn Gln Phe Arg Lys Pro Gln
TCC TGC CTG AAG GAC AGA AAT GAC TTT GGA CAG GAG GTG TTT CCC CAG ATC CAA AAC CAG TTC CGG AAG CCT CAA                                                   649

55                            60                            65                            70                            75
Ala Ile Ser Ala Val His Glu Thr Ile Gln Thr Asp Phe His Leu Phe Ser Thr Asp Gly Ser Ser Ala Ala Trp
GCC ATC TCT GCG GTC CAT GAG ACC ATC CAA ACG GAC TTC CAC CTC TTC AGC ACA GAC GGC TCG TCT GCC GCC TGG                                                   724

80                            85                            90                            95                            100
Asp Glu Ser Leu Leu Asp Lys Leu Tyr Thr Gly Leu Tyr Gln Gln Leu Thr Glu Leu Glu Ala Cys Leu Ser Gln
GAC GAG AGC CTC CTA GAC AAA CTC TAC ACT GGA CTC TAT CAG CAG CTG ACT GAG CTG GAA GCC TGT CTG AGC CAG                                                   799
```

FIG.4A

```
                              105                 110                 115                 120                 125
Glu Val Gly Val Glu Glu Thr Pro Leu Met Asn Glu Asp Ser Leu Ala Val Arg Arg Tyr Phe Gln Arg Ile
GAG GTG GGG GTG GAA GAG ACG CCC CTG ATG AAC GAG GAC TCC CTG GCT GTC AGG AGA TAC TTC CAA AGA ATC       874

130                 135                 140                 145                 150
Ala Leu Tyr Leu Gln Glu Lys Lys Tyr Ser Pro Cys Ala Trp Glu Ile Val Arg Ala Glu Ile Met Arg Ser Phe
GCT CTC TAT CTG CAA GAG AAA AAA TAC AGC CCT TGT GCC TGG GAG ATC GTC AGA GCA GAA ATC ATG AGA TCC TTC  949

155                 160
Ser Ser Thr Asn Leu Pro Gln Ser *
TCT TCA ACA AAC TTG CCG CAG AGT TAA GGAGGAAGAAATGACACCTGGTTCAACATGGAAATGCTTCTCATTGACTGATAATATCA    1038
CACTCCACTTGCTCTGCCATCTCAAGGACTCTCATGTCTGCGTAATCATGACCTGAATTGAATCATTTTCAAATGTTTCAGTAGTATTAATGAA     1137
TGTTGGGTCTAACCCTGTGCTATAGTCTGATACAGACGACCATGTTGATCTATTTATTATTACATATTTATTTAATTATTTATGAGATTTA       1236
AATTATTTTGTGCTATAAACATTATGCACCTTTACACTGTTTAATAACAAATGTATGCTTCATATTTATTATTTCTGTGT                  1335
TCATTAAATCTTTACTGTAGAAAATATCTCTATTCAAGTAAAATACACTTCCTCTAAGCCTGGTTGTGTATGTTGACCTCAGGATATGAGGTGAACACAA 1434
CTATTCATTTACCATCATGTCATATTCAAGTTAGAAGTAAAAATAGACTTCCTCTAAGCCTGGTTGTGTATGTTGACCTCAGGATATGAGGTGAACACAA 1533
CAAATACAGTTCCTGCTTCTTTCGATGTTTTTTCTGGGAAGCTAACTAAAAAAACACTAAGATGCTAAATGGAAGTGAACGTCCGCTGGATATTCGAGT  1632
AATTAACACTAATTAATATTAGAATTATCAGTTAGGTTGAATTGAAGTAGGAATGGAAGTGGTCACATGGAAGAACAGACGACAGAATGGTGAGA       1731
TTGCAATTTACAAGGACCTTCAACCTTAAACTGCTTAGAAGACTCAATGCATTCATGAGAAATCAGAAATCATGAAAATGCCCATATGTTAACAGGA   1830
ATGATTCCTAGGACGTCATTGTTAAGGAATTAAACTGCTTAGAAGACTCAATGCATTCATGAAAATGCCCACACGCTGGGAAAGGAGAGCGCATTG    1929
TGACCATGTTAAGGAATTAAACTGCTTAGAAGACTCAATGCATTCATGAAAATGCCCACACGCTGGGAAAGGAGAGCGCATTG                2028
GCGACCTCAGGGAGACTAGTGTGTGCCTTCTGAACAGAGATTTTGAAGGCAGTTGTGTGTGGATTATTTTAATGTTTATTACTTTAATCATGAAATA   2127
AATGGTTTTGACACTTGCTTCTGCCTTCTGGATAGATTTCACGGCCTTGATGTATTGACAAATCATATTAATATGTTTATTACTTTAATCATGAAATA  2226
TTTGAAATACACTTGCTTCTGGATAGATTTCACGGCCTTGATGTATTGACAAATCATATTAATATGTTTATTACTTTAATCATGAAATA          2325
TTAATTACTTACAATGAGACCTAGTGAGACTTAGTTGGTGAACTAATGAGCAGAACCACATTGGAGTGAGTAGCGGAAGGGTGATAAGGTGATAAG     2424
AACAAAATGGAACAGACCTAGTGAGACTTAGTTGGTGAACTAATGAGCAGAACCACATTGGAGTGAGTAGCGGAAGGTGATAAGAGAAGAACTCCATT   2523
```

FIG.4B

```
GTCATTTTCTCACGTGTGGGCTCACTTTATTTCTGTCATCATATTCAGACCTACACATTTATTCTCCTTTTGCCTCAGTGCATCCAAATGCAAGGATAGC      2622
TTTCTAAGAAGCTGAAAGGGGAAGGAAGAAACAAGTGATGTATTGAAAATGATGGAAAATAATAGCACAGGTCTCTTAAGTTTCCATTTTACTTCCCTAT      2721
TTTGGTACTAACCTCAAGATGAAATAGGAGGTAATTCAGAGGAGTCAAAATAGCAGCAGACAACTCTTGCCAAGGAAAATACTCCATTAAAATGAACATACAAAATGAT  2820
AAAACCCTGAAACTAGTAAAGCAAAGATGTAAACACCAAGGCAGTCTCACTGTCCTACATTCTTCACTGTGAGATGGAGAAGAT      2919
GAACCTAGAGCTCTGTGGAAATGTACTGACAAATAATCTAGGGATGATTAATTAAATCTTGAGTAATCTTAACTATGTGTTAACGATAGCATAG      3018
TGAACAAGATATAGACCTTTCTCCTGAGGAGGTTTCTTGCCAAACAGGTCTAATAGATCCATTTTCAAGAAGACAAATCCAGAAGGGTAAGGCAGCCTG      3117
GCTGACATGCAAAACAAGGGCAAAAGAGAGCTCAGGATCAGAGAGGAGAAATTTGTTCTTAGCAGAGAAGAACACTATTTACATAAGTCTAAGTTTAAC      3216
AAAAAAACTTTCCTCATTTGAAAGCTT                                                                       3243
```

| | Eq-α1 | Bo-α1 | Bo-α2 | Bo-α3 | Mu-α1 | Mu-α2 | Ra-α | Hu-αA | Hu-αB | Hu-αC | Hu-αD | Hu-αF | Hu-αG | Hu-αH | Hu-αI | Hu-αJ | Hu-αK |
|---|---|---|---|---|---|---|---|---|---|---|---|---|---|---|---|---|---|
| Bo-α4 | 57 | 54 | 53 | 45 | 51 | 46 | 48 | 54 | 54 | 58 | 55 | 56 | 55 | 58 | 56 | 54 | 54 |
| Hu-αK | 76 | 65 | 64 | 61 | 59 | 57 | 59 | 86 | 81 | 83 | 84 | 83 | 83 | 84 | 81 | 80 | — |
| Hu-αJ | 73 | 61 | 64 | 60 | 60 | 59 | | 80 | 79 | 92 | 78 | 86 | | 84 | 91 | — | |
| Hu-αI | 76 | 63 | 63 | 61 | 61 | 58 | | 81 | 80 | 94 | 80 | 89 | | 84 | — | | |
| Hu-αH | 74 | 64 | 63 | 62 | 59 | 58 | 59 | 83 | 83 | 86 | 81 | 83 | 86 | — | | | |
| Hu-αG | 75 | 63 | 63 | 61 | 62 | 60 | 60 | 85 | 83 | 84 | 86 | 88 | — | | | | |
| Hu-αF | 73 | 61 | 62 | 59 | 59 | 57 | 57 | 82 | 81 | 89 | 83 | — | | | | | |
| Hu-αD | 73 | 64 | 63 | 62 | 62 | 59 | 62 | 83 | 77 | 81 | — | | | | | | |
| Hu-αC | 76 | 63 | 64 | 62 | 60 | 59 | 59 | 81 | 81 | — | | | | | | | |
| Hu-αB | 71 | 62 | 61 | 60 | 61 | 60 | 60 | 81 | — | | | | | | | | |
| Hu-αA | 76 | 61 | 61 | 61 | 61 | 60 | 60 | — | | | | | | | | | |
| Ro-α | 61 | 57 | 58 | 57 | 84 | 80 | — | | | | | | | | | | |
| Mu-α2 | 57 | 54 | 56 | 54 | 87 | — | | | | | | | | | | | |
| Mu-α1 | 59 | 56 | 58 | 55 | — | | | | | | | | | | | | |
| Bo-α3 | 63 | 92 | 91 | — | | | | | | | | | | | | | |
| Bo-α2 | 63 | 94 | — | | | | | | | | | | | | | | |
| Bo-α1 | 63 | — | | | | | | | | | | | | | | | |
| Eq-α1 | — | | | | | | | | | | | | | | | | |

| % AA–HOMOLOGY | EqIFNβ | HuIFNβ | BoIFNβ1 | 2 | 3 | MuIFNβ |
|---|---|---|---|---|---|---|
| EqIFNβ | – | 59 | 50 | 55 | 55 | 44 |
| HuIFNβ | 76 | – | 51 | 55 | 52 | 48 |
| BoIFNβ1 | 81 | 76 | – | 84 | 84 | 35 |
| 2 | 76 | 81 | 95 | – | 88 | 38 |
| 3 | 86 | 76 | 95 | 90 | – | 36 |
| MuIFNβ | 76 | 67 | 62 | 62 | 62 | – |

SIGNAL PEPTIDE / MATURE IFN

FIG. 6

|        | 10 | 20 | 30 | 40 | 50 | 60 | 70 | 80 | 90 |
|--------|----|----|----|----|----|----|----|----|----|
| EqALF1 | CDLPHTHSLG | NTRVLMLLGQ | MRRISPFSCL | KDRNDFGPQ | EVFDGNQFRK | PQAISAVHET | IQQIFHLFST | DGSSAAWDES | LLDKLYTGLY |
| BoALF1 | CHLPHSHSLA | KRRVLTLLRQ | MRRVLTLLRQ | QDRNDFAFPQ | EALGGSQLQK | AQAISVLHEV | TQHTFQLFST | EGSAAVWDES | LLDRLRTALD |
| BoALF2 | CHLPHTHSLP | NRRVLTLLRQ | LRRVSPSSCL | QDRNDFAFPQ | EALGGSQLQK | AQAISVLHEV | TQHTFQLFST | EGSAAVWDQS | LLDKLRAALD |
| BoALF3 | CHLPHTHILA | NRRVLMLLGQ | LRRVSPSSCL | QDRNDFAFPQ | EALGGSQLQK | AQAISVLHEV | TQHTFQLFST | EGSATMWDES | LLDKLRDALD |
| MuALF1 | CDLPQTHNLR | NKRALTLLVQ | MRRLSPLSCL | KDRKDFGPQ | EKVDAQQIKK | AQAIPVLSEL | TQQILNIFTS | KDSSAAWNAT | LLDSFCNDLH |
| MuALF2 | CDLPHTYNLR | NKRALKVLAQ | MRRLPFLSCL | KDRQDFGPL | EKVDNQQIQK | AQAIPVLRDL | TQQTLNLFTS | KASSAAWNAT | LLDSFCNDLH |
| RaALF  | CDLPHTHNLR | NKRVFTLLAQ | MRRLSPVSCL | KDRKYFGFPL | EKVDGQQIQK | AQAIPVLHEL | TQQILSLFTS | KESSTAWDAT | LLDSFCNDLQ |
| HuALFA | CDLPQTHSLG | SRRTLMLLAQ | MRKISLFSCL | KDRHDFGFPQ | EEF-GNQFQK | AETIPVLHEM | IQQIFNLFST | KDSSAAWDET | LLDKFYTELY |
| HuALFB | CDLPQTHSLG | NRRALILLAQ | MRRISPFSCL | KDRHDFEFPQ | EEFDKQFQK | AQAISVLHEM | IQQTFNLFST | KDSSAALDET | LLDEFYIELD |
| HuALFC | CDLPQTHSLG | NRRALILLGQ | MGRISPFSCL | KDRHDFRIPQ | EEFDGNQFQK | AQAISVLHEM | IQQTFNLFST | EDSSAAWEQS | LLEKFSTELY |
| HuALFD | CDLPETHSLD | NRRTLMLLAQ | MSRISPSSCL | MDRHDFGFPQ | EEFDGNQFQK | APAISVLHEL | IQQIFNLFLT | KDSSAAWDED | LLDKFCTELY |
| HuALFF | CDLPQTHSLG | NRRALILLAQ | MGRISPFSCL | KDRHDFGFPQ | EEFDGNQFQK | AQAISVLHEL | IQQIFNLFTT | KDSSATWEQS | LLEKFSTELN |
| HuALFG | CDLPQTHSLS | NRRTLMIMAQ | MGRISPFSCL | KDRHDFGFPQ | EEFDGNQFQK | AQAISVLHEM | IQQTFNLFST | KDSSATWDET | LLDKFYTELY |
| HuALFH | CNLSQTHSLN | NRRTLMLMAQ | MRRISPFSCL | KDRHDFEFPQ | EEFDGNQFQK | AQAISVLHEM | MQQTFNLFST | KNSSAAWDET | LLEKFYIELF |
| HuALFK | CDLPQTHSLG | HRRTMMLLAQ | MRRISLFSCL | KDRHDFRFPQ | EEFDGNQFQK | AEAISVLHEV | IQQTFNLFST | KDSSVAWDER | LLDKLYTELY |
| HuALFL | CDLPQTHTLR | NRRALILLGQ | MGRISPFSCL | KDRHDFRIPQ | EEFDGNQFQK | AQAISVLHEM | IQQTFNLFST | EDSSAAWEQS | LLELFSTELY |
| BoALF4 | CDLSPNHVLV | GRONLRLLGQ | MRRLSPRFCL | QDRKDFAFPQ | EMVEVSQFQE | AQAISVLHEM | LQQSFNLFHK | ERSSAAWDTI | LLEQLLIGLH |

FIG.7A

```
                100        110        120        130        140        150        160        170
EqALF1   QQLTELEACL SQEVGVEETP LMNEDSLLAV RRYFQRIALY LQEKKYSPCA WEIVRAEIMR SFSSSTNLPQ S

BoALF1   QQLTDLQACL RQEEGLPGAP LLKEDSSLAV RKYFHRLTLY LQEKRHSPCA WEVVRAQVMR AFSSSTNLQE RFRRKD
BoALF2   QQLTDLQACL RQEEGLRGAP LLKEDASLAV RKYFHRLTLY LQEKRHSPCA WEVVRAEVMR AFSSSTNLQE KFRRKD
BoALF3   QQLTDLQFCL RQEEELQGAP LLKEDSSLAV RKYFHRLTLY LQEKRHSPCA WEVVRAQVMR AFSSSTNLQE SFRRKD

MuALF1   QQLNDLQGCL MQQVGVQEFP LTQEDALLAV RKYFHRITVY LREKKHSPCA WEVVRAEVWR ALSSSANVLG RLREEK
MuALF2   QQLNDLQTCL MQQVGVQEPP LTQEDALLAV RKYFHRITVY LREKKHSPCA WEVVRAEVWR ALSSSVNLLP RLSEEKE

RaALF    QQLSGLQACL MQQVGVQESP LTQEDSLLAV REYFHRITVY LRENKHSPCA WEVKAEVWR ALSSSANLMG RLREERNES
HuALFA   QQLNDLEACV IQGVGVTETP LMKEDSILAV RKYFQRITLY LKEKKYSPCA WEVVRAEIMR SFSLSTNLQE SLRSKE
HuALFB   QQLNDLEVLC DQEVGVIESP LMYEDSILAV RKYFQRITLY LTEKKYSSCA WEVVRAEIMR SFSLSINLQK RLKSKE
HuALFC   QQLNDLEACV IQEVGVEETP LMNEDSILAV RKYFQRITLY LIERKYSPCA WEVVRAEIMR SLSFSTNLQK RLRRKD
HuALFD   QQLNDLEACV MQEERVGETP LMNVDSILAV KKYFYFQRITLY LTEKKYSPCA WEVVRAEIMR SLSLSTNLQE RLRRKE
HuALFF   QQLNDMEACV IQEVGVEETP LMNVDSILTV KKYFQRITLY LTEKKYSPCA WEVVRAEIMR SFSLSKIFQE RLRRKE
HuALFG   QQLNDLEACM MQEVGVEDTP LMNVDSILTV RKYFQRITLY LTEKKYSPCA WEVVRAEIMR SFSLSANLQE RLRRKE
HuALFH   QQMNDLEACV IQEVGVEETP LMNEDSILAV KKYFQRITLY LMEKKYSPCA WEVVRAEIMR SFSFSTNLQK RLRRKD
HuALFK   QQLNDLEACV MQEVWVGGTP LMNEDSILAV RKYFQRITLY LTEKKYSPCA WEVVRAEIMR SFSSSRNLQE RLRRKE
HuALFL   QQLNDLEACV IQEVGVEETP LMNEDSILAV RKYFQRITLY LIERKYSPCA WEVVRAEIMR SLSFSTNLQK RLRRKD

BoALF4   QQLDDLDACL GLLTGEEDSA LGRTGPTLAM KRYFQGIHVY LQEKGYSDCA WEIVRLEIMR SLSSSTSLQE RLRMMDGDLK SP
```

FIG. 7B

```
                                                                              AAGCTTCATTCCTAGTTTTCAGTTATATATTGTAGATAGTTGAGATTGCCAGATAAAGCAACAAAT            64
GTGGCTGAGAAAGCTATGTGATGTCTTGCTGTCTTGTGTACAAGGTTGGGGCCCTACAAAAAATTTAGATATGCTTAGTTGAAC           143
ATTATTCGATGCTAGATACAAAAAGTAGGTTGTCTTTTTAAATCATAAAATGCATATATATTTATTGTTTGTGATAG                  222
TGTAATTGGGAATTAAATCTAATTCTTATGAAAAGAAAATTCCCATACAAGACCCCTCAAAAACATCTCATAATACT                  301
AAACAAAAAATAAAATTACTTTGCCAAATGACAGTGACACTTTACAAATAGCAGAGTCCTAAATGATTTAGCTTATTTG                380
TTCCTTGGTATTTAACAATACAGTGACACTTTAAGGATACAGAGTTTTAGAGACTTGTATGTTTTCCCTAATATA                    459
CATAAAATAAAATAGGACTTTAAGGATACAGAGTTTTAGAGACTACAAAATAATGACATAGCCCACTCACGAGG                     538
GAGAACTGAAAGTGGGAAATTCCTCGAAATAGAAAGAGTGGAGGACCATCCCGTATAAATAGCCCACTCACGGAGG                   617
AAGGACACATTTAAGCTCAAGCCGTTGCCACCTCCACTGGGCTCCACTGGGAGTAAAGGCAACACTGTTCCTGTCTTCATC              696

-20                                    -15                                    -10                                     -5
         Met Thr Tyr Arg Trp Ile Leu Pro Met Ala Leu Leu Leu Cys Phe Ser Thr Thr Ala Leu
         ATG ACC TAC AGG TGG ATC CTC CCA ATG GCC CTC CTG TGT TTC TCC ACC ACG GCT CTT                756

-1   1                                     5                                     10                                     15
         Ser Val Asn Tyr Asp Leu Leu Arg Ser Gln Leu Arg Ser Ser Asn Ser Ala Cys Leu Met
         TCT GTG AAC TAC TAT GAC CTT CTT CGG TCC CAA CTA AGA AGC AGC AAT TCA GCA TGT CTG ATG         816

20                                     25                                     30                                     35
         Leu Leu Arg Gln Leu Asn Gly Ala Pro Gln Arg Cys Pro Glu Asp Met Asn Phe Gln
         CTC CTC CGG CAG TTG AAT GGA GCC CCT CAA CGT TGC CCC GAG GAC ATG AAC TTC CAG                 876

40                                     45                                     50                                     55
         Val Pro Glu Glu Ile Glu Gln Ala Gln Gln Phe Gln Lys Glu Asp Ala Ala Leu Val Ile
         GTC CCT GAG GAG ATT GAG CAA GCA CAG CAG TTC CAG AAG GAG GAT GCT GCA TTG GTC ATC            936
```

FIG.8A

```
 60              65                  70                  75
Tyr Glu Met Leu Gln His Thr Trp Arg Ile Phe Arg Arg Asn Phe Ala Ser Thr Gly Trp
TAT GAG ATG CTC CAG CAC ACC TGG CGT ATT TTC AGA AGA AAT TTC GCT AGC ACT GGC TGG    996

80              85                  90                  95
Asn Glu Thr Ile Val Lys Asn Leu Leu Val Glu Val His Leu Gln Met Asp Arg Leu Glu
AAT GAG ACC ATC GTT AAG AAC CTC CTT GTG GAA GTC CAT CTG CAG ATG GAC CGT CTG GAG   1056

100             105                 110                 115
Thr Asn Leu Glu Glu Ile Met Glu Glu Glu Ser Ser Thr Trp Gly Asn Thr Thr Ile Leu
ACA AAC CTG GAG GAG ATA ATG GAG GAG GAA AGC TCC ACC TGG GGA AAC ACA ACC ATT CTG   1116

120             125                 130                 135
Arg Leu Lys Lys Tyr Gly Arg Ile Ser Gln Tyr Leu Lys Ala Lys Lys Tyr Ser His
CGC CTG AAG AAA TAC GGA AGG ATC TCG CAG TAC CTG AAG GCC AAG AAG TAC AGC CAC       1176

140             145                 150                 155
Cys Ala Trp Thr Val Gln Ala Glu Met Leu Arg Asn Leu Ala Phe Leu Asn Gly Leu
TGT GCC TGG ACA GTG CAA GCG GAA ATG CTC AGG AAC TTG GCC TTC CTT AAC GGA CTC       1236

160             165
Thr Asp Tyr Leu Gln Asn *
ACA GAT TAC CTC CAA AAC TGA GGATCTCCCAGCCTGACCTGACAGCTAAGGCACTGACAGAAGGACAATGCTGACAGTGACTGCA   1308

GGTGTCTTCCCAGCAGAGCTCTTGACGTGACTAAGGCACTGACAGCTAAGGCACTGATTGGAAAGGACAGTTACAGACTTTACAT         1387
TTTTACTAACTTATGAATTAACTTACTATTTCTATTATTCAACATTTAACCTTGAAAATAAATTTTTTATGAACAA                  1466
AATTCAACACGGCTGTTTTAATTTCAACTTGATTTATAGAATCACCCAGATTAAAAACTGCAAACCACCTGTAAATGT                1545
```

FIG.8B

```
TCTTTGTAAAATGTGCCTGCAAACTAGTATAGTTTCTGGCCCCTGCCTTCAAGGAATTTAAAATCCAAGGAAGCCATGC    1624
GGAATATACAAGATAAGAGGTGAGAAGGGGACCTCAACCCTACAGAGGAGAAATGTGGCTTGAGCCCCATATAAACGG    1703
AATTAAAATGGGAGAGACAGGCAGAGGCTCTGGACTCAGAGGACGGGGCTGCTTCTGCCCTGTCCGCTCTCTG         1782
GCCCCACAGTTAGAATCTGATGGCTCTGCCTCTCCCCCCACCCCTCAGGGTGCCCAGAGGAATATGTCAGCTCTTGCCTTTGCCTTTGCCTGGAGCTCATCCC    1861
TACTATCTGCGAGATGCCTGCCTCTGCCCCAGGATTGTAAAATATTTCTGTGCCCTGCAAGCCT                  1940
AAGCGGGAGAAGTCCCAGGCACTTCTGGGACACTGTAAGTGGCAGTCCCTTTATGGTACTCTTCTGGGACAACGAGC    2019
TGTACAGGTGTCTAAGGGAGCCAGTCCTTCCAGGCACACAAGAGACACAAGAAGAAAGAACTCTGTTTC            2098
ATACCCCTGCCATCGGCCTGGTTTTGCTCCCTATTTTCCAGAGAAGCAAGTCTGCCGGCTTTTCCTGCTCTGC        2177
GTCTCCAGGCCACACTCTCCCCAAAGCCAAGGCCAGTGGCAGAGTTAGGTGCAGATTAGGCCACTAAGGTTCCCAGGCACTACACTGGGAAATTG  2256
CCGGGAAGCATGGGAGACAAGGAAATTCAGGTGGATAGAGAGGGCACTAACGTTCCCAGGCTTACACTGGGAAATTG    2335
GAGATTTCCTAGAGCTCTTTGGCCACCGGATCTCGTGTGCTGAACCCTTGTGAACCCTTGGGAACGTGCATT          2414
ATTATGCCTGTCTTCTTGCCATGAGCAGGGATCCGTCGACCTGCAGCCAAGCTT                            2467
                              └─pUC9
```

FIG. 8C

```
                                                           TCTAAAGACTCTGGA        16
GGCAGGAAGGAATAGTGCAGAAAAATATGGTTGAGAAACATTGCTCTAAATCAATGCAGAAAGTGCATAAAGGAAAGC    95
AAAAACAGAAGTAGAAGGGAAACGTTGAGAAGAAAATGGAAACTTCTGTCTGCCCTATTTAAGACACAGA          174
GGAAGGTCTTCAGAGAACCTTACAGAGGGTCAGGGTCACCCACCTGAGCCAGGCCAGCAGCATCTGCAAGATCCCCA    253

-20                     -15                     -10                  -5
Met Ala Leu Pro Phe Ser Leu Leu Met Ala Leu Val Val Leu Ser Cys His Ser Ser Cys   313
ATG GCT CTA CCC TTT TCC TTA CTG ATG GCC CTG GTG GTC CTC AGC TGC CAC TCC AGC TGC

-1    1                         5                      10                  15
Ser Leu Gly Cys Asp Leu Pro His Thr His Ser Leu Gly Asn Thr Arg Val Leu Met Leu   373
TCT CTG GGA TGT GAC CTG CCT CAC ACC CAT AGC CTG GGC AAC ACA AGG GTC TTG ATG CTC 20                      25                      30                  35
Leu Gly Gln Met Arg Arg Ile Ser Pro Phe Ser Cys Leu Lys Asp Arg Asn Asp Phe Gly   433
CTG GGA CAA ATG AGG AGA ATC TCC CCC TTC TCC TGC CTG AAG GAC AGA AAT GAC TTT GGA 40                      45                      50                  55
Phe Pro Gln Glu Val Phe Asp Gly Asn Gln Phe Arg Lys Pro Gln Ala Ile Ser Ala Val   493
TTC CCC CAG GAG GTG TTT GAC GGT AAC CAG TTC CGG AAG CCT CAA GCC ATC TCC GCG GTC 60                      65                      70                  75
His Glu Thr Ile Gln Gln Ile Phe His Leu Phe Ser Thr Asp Gly Ser Ser Ala Ala Trp   553
CAT GAG ACG ATC CAA CAG ATC TTC CAC CTC TTC AGC ACA GAC GGC TCG TCT GCT GCC TGG
```

FIG.10A

```
                80                      85                      90                      95
Asp Glu Ser Leu Leu Asp Lys Tyr Thr Gly Leu Tyr Gln Gln Leu Thr Glu Leu Glu
GAC GAG AGC CTC CTA GAC AAG TAC ACT GGA CTC TAT CAG CAG CTG ACT GAG CTG GAA    613

100                     105                     110                     115
Ala Cys Leu Ser Gln Glu Val Gly Val Glu Glu Thr Pro Leu Met Asn Glu Asp Ser Leu
GCC TGT CTG AGC CAG GAG GTG GGG GTG GAA GAG ACG CCC CTG ATG AAC GAG GAC TCC CTG    673

120                     125                     130                     135
Leu Ala Val Arg Arg Tyr Phe Gln Arg Ile Ala Leu Tyr Leu Gln Glu Lys Tyr Ser
CTG GCT GTG AGG AGA TAC TTC CAA AGA ATC GCT CTC TAT CTG CAA GAG AAG TAC AGC    733

140                     145                     150                     155
Pro Cys Ala Trp Glu Ile Val Arg Ala Glu Ile Met Arg Cys Phe Ser Ser Thr Asn
CCT TGT GCC TGG GAG ATC GTC AGA GCA GAA ATC ATG AGA TGC TTC TCT TCA ACA AAC    793

160
Leu Gln Gln Ser *
TTG CAG CAG AGT TAA GGAGGAAGAGAAATGACACCTGGTTCAACATGGAAATGCTTCTCACTGACTGATAACATCA    867

CAGTTCCATTGCTCTGCCATGTCAAGGACTCAAGGATTTCTGCTGTAATACTAATCTAA    926
```

FIG. 10B

```
EqIFN-α1                                                                         AAGCTTAAAATTTAGATCATTCTTAATCTTGCAGTGAAGAAAAGA -378
EqIFN-α1 GTAAAGTTACACTTTCTTTTTCTAAGTATAAAGTAGGCATAGGCAGGGTGCACATAAAACAGATATACCGTATATCTGTGTTACTAAGTTTTCTTGAGG -279
                                                     *          **      *        *********
EqIFN-α1 GCTTCAATTAGGAAACATCTAAAAGAGTCTGGCAGCAGGA.GGCAATAACAACGACAAAATATGGTCAAGAAACACTGCCCTACAACCACATCA -181
                                                          **    *          *********
EqIFN-α2                                          TCTAAAA.GACTCTGGAGGCAGGAAGG.AATAGTG...CAGAAAAAATATGGTTGAGAAACATTGC.......... -193

EqIFN-α1 ACATCTACTTCATAT.AGAAAGCACATAAA.GAAACTAAAAACAGAAGTAGAAAGT.AAGGGAAACATGCAGAAAATGGAAACT.....AGTTCCCTATT -89
         ***  ** ****    *****          **       *                 * **                  *******
EqIFN-α2 ...TCTAAATCAATGCAGAAAGTGCATAAAGGAAGAAAACAGAAACAAAACAGAAGTAGAAAGTGAAGGGAAACGTTGAAAATGAAACTTCTGTCTGCCCTATT -97

EqIFN-α1 TAAGACACATGCACAAAGGAGGAAGTCTTCAGAGAACCCAGAGACCAAGGCTCACCCACC..........AGCAGCATCTGCAAGATCCCCA -1
         ***                            *                                    **********
EqIFN-α2 TAAGACACATGCACAGAGGAAGTCTTCAGAGAACCTT.ACACCAGG.TCAGAGG.TCACCCCACCTGAGCCAGGCAGCCAGCATCGCAAGATCCCCA -1
                                                         -15                       -10                       -5                -1  1
         Met Ala Leu Pro Val Ser Leu Leu Met Ala Leu Val Val Leu Val Leu Ser Cys His Ser Ile Cys Ser Leu Gly Cys Asp
EqIFN-α1 ATG GCT CTG CCT GTT TCC TTA CTG ATG GCC CTG GTG GTG CTG GTG CTC AGC TGC CAC TCC ATC TGC TCT CTG GGA TGT GAC 74
                                                                  *                    *
EqIFN-α2 ATG GCT CTG CCT CTA CCC TTT TCC TTA CTG ATG GCT CTC GTG GTG CTG GTG CTC CAC TCC AGC TGC TCT CTG GGA TGT GAC 74
         Met Ala Leu Pro Leu Pro Phe Ser Leu Leu Met Ala Leu Val Val Leu Val Leu His Ser Ser Cys Ser Leu Gly Cys Asp
```

FIG.11A

```
                    5                    10                   15                   20                   25
         Leu Pro His Thr His Ser Leu Gly Asn Thr Arg Val Leu Met Leu Gly Gln Met Arg Arg Ile Ser Pro Phe
EqIFN-α1 CTG CCT CAC ACC CAT AGC CTG GGC AAC ACA AGG GTC CTG ATG CTC CTG GGG CAA ATG AGG AGA ATC TCC CCC TTC  149
EqIFN-α2 CTG CCT CAC ACC CAT AGC CTG GGC AAC ACA AGG GTC TTG ATG CTC CTG GGA CAA ATG AGG AGA ATC TCC CCC TTC  149
         Leu Pro His Thr His Ser Leu Gly Asn Thr Arg Val Leu Met Leu Leu Gly Gln Met Arg Arg Ile Ser Pro Phe
                                        *
                    30                   35                   40                   45                   50
         Ser Cys Leu Lys Asp Arg Asn Asp Phe Gly Phe Pro Gln Glu Val Phe Asp Gly Asn Gln Phe Arg Lys Pro Gln
EqIFN-α1 TCC TGC CTG AAG GAC AGA AAT GAC TTT GGA TTC CCC CAG GAG GTG TTT GAC GGC AAC CAG TTC CGG AAG CCT CAA  224
EqIFN-α2 TCC TGC CTG AAG GAC AGA AGA AAT GAC TTT GAC TTC CCC CAG GAG GTG TTT GAC GGC AAC CAG TTC CGG AAG CCT CAA  224
         Ser Cys Leu Lys Asp Arg Asn Asp Phe Asp Phe Pro Gln Glu Val Phe Asp Gly Asn Gln Phe Arg Lys Pro Gln
                                                        55                   60                   65                   70                   75
         Ala Ile Ser Ala Val His Glu Thr Ile Gln Gln Ile Phe His Leu Phe Ser Thr Asp Gly Ser Ser Ala Ala Trp
EqIFN-α1 GCC ATC TCT GCG GTC CAT GAG ACG ATC CAA CAG ATC TTC CAC CTC TTC AGC ACA GAC GGC TCG TCT GCC GCC TGG  299
EqIFN-α2 GCC ATC TCC GCG GTC CAT GAG ACG ATC CAA CAG ATC TTC CAC CTC TTC AGC ACA GAC GGC TCG TCT GCT GCC TGG  299
         Ala Ile Ser Ala Val His Glu Thr Ile Gln Gln Ile Phe His Leu Phe Ser Thr Asp Gly Ser Ser Ala Ala Trp
                                                           Bgl II                                     *
                    80                   85                   90                   95                   100
         Asp Glu Ser Leu Leu Asp Lys Leu Leu Tyr Gln Leu Thr Gly Leu Glu Leu Thr Glu Ala Cys Leu Ser Gln
EqIFN-α1 GAC GAG AGC CTC CTA GAC AAA CTC CTA CAG CTG ACT GGA CTC GAA CTG ACT GAG GCC TGT CTG AGC CAG  374
EqIFN-α2 GAC GAG AGC CTC TAT GAC AAG CTC CTA ACT GGA CTC GAA CTG ACT GAG GCC TGT CTG AGC CAG  374
         Asp Glu Ser Leu Tyr Asp Lys Leu Tyr Thr Gly Leu Gln Leu Thr Glu Ala Cys Leu Ser Gln
                         *
```

FIG.11B

```
                    105                 110                 115                 120                 125
        Glu Val Gly Val Glu Glu Thr Pro Leu Met Asn Glu Asp Ser Leu Leu Ala Val Arg Arg Tyr Phe Gln Arg Ile
EqIFN-α1 GAG GTG GGG GTG GAA GAG ACG CCC CTG ATG AAC GAG GAC TCC CTG CTG GCT GTG AGG AGA TAC TTC CAA AGA ATC  449

EqIFN-α2 GAG GTG GGG GTG GAA GAG ACG CCC CTG ATG AAC GAG GAC TCC CTG CTG GCT GTG AGG AGA TAC TTC CAA AGA ATC  449
        Glu Val Gly Val Glu Glu Thr Pro Leu Met Asn Glu Asp Ser Leu Leu Ala Val Arg Arg Tyr Phe Gln Arg Ile 130                 135                 140                 145                 150
        Ala Leu Tyr Leu Gln Glu Lys Lys Tyr Ser Pro Cys Ala Trp Glu Ile Val Arg Ala Glu Ile Met Arg Ser Phe
EqIFN-α1 GCT CTC TAT CTG CAA GAG AAG AAA TAC AGC CCT TGC GCC TGG GAG ATC GTC AGA GCA GAA ATC ATG AGA TCC TTC  524
                                                              *
EqIFN-α2 GCT CTC TAT CTC CAA GAG AAG AAA TAC AGC CCT TGT GCC TGT GAG ATC GTC AGA GCA GAA ATG ATG AGA TGC TTC  524
        Ala Leu Tyr Leu Gln Glu Lys Lys Tyr Ser Pro Cys Ala Trp Glu Ile Val Arg Ala Glu Ile Met Arg Cys Phe 155                 160
        Ser Ser Thr Asn Leu Pro Gln Ser *
EqIFN-α1 TCT TCA TCC ACA AAC TTG CCG CAG AGT TAA GGAGGAAGAAATGCTTCTCATTGACTGATAATATCA  613
                              *
EqIFN-α2 TCT TCA TCC ACA AAC TTG CCA CAG AGT TAA GGAGGAAGAAATGCACCTGGTTCAACATGGAAATGCTTCTCATTGACTGATAATATCA  613
        Ser Ser Thr Asn Leu Pro Gln Ser *

EqIFN-α1 CACTTCCACTTGCTCTGCCATCTCAAGGACTCTCATG..TCTGCTGTAATCATGACCTGAATTGAATCAATTTTCAAATGTTTCAGTAGTATTAATG  710
               *                              ******                    *

EqIFN-α2 CAGTTCCA.TTGCTCTGCCATGTCAAGGACTCAAGGATTTCTGCTGTAATACTAA  672
```

FIG.11C

```
EqIFN-α1  AATGTTGGGTCTAACCCTGCTGGACATTAGTCTGATACAGACGACCATGTGTTGATCTATTATTATTATTACATATTATTTAATTATTATTATGAGATT  809
EqIFN-α1  TAAATTATTTTGTGCTATAACATTATGTGCACCTTTACACTGTAGTTAATATAACAAAATGTAGTCTTCATATTTATTATTTCTGT  908
EqIFN-α1  GTTCATTAAATCTTTACTCTGTAGAAAATATCTTCTATTGTTTATTCTTTAAAAGAGAAACACCACACCTGAGTGTGCAAGCTGATTAAAGAATGGATGG  1007
```

FIG.11D

```
GAATTCTCAGCTCGCTGATAAACACTTTATTTCTAATCTCATGCGTTATGTGAACATGAGCATGTGTCCCATGAC      77
AGGGAGTGCTCTGTCTCCAGATGACCAAGCGTTTACTAGCCTTCAGGGAATACCTGACCTCTCACTGACAGAAATCACAG  156
AACAGATTCTCTGATTTAGCAAAACTCACACACAGGCTCAGTAGCAGCCCCTTCAGTTGAATCCTGTCCCTCGTTTGAATCCTGTCCCTCGTCTTTCTTTTCAGAGCCTGCCCACCTC  235
TGGACCTGTGCGGCTACAACAATCACACACAGGCTGGTTTGAATCCTGTCCCTCGTCTTTCTTTTCAGAGCTCTTGCTCCTGACT  314
TGGGTAGTCAGTGACATTTTGTTGTTCCTTTTCGATAAAGAAGATGTCACTTTTACTTGCTTACTTTCATTTTCATTTTACT  393
TTCCAATTCCTTGTGCATTCCTTTTCATAACTGCTTACTTTTACTTCCCTTACATTTTCTCCTGTTTTGCAACAAC  472
CTGAGTCTTGAAAATCATACAGGAAATATTTCAGGACCATTAGGACAACTTTTATAAAGTAAAACAACAAATACAAAGAAGAGG  551
CTCAAGGTGGAAATAGAAATATTTCAGGAGCATTAGGACAACTTTTATAAAGTAAAACAACAAATACAAAGAAGAGG  630
TAAGAATTTAGAATTAGGCAAAATAGCAAAGAAAAAATGGATTGCTTGACCATGCTGCTCAAACACCTGGACACATT  709
GCCTTGGTTGGGACAAAGCAGGCGCCCGAAGCAGCAAGAGCCGGTAAACCATCTGGTATAGCCAAGCTCAACGTTCAAGTATAGCCTAATGATGGGCAA  788
TTGCACTTTACACTTCGTGAGGGCAGGAGTGGAGTTAACCATCTGGTATAGCCAAGCTCAACGTTCAAGTATAGCCTAATGATGGGCAA  867
GTACTAAATATTCAGTAATTTCTCCATTGACAGCAGACAGCAGTCTCTTAAAGTCGTTTTAAACATCATCAGAGAGAAATATCCAGATGACCC  946
GAATAAGGTAAGCTAAGACTCTATGCCTGTAAAGATCAGGCCTTCTAAAGTCGTTTTAAACATCATCAGAGAGAAATATCCAGATGACCC  1025
AAGAAGATTTAGAAAAAGAAGCCTAACAATACAGAAGAGTCGAAAATTCAGAGTGACTTCTAAGCTTTTAATGAATAA  1104
TATCAATAGTTCAAGTTCAAGGTTGGTTTTGCTGAGATGATAAGCATTGTGAGTGACTTCTAAGCTTTTAATGAATAA  1183
ATTTCACTTCAGTTGTAAGAATACAGAAGACCTGGGGAAATTCAGAGAATGAAAACTCTTGTCTGAGTATTTAAGACGGACCTAGA  1262
CAAATGGGAAGTACAAAGACCTGGGGAAATTCAGAGAATGAAAACTCTTGTCTGAGTATTTAAGACGGACCTAGA  1341
CAGAAGATCCTCAGAAGAAGCTAGAACAAAGCTCTCAATCTCCCGTCCTCAACCAGAAGAGCTGCCGTCTTGGCACTTACCA  1420

-20                -15                  -10                     -5
Met Ala Phe Ser Val Ser Ser Leu Met Ala Leu Val Val Ile Ser Ser Ser Pro Val Ser
ATG GCT TTC TCA GTG TCT TCC CTG ATG GCA CTG GTG GTG ATC TCC TCC AGC CCC GTC TCC    1480

-1  1                  5                     10                   15
Ser Met Ser Cys Asp Leu Pro Ala Ser Leu Asp Leu Arg Lys Gln Glu Thr Leu Arg Val
TCC ATG AGC TGC GAC CTG CCT GCG AGC CTT GAC CTG AGA AAG CAG GAG ACC CTC AGA GTT    1540

FIG.12A
```

```
      20              25              30                   35
Leu His Gln Met Glu Thr Ile Ser Pro Pro Ser Cys Leu Lys His Arg Thr Asp Phe Arg
CTG CAC CAG ATG GAG ACA ATC TCT CCT CCT TCC TGT CTG AAG CAC AGG ACA GAC TTC AGG    1600

40              45              50                   55
Phe Pro Gln Glu Gln Leu Asp Gly Arg Gln Phe Pro Gln Ala Gln Ala Thr Ser Val Leu
TTC CCC CAG GAG CAG CTG GAT GGC AGG CAG TTC CCA GAG GCC CAG GCC ACG TCT GTC CTC    1660

60              65              70                   75
Gln Glu Met Leu Gln Gln Ile Val Ser Leu Phe His Thr Glu Arg Ser Ser Ala Ala Trp
CAG GAG ATG CTC CAG CAG ATC GTC AGC CTC TTC CAC ACA GAG CGC TCG TCT GCT GCC TGG    1720

80              85              90                   95
Asn Thr Leu Leu Asp Arg Leu Leu Ala Gly Leu His Gln Gln Leu Glu Asp Leu Leu Asn
AAC ACG ACT CTG CTG GAC CGA CTC CTC GCG GGA CTC CAT CAG CAG CTG GAA GAC CTC AAC    1780

100             105             110                  115
Thr Cys Leu Asp Gln Gln Thr Gly Glu Glu Ser Ala Leu Gly Thr Val Gly Pro Thr
ACC TGC TTG GAT CAG CAG ACA GGA GAG GAA TCC GCC CTG GGA ACT GTG GGC CCT ACA        1840

120             125             130                  135
Leu Ala Val Lys Arg Tyr Phe Arg Arg Ile Arg Leu Tyr Leu Thr Glu Lys Lys Tyr Ser
CTG GCC GTG AAG AGG TAC TTC AGG AGA ATC CGT CTG TAC CTG ACA GAG AAG AAA TAC AGT    1900

140             145             150                  155
Asp Cys Ala Trp Glu Ile Val Arg Val Asp Ile Met Arg Ser Phe Ser Ser Ala Asn
GAC TGT GCC TGG GAG ATT GTC AGA GTG GAC ATC ATG AGA TCC TCT TCA GCA AAC           1960
```

FIG.12B

```
                           160                    165                       170
        Leu Gln Gly Arg Leu Gly Met Lys Asp Gly Asp Leu Gly Ser Pro  *
        CTG CAA GGA AGG TTA GGA ATG AAG GAT GGA GAC CTG GGG TCA CCT TGA AATGATTCTCCTACA  2023

CTACTGGGCCATGGCACCCTTGCACCTGTCTTAGTCATTCAAAAGGCTCTCTTATTCTCTGCTTGGTCATATACTTTAT  2102
        TGAATTC                                                                         2109
```

FIG. 12C

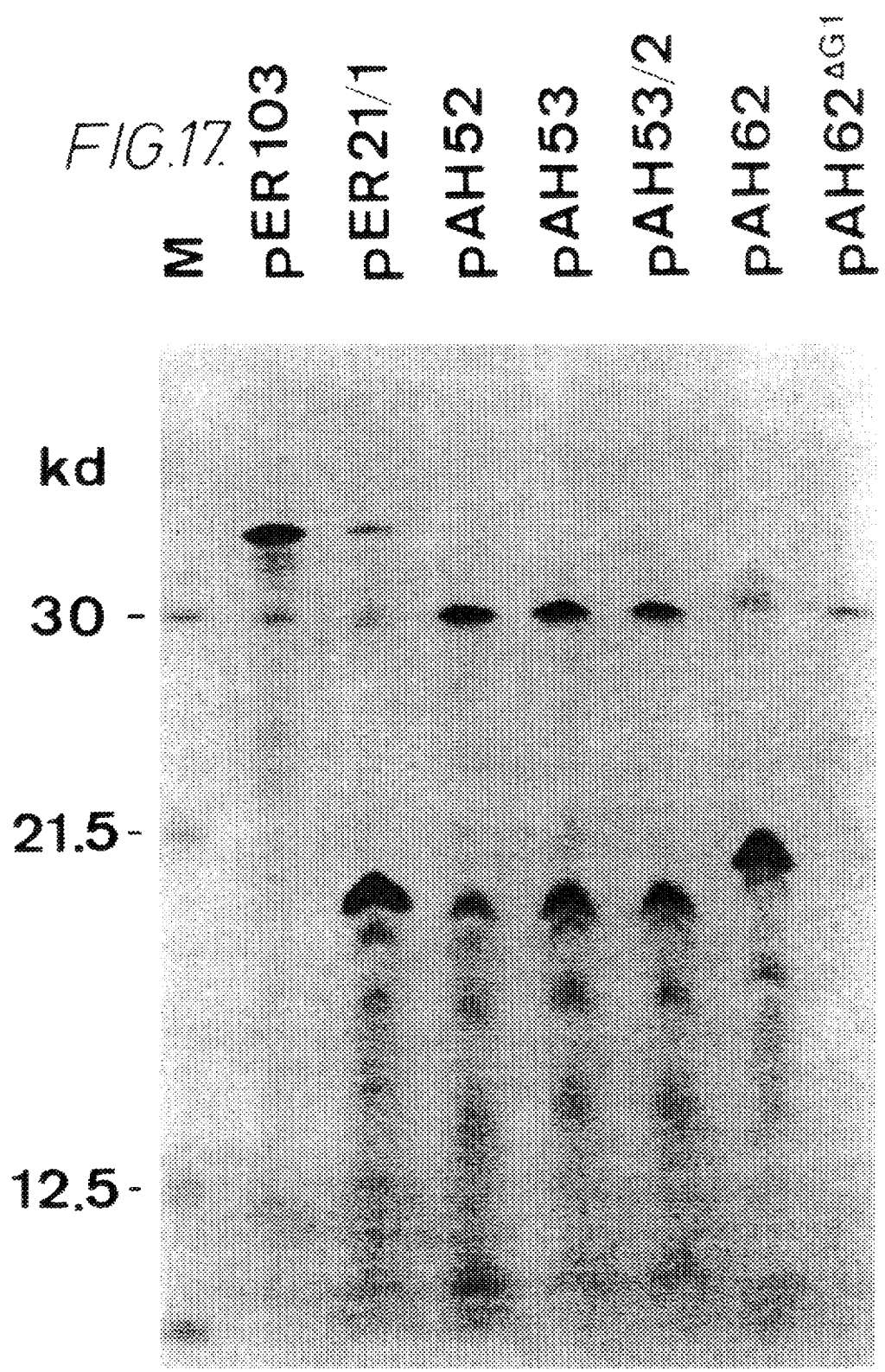

|         | 10         | 20         | 30         | 40         | 50         | 60         |
|---------|------------|------------|------------|------------|------------|------------|
| EqALF1  | CDLPHTHSLG | NTRVLMLLGQ | MRRISPFSCL | KDRNDFGFPQ | EVFDGNQFRK | PQAISAVHET |
| EqALF2  | CDLPHTHSLG | NTRVLMLLGQ | MRRISPFSCL | KDRNDFGFPQ | EVFDGNQFRK | PQAISAVHET |
| CaALF1  | CHLPDTHGLR | NWRVLTLLGQ | MRRLSAGSCD | HYTNDFAFPK | ELFDGQRLQE | AQALSVVHVM |
| BoALF1  | CHLPHSHSLA | KRRVLTLLRQ | LRRVSPSSCL | QDRNDFAFPQ | EALGGSQLQK | AQAISVLHEV |
| BoALF2  | CHLPHTHSLP | NRRVLTLLRQ | LRRVSPSSCL | QDRNDFAFPQ | EALGGSQLQK | AQAISVLHEV |
| BoALF3  | CHLPHTHILA | NRRVLMLLGQ | LRRVSPSSCL | QDRNDFAFPQ | EALGGSQLQK | AQAISVLHEV |
| BoALFA  | CHLPHTHSLA | NRRVLMLLQQ | LRRVSPSSCL | QDRNDFEFLQ | EALGGSQLQK | AQAISVLHEV |
| BoALFB  | CHLPHTHSLP | NRRVLTLLRQ | LRRVSPSSCL | QDRNDFAFPQ | EALGGSQLQK | AQAISVLHEV |
| BoALFC  | CHLPHTHSLA | NRRVLMLLGQ | LRRVSPSSCL | QDRNDFAFPQ | EALGGSQLQK | AQAISVLHEV |
| BoALFD  | CHLPHSHSLA | KRRVLTLLRQ | LRRVSPSSCL | QDRNDFAFPQ | EALGGSQLQK | AQAISVLHEV |
| MuALFA  | CDLPQTHNLR | NKRALTLLVQ | MRRLSPLSCL | KDRKDFRFPQ | EKVDAQQIQN | AQAIPVLQEL |
| MuALF1  | CDLPQTHNLR | NKRALTLLVQ | MRRLSPLSCL | KDRKDFGFPQ | EKVDAQQIKK | AQAIPVLSEL |
| MuALF2  | CDLPHTYNLR | NKRALKVLAQ | MRRLPFLSCL | KDRQDFGFPL | EKVDNQQIQK | AQAIPVLRDL |
| MuALF4  | CDLPHTYNLG | NKRALTVLEE | MRRLPPLSCL | KDRKDFGFPL | EKVDNQQIQK | AQAILVLRDL |
| MuALF5  | CDLPQTHNLR | NKRALTLLVK | MRRLSPLSCL | KDRKDFGFPQ | EKVGAQQIQE | AQAIPVLSEL |
| MuALF6  | CDLPQTHNLR | NKRALTLLVK | MRRLSPLSCL | KDRKDFGFPQ | EKVGAQQIQE | AQAIPVLTEL |
| MuALF6a | CDLPQTHKLR | NKRALTLLIQ | MRRLSPLSCL | KDRKDFGFPQ | EKVDTLKIQK | EKAIPVLSEV |
| RaALF   | CDLPHTHNLR | NKRVFTLLAQ | MRRLSPVSCL | KDRKYFGFPL | EKVDGQQIQK | AQAIPVLHEL |
| HuALFA  | CDLPQTHSLG | SRRTLMLLAQ | MRKISLFSCL | KDRHDFGFPQ | EEF-GNQFQK | AETIPVLHEM |
| HuALFB  | CDLPQTHSLG | NRRALILLAQ | MRRISPFSCL | KDRHDFEFPQ | EEFDDKQFQK | AQAISVLHEM |
| HuALFC  | CDLPQTHSLG | NRRALILLGQ | MGRISPFSCL | KDRHDFRIPQ | EEFDGNQFQK | AQAISVLHEM |
| HuALFD  | CDLPETHSLD | NRRTLMLLAQ | MSRISPSSCL | MDRHDFGFPQ | EEFDGNQFQK | APAISVLHEL |
| HuALFF  | CDLPQTHSLG | NRRALILLAQ | MGRISPFSCL | KDRHDFGFPQ | EEFDGNQFQK | AQAISVLHEM |
| HuALFG  | CDLPQTHSLS | NRRTLMIMAQ | MGRISPFSCL | KDRHDFGFPQ | EEFDGNQFQK | AQAISVLHEM |
| HuALFH  | CNLSQTHSLN | NRRTLMLMAQ | MRRISPFSCL | KDRHDFEFPQ | EEFDGNQFQK | AQAISVLHEM |
| HuALFI  | CDLPQTHSLG | NRRALILLAQ | MGRISPFSCL | KDRPDFGLPQ | EEFDGNQFQK | TQAISVLHEM |
| HuALFJ  | CDLPQTHSLR | NRRALILLAQ | MGRISPFSCL | KDRHEFRFPE | EEFDGHQFQK | TQAISVLHEM |
| HuALFK  | CDLPQTHSLG | HRRTMMLLAQ | MRRISLFSCL | KDRHDFRFPQ | EEFDGNQFQK | AEAISVLHEV |
| HuALFL  | CDLPQTHTLR | NRRALILLGQ | MGRISPFSCL | KDRHDFRIPQ | EEFDGNQFQK | AQAISVLHEM |
| HuALFN  | CDLPQTHSLG | NRRALILLAQ | MGRISHFSCL | KDRYDFGFPQ | EVFDGNQFQK | AQAISAFHEM |
| HuOMEGA1| CDLPQNHGLL | SRNTLVLLHQ | MRRISPFLCL | KDRRDFRFPQ | EMVKGSQLQK | AHVMSVLHEM |
| BoALF4  | CDLSPNHVLV | GRQNLRLLGQ | MRRLSPRFCL | QDRKDFAFPQ | EMVEVSQFQE | AQAISVLHEM |
| EqOMEGA1| CDLPASLDLR | KQETLRVLHQ | METISPPSCL | KHRTDFRFPQ | EQLDGRQFPE | AQATSVLQEM |
| EqBETA  | VNY DLLRSQLRSS | NSACLMLLRQ | L-NGAPQRCP | EDTMNFQVPE | EIEQAQQFQK | EDAALVIYEM |
| HuBETA  | MSY NLLGFLQRSS | NFQCQKLLWQ | L-NGRLEYCL | KDRMNFDIPE | EIKQLQQFQK | EDAALTIYEM |
| BoBETA1 | RSY SLLRFQQRQS | LKECQKLLGQ | L-PSTSQHCL | EARMDFQMPE | EMKQEQQFQK | EDAILVMYEV |
| MuBETA  | INY KQLQLQERTN | IRKCQELLEQ | L-NGKI--NL | TYRADFKIPM | EMTE-KM-QK | SYTAFAIQEM |

FIG.19A

```
                70         80         90        100        110        120
EqALF1    IQQIFHLFST DGSSAAWDES LLDKLYTGLY QQLTELEACL SQEVGVEETP LMNEDSLLAV
EqALF2    IQQIFHLFST DGSSAAWDES LLDKLYTGLY QQLTELEACL SQEVGVEETP LMNEDSLLAV
CaALF1    TQKVFHLFCP DTSSAPWNMT LLEELCSGLS EQLDDLEACP LQEAGLAETP LMHEDSTL--
BoALF1    TQHTFQLFST EGSAAVWDES LLDRLRTALD QQLTDLQACL RQEEGLPGAP LLKEDSSLAV
BoALF2    TQHTFQLFST EGSAAVWDQS LLDKLRAALD QQLTDLQACL RQEEGLRGAP LLKEDASLAV
BoALF3    TQHTFQLFST EGSATMWDES LLDKLRDALD QQLTDLQFCL RQEEELQGAP LLKEDSSLAV
BoALFA    TQHTFQLFST EGSPATWDKS LLDKLRAALD QQLTDLQACL TQEEGLRGAP LLKEDSSLAV
BoALFB    TQHTFQLFST EGSATTWDES LLDKLHAALD QQLTDLQACL RQEEGLRGAP LLKEGSSLAV
BoALFC    TQHTFQLFST EGSATMWDES LLDKLRDALD QQLTDLQFCL PQEEELQGAP LLKEDSSLAV
BoALFD    TQHTFQLSST EGSAAVWDES LLDKLRTALD QQLTDLQACL RQEEGLPGAP LLKEDSSLAV
MuALFA    TQQVLNIFTS KDSSAAWDAS LLDSFCNDLH QQLNDLKACV MQEVGVQEPP LTQEDYLLAV
MuALF1    TQQILNIFTS KDSSAAWNAT LLDSFCNDLH QQLNDLQGCL MQQVGVQEFP LTQEDALLAV
MuALF2    TQQTLNLFTS KASSAAWNAT LLDSFCNDLH QQLNDLQTCL MQQVGVQEPP LTQEDALLAV
MuALF4    TQQILNLFTS KDLSATWNAT LLDSFCNDLH QQLNDLKACV MQ-----EPP LTQEDSLLAV
MuALF5    TQQVLNIFTS KDSSAAWNAT LLDSFCNEVH QQLNDLKACV MQQVGVQESP LTQEDSLLAV
MuALF6    TQQILTLFTS KDSSAAWNAT LLDSFCNDLH QLLNDLQGCL MQQVEIQALP LTQEDSLLAV
MuALF6a   TQQILNIFTS KDSSAAWDAT LLDTFCNDLY QQLNDLQACL VQQVRLQEPP LTQEVSLLAV
RaALF     TQQILSLFTS KESSTAWDAT LLDSFCNDLQ QQLSGLQACL MQQVGVQESP LTQEDSLLAV
HuALFA    IQQIFNLFST KDSSAAWDET LLDKFYTELY QQLNDLEACV IQGVGVTETP LMKEDSILAV
HuALFB    IQQTFNLFST KDSSAALDET LLDEFYIELD QQLNDLEVLC DQEVGVIESP LMYEDSILAV
HuALFC    IQQTFNLFST EDSSAAWEQS LLEKFSTELY QQLNDLEACV IQEVGVEETP LMNEDSILAV
HuALFD    IQQIFNLFTT KDSSAAWDED LLDKFCTELY QQLNDLEACV MQEERVGETP LMNVDSILAV
HuALFF    IQQTFNLFST KDSSATWEQS LLEKFSTELN QQLNDMEACV IQEVGVEETP LMNVDSILAV
HuALFG    IQQTFNLFST KDSSATWDET LLDKFYTELY QQLNDLEACM MQEVGVEDTP LMNVDSILTV
HuALFH    MQQTFNLFST KNSSAAWDET LLEKFYIELF QQMNDLEACV IQEVGVEETP LMNEDSILAV
HuALFI    IQQTFNLFST EDSSAAWEQS LLEKFSTELY QQLNNLEACV IQEVGMEETP LMNEDSILAV
HuALFJ    IQQTFNLFST EDSSAAWEQS LLEKFSTELY QQLNDLEACV IQEVGVKETP LMNEDFILAV
HuALFK    IQQTFNLFST KDSSVAWDER LLDKLYTELY QQLNDLEACV MQEVWVGGTP LMNEDSILAV
HuALFL    IQQTFNLFST EDSSAAWEQS LLELFSTELY QQLNDLEACV IQEVGVEETP LMNEDSILAV
HuALFN    IQQTFNLFST KDSSAAWDET LLDKFYIELF QQLNDLEACV TQEVGVEEIA LMNEDSILAV
HuOMEGA1  LQQIFSLFHT ERSSAAWNMT LLDQLHTGLH QQLQHLETCL LQVVGEGESA GAISSSPALTL
BoALF4    LQQSFNLFHK ERSSAAWDTT LLEQLLTGLH QQLDDLDACL GLLTGEEDSA LGRTGPTLAM
EqOMEGA1  LQQIVSLFHT ERSSAAWNTT LLDRLLAGLH QQLEDLNTCL DEQTGEEESA LGTVGPTLAV
EqBETA    LQHTWRIFRR NFASTGWNET IVKNLLVEVH LQMDRLETNL EEIMEEESST WGNTTI-LRL
HuBETA    LQNIFAIFRQ DSSSTGWNET IVENLLANVY HQINHLKTVL EEKLEKEDFT RGKLMSSLHL
BoBETA1   LQHIFGILTR DFSSTGWSET IIEDLLKELY WQMNRLQPIQ KEIMQKQNST TEDTIV-PHL
MuBETA    LQNVFLVFRN NFSSTGWNET IVVRLLDELH QQTVFLKTVL EEKQE-ERLT WEMSSTALHL
```

FIG.19B

```
              130        140        150        160        170
EqALF1    RRYFQRIALY LQEKKYSPCA WEIVRAEIMR SFSSSTNLPQ S
EqALF2    RRYFQRIALY LQEKKYSPCA WEIVRAEIMR CFSSSTNLQQ S
CaALF1    RTYFQRISLY LQDRNHSPCA WEMVRAEIGR SFFSSTILQE RIRRRK
BoALF1    RKYFHRLTLY LQEKRHSPCA WEVVRAQVMR AFSSSTNLQE RFRRKD
BoALF2    RKYFHRLTLY LQEKRHSPCA WEVVRAEVMR AFSSSTNLQE KFRRKD
BoALF3    RKYFHRLTLY LQEKRHSPCA WEVVRAQVMR AFSSSTNLQE SFRRKD
BoALFA    RKYFHRLTLY LQEKRHSPCA WEVVRAEVMR AFSSSTNLQE SFRRKD
BoALFB    RKYFHRLTLY LQEKRHSPCA WEVVRAEVMR AFSSSTNLQE KFRRKD
BoALFC    RKYFHRLTLY LGEKRHSPCA WEVVRAQVMR AFSSSTNLQE SFRRKD
BoALFD    RKYFHRLTLY LQEKRHSPCA WEVVRAQVMR AFSSSTNLQE RFRRKD
MuALFA    RTYFHRITVY LREKKHSPCA WEVVRAEVWR AMSSSAKLLA RLSEEKE
MuALF1    RKYFHRITVY LREKKHSPCA WEVVRAEVWR ALSSSANVLG RLREEK
MuALF2    RKYFHRITVY LREKKHSPCA WEVVRAEVWR ALSSSVNLLP RLSEEKE
MuALF4    RTYFHRITVY LRKKKHSLCA WEVIRAEVWR ALSSSTNLLA RLSEEKE
MuALF5    RKYFHRITVY LREKKHSPCA WEVVRAEVWR ALSSSVNLLA RLSKEE
MuALF6    RTYFHRITVF LREKKHSPCA WEVVRAEVWR ALSSSAKLLA RLNEDE
MuALF6a   RKYFHRITVY LREKKHSPCA WEVVRAEVWR ALSSSANVLG RLREEK
RaALF     REYFHRITVY LRENKHSPCA WEVVKAEVWR ALSSSANLMG RLREERNES
HuALFA    RKYFQRITLY LKEKKYSPCA WEVVRAEIMR SFSLSTNLQE SLRSKE
HuALFB    RKYFQRITLY LTEKKYSSCA WEVVRAEIMR SFSLSINLQK RLKSKE
HuALFC    RKYFQRITLY LIERKYSPCA WEVVRAEIMR SLSFSTNLQK RLRRKD
HuALFD    KKYFRRITLY LTEKKYSPCA WEVVRAEIMR SLSLSTNLQE RLRRKE
HuALFF    KKYFQRITLY LTEKKYSPCA WEVVRAEIMR SFSLSKIFQE RLRRKE
HuALFG    RKYFQRITLY LTEKKYSPCA WEVVRAEIMR SFSLSANLQE RLRRKE
HuALFH    KKYFQRITLY LMEKKYSPCA WEVVRAEIMR SFSFSTNLQK RLRRKD
HuALFI    RKYFQRITLY LTEKKYSPCA WEVVRAEIMR SLSFSTNLQK ILRRKD
HuALFJ    RKYFQRITLY LMEKKYSPCA WEVVRAEIMR SFSFSTNLKK GLRRKD
HuALFK    RKYFQRITLY LTEKKYSPCA WEVVRAEIMR SFSSSRNLQE RLRRKE
HuALFL    RKYFQRITLY LIERKYSPCA NEVVRAEIMR SLSFSTNLQK RLRRKD
HuALFN    RKYFQRITLY LMGKKYSPCA WEVVRAEIMR SFSFSTNLQK GLRRKD
HuOMEGA1  RRYFQGIRVY LKEKKYSDCA WEVVRMEIMK SLFLSTNMQE RLRSKDRDLG SS
BoALF4    KRYFQGIHVY LQEKGYSDCA WEIVRLEIMR SLSSSTSLQE RLRMMDGDLK SP
EqOMEGA1  KRYFRRIRLY LTEKKYSDCA WEIVRVDIMR SFSSSANLQG RLGMKDGDLG SP
EqBETA    KKYYGRISQY LKAKKYSHCA WTVVQAEMLR NLAFLNGLTD YLQN
HuBETA    KRYYGRILHY LKAKEYSHCA WTIVRVEILR NFYFINRLTG YLRN
BoBETA1   GKYYFNLMQY LESKEYDRCA WTVVQVQILT NVSFLMRLTG YVRD
MuBETA    KSYYWRVQRY LKLMKYNSYA WMVVRAEIFR NFLIIRRLTR NFQN
```

FIG. 19C

| PERCENT HOMOLOGY | Eq α1 | Eq α2 | Bo α1 | Bo α2 | Bo α3 | Bo αA | Bo αB | Bo αC | Bo αD | Mu α1 | Mu α2 | Mu α4 | Mu α5 | Mu α6 | Mu α6a | Mu αA | Ra α |
|---|---|---|---|---|---|---|---|---|---|---|---|---|---|---|---|---|---|
| EqIFN-α 1 | -- | 99 | 65 | 65 | 65 | 67 | 65 | 66 | 65 | 59 | 57 | 54 | 57 | 55 | 58 | 59 | 61 |
| EqIFN-α 2 | | -- | 65 | 66 | 66 | 67 | 66 | 67 | 65 | 59 | 57 | 54 | 57 | 55 | 58 | 59 | 61 |
| BoIFN-α 1 | | | -- | 94 | 92 | 91 | 93 | 92 | 99 | 56 | 54 | 51 | 55 | 54 | 57 | 56 | 57 |
| BoIFN-α 2 | | | | -- | 92 | 93 | 96 | 92 | 94 | 58 | 56 | 52 | 56 | 55 | 57 | 57 | 58 |
| BoIFN-α 3 | | | | | -- | 92 | 92 | 99 | 92 | 55 | 54 | 50 | 54 | 55 | 56 | 55 | 57 |
| BoIFN-α A | | | | | | -- | 93 | 92 | 91 | 56 | 55 | 52 | 55 | 54 | 57 | 56 | 57 |
| BoIFN-α B | | | | | | | -- | 92 | 93 | 56 | 54 | 52 | 55 | 54 | 57 | 56 | 58 |
| BoIFN-α C | | | | | | | | -- | 92 | 55 | 54 | 50 | 54 | 55 | 56 | 55 | 57 |
| BoIFN-α D | | | | | | | | | -- | 55 | 54 | 51 | 55 | 54 | 56 | 55 | 57 |
| MuIFN-α 1 | | | | | | | | | | -- | 87 | 80 | 89 | 87 | 89 | 89 | 84 |
| MuIFN-α 2 | | | | | | | | | | | -- | 84 | 83 | 80 | 80 | 83 | 80 |
| MuIFN-α 4 | | | | | | | | | | | | -- | 80 | 78 | 75 | 81 | 74 |
| MuIFN-α 5 | | | | | | | | | | | | | -- | 87 | 82 | 89 | 80 |
| MuIFN-α 6 | | | | | | | | | | | | | | -- | 80 | 85 | 79 |
| MuIFN-α 6a | | | | | | | | | | | | | | | -- | 83 | 80 |
| MuIFN-α A | | | | | | | | | | | | | | | | -- | 79 |
| RaIFN-α | | | | | | | | | | | | | | | | | -- |
| HuIFN-α A | | | | | | | | | | | | | | | | | |
| HuIFN-α B | | | | | | | | | | | | | | | | | |
| HuIFN-α C | | | | | | | | | | | | | | | | | |
| HuIFN-α D | | | | | | | | | | | | | | | | | |
| HuIFN-α F | | | | | | | | | | | | | | | | | |
| HuIFN-α G | | | | | | | | | | | | | | | | | |
| HuIFN-α H | | | | | | | | | | | | | | | | | |
| HuIFN-α I | | | | | | | | | | | | | | | | | |
| HuIFN-α J | | | | | | | | | | | | | | | | | |
| HuIFN-α K | | | | | | | | | | | | | | | | | |
| HuIFN-α L | | | | | | | | | | | | | | | | | |
| HuIFN-α N | | | | | | | | | | | | | | | | | |
| HuIFN-ω1 | | | | | | | | | | | | | | | | | |
| BoIFN-α 4 | | | | | | | | | | | | | | | | | |
| EqIFN-ω1 | | | | | | | | | | | | | | | | | |
| EqIFN-ω | | | | | | | | | | | | | | | | | |
| HuIFN-β | | | | | | | | | | | | | | | | | |
| BoIFN-β 1 | | | | | | | | | | | | | | | | | |
| MuIFN-β | | | | | | | | | | | | | | | | | |

|  | Hu αA | Hu αB | Hu αC | Hu αD | Hu αF | Hu αG | Hu αH | Hu αI | Hu αJ | Hu αK | Hu αL | Hu αN | Hu ω1 | Bo α4 | Eq ω1 | Eq β | Hu β | Bo β1 | Mu β |  |
|---|---|---|---|---|---|---|---|---|---|---|---|---|---|---|---|---|---|---|---|---|
| 76 | 71 | 76 | 73 | 73 | 75 | 74 | 76 | 73 | 76 | 73 | 77 | 57 | 57 | 57 | 30 | 34 | 27 | 27 |  | EqIFN-α1 |
| 76 | 71 | 76 | 73 | 73 | 75 | 74 | 76 | 73 | 76 | 73 | 77 | 57 | 57 | 57 | 30 | 34 | 27 | 27 |  | EqIFN-α2 |
| 61 | 61 | 63 | 63 | 61 | 63 | 63 | 62 | 61 | 65 | 62 | 61 | 51 | 54 | 51 | 27 | 28 | 28 | 26 |  | BoIFN-α1 |
| 61 | 61 | 65 | 63 | 62 | 63 | 63 | 64 | 64 | 65 | 63 | 63 | 51 | 53 | 49 | 28 | 29 | 27 | 26 |  | BoIFN-α2 |
| 61 | 60 | 62 | 62 | 59 | 61 | 62 | 61 | 60 | 65 | 61 | 61 | 49 | 51 | 47 | 29 | 30 | 30 | 27 |  | BoIFN-α3 |
| 63 | 61 | 64 | 63 | 62 | 64 | 65 | 63 | 63 | 65 | 62 | 63 | 50 | 52 | 48 | 27 | 29 | 26 | 25 |  | BoIFN-αA |
| 61 | 61 | 63 | 63 | 61 | 63 | 63 | 63 | 62 | 65 | 61 | 63 | 51 | 53 | 49 | 29 | 31 | 28 | 27 |  | BoIFN-αB |
| 61 | 60 | 63 | 63 | 60 | 62 | 63 | 61 | 61 | 65 | 61 | 61 | 49 | 51 | 47 | 29 | 30 | 30 | 27 |  | BoIFN-αC |
| 61 | 60 | 63 | 63 | 61 | 63 | 63 | 62 | 61 | 65 | 61 | 61 | 51 | 53 | 49 | 27 | 27 | 28 | 25 |  | BoIFN-αD |
| 62 | 63 | 62 | 63 | 61 | 62 | 60 | 61 | 61 | 60 | 62 | 61 | 52 | 51 | 52 | 31 | 31 | 28 | 24 |  | MuIFN-α1 |
| 59 | 61 | 59 | 60 | 58 | 60 | 58 | 58 | 59 | 58 | 59 | 60 | 48 | 47 | 50 | 30 | 29 | 26 | 24 |  | MuIFN-α2 |
| 56 | 57 | 57 | 59 | 55 | 56 | 54 | 56 | 54 | 55 | 55 | 57 | 44 | 46 | 45 | 27 | 27 | 23 | 23 |  | MuIFN-α4 |
| 63 | 64 | 63 | 64 | 61 | 62 | 61 | 61 | 61 | 61 | 63 | 62 | 49 | 51 | 49 | 32 | 29 | 26 | 24 |  | MuIFN-α5 |
| 58 | 59 | 57 | 60 | 57 | 58 | 55 | 57 | 55 | 57 | 57 | 57 | 48 | 49 | 49 | 29 | 28 | 24 | 24 |  | MuIFN-α6 |
| 62 | 61 | 61 | 63 | 59 | 61 | 59 | 61 | 60 | 61 | 61 | 60 | 49 | 49 | 48 | 29 | 31 | 29 | 23 |  | MuIFN-α6a |
| 61 | 63 | 63 | 63 | 61 | 61 | 61 | 61 | 63 | 62 | 63 | 61 | 48 | 50 | 49 | 28 | 27 | 25 | 24 |  | MuIFN-αA |
| 60 | 60 | 59 | 62 | 57 | 60 | 59 | 58 | 58 | 60 | 59 | 59 | 49 | 49 | 49 | 29 | 29 | 27 | 23 |  | RoIFN-α |
| — | — | 81 | 81 | 83 | 82 | 85 | 83 | 81 | 80 | 86 | 79 | 82 | 62 | 54 | 54 | 31 | 34 | 29 | 29 | HuIFN-αA |
|  | — | — | 81 | 77 | 81 | 83 | 82 | 80 | 79 | 81 | 79 | 83 | 58 | 54 | 56 | 32 | 31 | 27 | 29 | HuIFN-αB |
|  |  | — | — | 81 | 89 | 84 | 86 | 94 | 92 | 83 | 98 | 86 | 60 | 58 | 55 | 32 | 33 | 29 | 27 | HuIFN-αC |
|  |  |  | — | — | 83 | 86 | 81 | 80 | 78 | 84 | 79 | 78 | 58 | 55 | 56 | 32 | 32 | 29 | 27 | HuIFN-αD |
|  |  |  |  | — | — | 88 | 84 | 89 | 86 | 83 | 87 | 83 | 57 | 55 | 55 | 31 | 32 | 26 | 27 | HuIFN-αF |
|  |  |  |  |  | — | — | 86 | 83 | 81 | 87 | 82 | 84 | 59 | 55 | 57 | 33 | 34 | 28 | 27 | HuIFN-αG |
|  |  |  |  |  |  | — | — | 84 | 84 | 83 | 84 | 86 | 57 | 58 | 55 | 35 | 34 | 29 | 29 | HuIFN-αH |
|  |  |  |  |  |  |  | — | — | 91 | 81 | 92 | 86 | 58 | 56 | 54 | 33 | 33 | 29 | 27 | HuIFN-αI |
|  |  |  |  |  |  |  |  | — | — | 80 | 90 | 84 | 57 | 54 | 54 | 32 | 33 | 29 | 26 | HuIFN-αJ |
|  |  |  |  |  |  |  |  |  | — | — | 80 | 81 | 58 | 54 | 54 | 31 | 32 | 29 | 28 | HuIFN-αK |
|  |  |  |  |  |  |  |  |  |  | — | — | 83 | 59 | 57 | 55 | 32 | 32 | 28 | 27 | HuIFN-αL |
|  |  |  |  |  |  |  |  |  |  |  | — | — | 57 | 55 | 55 | 32 | 34 | 28 | 29 | HuIFN-αN |
|  |  |  |  |  |  |  |  |  |  |  |  | — | — | 63 | 61 | 32 | 32 | 26 | 31 | HuIFN-ω1 |
|  |  |  |  |  |  |  |  |  |  |  |  |  | — | — | 64 | 33 | 35 | 29 | 29 | BoIFN-α4 |
|  |  |  |  |  |  |  |  |  |  |  |  |  |  | — | — | 32 | 35 | 27 | 29 | EqIFN-ω1 |
|  |  |  |  |  |  |  |  |  |  |  |  |  |  |  | — | — | 59 | 50 | 44 | EqIFN-β |
|  |  |  |  |  |  |  |  |  |  |  |  |  |  |  |  | — | — | 51 | 47 | HuIFN-β |
|  |  |  |  |  |  |  |  |  |  |  |  |  |  |  |  |  | — | — | 35 | BoIFN-β1 |
|  |  |  |  |  |  |  |  |  |  |  |  |  |  |  |  |  |  | — | — | MuIFN-β |

CONTINUED FROM FIG.20A

FIG.20B

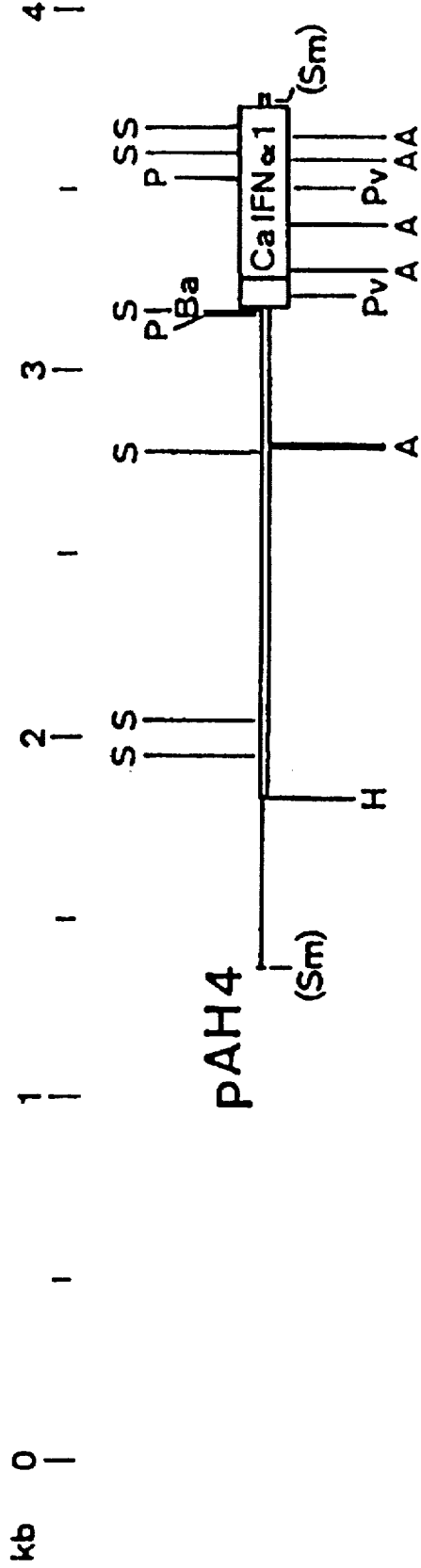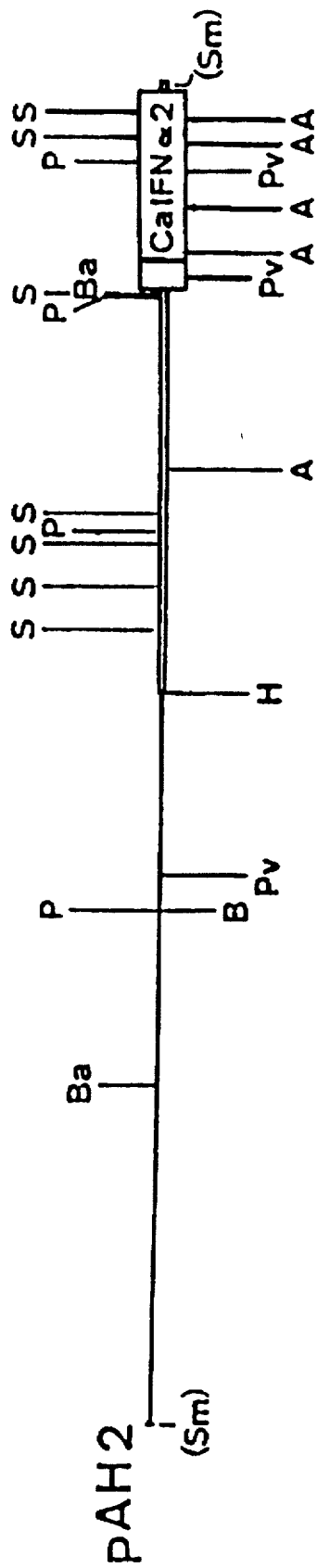
FIG. 23

FIG. 24A

```
                                  20                        25                        30                        35
      Leu Gly Gln Met Arg Arg Leu Ser Ala Gly Ser Cys Asp His Tyr Thr Asn Asp Phe Ala
      CTG GGA CAG ATG AGG AGA CTC TCC GCC GGC TCT TGT GAC CAC TAC ACC AAT GAC TTT GCC    1292

40                        45                        50                        55
      Phe Pro Lys Glu Leu Phe Asp Gly Gln Arg Leu Gln Glu Ala Gln Ala Leu Ser Val Val
      TTC CCC AAG GAG CTG TTT GAT GGG CAG CGG CTC CAG GAG GCC CAG GCC CTC TCT GTG GTC    1352

60                        65                        70                        75
      His Val Met Thr Gln Lys Val Phe His Leu Phe Cys Pro Asp Thr Ser Ser Ala Pro Trp
      CAC GTG ATG ACC CAG AAG GTC TTC CAC CTC TTC TGC CCG GAC ACC TCC TCT GCT CCT TGG    1412

80                        85                        90                        95
      Asn Met Thr Leu Leu Glu Glu Leu Cys Ser Gly Leu Ser Glu Leu Asp Asp Leu Glu
      AAC ATG ACT CTC CTG GAG GAA CTG TGC TCG GGG CTC TCT GAG CTG GAT GAC CTG GAG       1472
                                           Hgi AI                      Pvu II 100                       105                       110                       115
      Ala Cys Pro Leu Gln Glu Ala Gly Leu Ala Glu Thr Pro Leu Met His Glu Asp Ser Thr
      GCC TGT CCC CTG CAG GAG GCC GGG CTG GCC GAG ACC CCC CTC ATG CAT GAG GAC TCC ACC   1532
                              Pst I 120                       125                       130                       135
      Leu Arg Thr Tyr Phe Gln Arg Ile Ser Leu Tyr Leu Gln Asp Arg Asn His Ser Pro Cys
      CTG AGG ACC TAC TTC CAA AGG ATC TCC CTC TAC CTG CAA GAC AGG AAC CAC AGC CCG TGT   1592
```

FIG.24B

```
                    140             145                 150                 155
Ala Trp Glu Met Val Arg Ala Glu Ile Gly Arg Ser Phe Phe Ser Ser Thr Ile Leu Gln
GCC TGG GAG ATG GTC CGA GCA GAA ATC GGG AGA TCC TTC TTC TCC TCG ACA ATC TTG CAA   1652

160                 165           *
Glu Arg Ile Arg Arg Arg Lys
GAA AGA ATC AGG AGG AGG AAA TGA GACCCCGGCCCCGGATCCGGTCGACCTGCAGCCAAGCTT            1711
                                                    BamHI       PstI  HindIII
                                                         pUC9
```

FIG.24C

```
                                                                              AAGCTTGACC        10
CTGGAGAGGCCTAACGAAACCTTCTTCCTTAGTATTTAATGTCTCTCAATTGGGTTTTCTTGGGTACCACACAAGCATTG               89
ACATTGAATATTTGGAAGACACAAATTGCCTGCAAGATCAGTGTGACAAGCCTAGGAATAGCAGGAATACTTTAGGCTT              168
GCAAGAATTTCTTCCATCATTTCTTAGACCTCAAAATCTCAAATCTTGATGTCATGCTGGCCTTGGCAATTAAAACAAATAGATGATATTT  247
TGGCTGTCTTATAGATGATACTTGTCTGAGCCTTGATGTCATGCTGGCCTTGGCAATTAAAACAGAAAATATTCTGACATTACA         326
TATGATTTAATTCTATTAAACTTATTCAACATACAGTAATTATATAGAATTAAATTATTAAACAGTTAAATTATTAATACAATTAAAAGT   405
TACAAGAGTATCTAGCAGCAGGTGTAGTATATAGAATTAAACAGTTAAATTATTAAACAGTTAAATTATTAATACAATTAAAAGT        484
TAAAAATTATTTGTAATATGAGGCAACAATATCATTATCCTAAGGAATGTTAATTCTTTAATTTCTTAATTTTCACTAGC             563
TTTTAGCAATTGGGAATAATTTAAATTTGTATGAGTAAAGAATACTCACCAAATTTAGTTTAGTACTTTACCTATGCTTACTTATTTGC    642
ATATGCACCTTATCTATTTCAATTGTATGAGTAAAGAATACTCACCAAATTTAGTTTAGTACTTACTTTACACTTT                 721
ATCAATAGCTGTAAATTTAACTTTAGATAAAATCTTTAGTCATCCGCAAACTGTATTAGGTAAACTTTACACTTT                  800
CTTTTTACATATTAACCACAGGTATAAATACAACATATTATATGTACTATGTATCCATGCTATTAAGTATTCTAG                  879
GAATGTTCACTAAAAAATTCCAGAGTCCCATTGGGCTTGCCTGAGTAGCTCAGTGGTTGAGCATCTCCCTGCCTATCTCTTTG          958
TCCCAGGTCCTGGGTCCGAGTCCCATTGGGCTTGCCTGAGTAGCTCAGTGGTTGAGCATCTCCCTGCTATGTCTGTCTCTG            1037
TTTCTGTGTCTCTCCTGAATAAATAAAATGAAAATCTTTAAAAAATAAATTTTAAAACCACCAAAAACACTCTG                   1116
GAAGCAAGAGGCATGAAAAGAAAGTGAGGGAGGACATTCCCACACTTGCCCAGGCAACAGTACTCTCAAACCCATGCCTCTTGCCCAACG   1195
AAAAAGAGAAGAAAATAAATAATGGAAGGCAACAGTACTCTCAAACCCATGCCTCTTGCCAACGCGGTCGCATAAGGAAAGC           1274
AAGATGCTCAGAGAAGCTGAAGCCGGGTTCCCACACTTGCCCAGGCCAGGCCAGCCCACACCCCTGCAGGATCCCCG                1353

-20                     -15                     -10                    -5
Met Ala Leu Pro Cys Ser Phe Ser Val Ala Leu Val Leu Leu Ser Cys His Ser Leu Cys
ATG GCC CTG CCC TGC TCC TTC TCG GTG GCC CTG GTG CTG CTC AGC TGC CAC TCC CTG TGC             1413

-1    1                         5                      10                     15
Cys Leu Ala Cys His Leu Pro Asp Thr His Gly Leu Arg Asn Trp Arg Val Leu Thr Leu
TGT CTG GCT TGC CAC CTG CCC GAC ACC CAC GGC CTG CGC AAC TGG AGG GTC CTG ACG CTC            1473
```

FIG.25A

```
                    20                  25                  30                  35
Leu Gly Gln Met Arg Arg Leu Ser Ala Gly Ser Cys Asp His Tyr Thr Asn Asp Phe Ala
CTG GGA CAG ATG AGG AGA CTC TCC GCC GGC TCT TGT GAC CAC TAC ACC AAT GAC TTT GCC    1533

40                  45                  50                  55
Phe Pro Lys Glu Leu Phe Asp Leu Phe Gln Arg Leu Gln Glu Ala Gln Ala Leu Ser Val Val
TTC CCC AAG GAG CTG TTT GAT GAG CAG CGG CTC CAG GAG GCG CAG GCC CTC TCT GTG GTC   1593

60                  65                  70                  75
His Val Met Thr Gln Lys Val Phe His Leu Phe Cys Pro Asp Thr Ser Ser Ala Pro Trp
CAC GTG ATG ACC CAG AAG GTC TTC CAC CTC TTC TGC CCG GAC ACG TCC TCT GCT CCT TGG   1653

80                  85                  90                  95
Asn Met Thr Leu Leu Glu Glu Leu Cys Ser Gly Leu Ser Glu Gln Leu Asp Asp Leu Glu
AAC ATG ACT CTC CTG GAG GAA CTG TGC TCG GGG CTC TCT GAG CAG CTG GAT GAC CTG GAG   1713

100                 105                 110                 115
Ala Cys Pro Leu Gln Glu Ala Gly Leu Ala Glu Thr Pro Leu Met His Glu Asp Ser Thr
GCC TGT CCC CTG CAG GAG GCG GGG CTG GCC GAG ACC CCC CTC ATG CAT GAG GAC TCC ACC   1773

120                 125                 130                 135
Leu Arg Thr Tyr Phe Gln Arg Ile Ser Leu Tyr Leu Gln Glu Lys Gln Tyr Ser Pro Cys
CTG AGG ACC TAC TTC CAA AGG ATC TCC CTC TAC CTG CAA GAC AGG AAC CAC AGC CCG TGT   1833

140                 145                 150                 155
Ala Trp Glu Met Val Arg Ala Glu Ile Gly Arg Ser Phe Phe Ser Thr Ile Leu Gln
GCC TGG GAG ATG GTC CGA GCA GAA ATC GGG AGA TCC TTC TTC TCG ACA ATC TTG CAA       1893
```

FIG. 25B

```
              10         20         30         40         50         60         70         80         90
CaALF1   CHLPDTHGLR NWRVLTLLGQ MRRLSAGSCD HYTNDFAFPK ELFDGQRLQE AQALSVVHVM TQKVFHLFCP DTSSAPWNMT LLEELCSGLS

BoALF1   CHLPHSHSLA KRRVLTLLRQ LRRVSPSSCL QDRNDFAFPQ EALGGSQLQK AQAISVLHEV TQHTFQLFST EGSAAVWDES LLDRLRTALD
BoALF2   CHLPHTHSLP NRRVLTLLRQ LRRVSPSSCL QDRNDFAFPQ EALGGSQLQK AQAISVLHEV TQHTFQLFST EGSAAVWDQS LLDKLRAALD
BoALF3   CHLPHTHILA NRRVLMLLGQ LRRVSPSSCL QDRNDFAFPQ EALGGSQLQK AQAISVLHEV TQHTFQLFST EGSATMWDES LLDKLRDALD

MuALF1   CDLPQTHNLR NKRALTLLVQ MRRLSPLSCL KDRKDFGFPQ EKVDAQQIKK AQAIPVLSEL TQQILNIFTS KDSSAAWNAT LLDSFCNDLH
MuALF2   CDLPHTYNLR NKRALKVLAQ MRRLPFLSCL KDRQDFGFPL EKVDNQQIQK AQAIPVLRDL TQQTLNLFTS KASSAAWNAT LLDSFCNDLH

RaALF    CDLPHTHNLR NKRVFTLLAQ MRRLSPVSCL KDRKYFGFPL EKVDGQQIQK AQAIPVLHEL TQQILSLFTS KESSTAWDAT LLDSFCNDLQ
HuALFA   CDLPQTHSLG SRRTLMLLAQ MRKISLFSCL KDRHDFGFPQ EEF-GNQFQK AETIPVLHEM IQQIFNLFST KDSSAAWDET LLDKFYTELY
HuALFB   CDLPQTHSLG NRRALILLAQ MRRISPFSCL KDRHDFEFPQ EEFDDKQFQK AQAISVLHEM IQQTFNLFST KDSSAALDET LLDEFYIELD
HuALFC   CDLPQTHSLG NRRALILLGQ MGRISPFSCL KDRHDFRIPQ EEFDGNQFQK AQAISVLHEM IQQTFNLFST EDSSAAWEQS LLEKFSTELY
HuALFD   CDLPETHSLD NRRTLMLLAQ MSRISPSSCL MDRHDFGFPQ EEFDGNQFQK APAISVLHEL IQQIFNLFTT KDSSAAWDED LLDKFCTELY
HuALFF   CDLPQTHSLG NRRALILLAQ MGRISPFSCL KDAHDFGFPQ EEFDGNQFQK AQAISVLHEM IQQTFNLFST KDSSATWEQS LLEKFSTELN
HuALFG   CDLPQTHSLS NRRTLMIMAQ MGRISPFSCL KDRHDFGFPQ EEFDGNQFQK AQAISVLHEM IQQTFNLFST KDSSATWDET LLDKFYTELY
HuALFH   CNLSQTHSLN NRRTLMLMAQ MRRISPFSCL KDRHDFEFPQ EEFDGNQFQK AQAISVLHEM MQQTFNLFST KNSSAAWDET LLEKFYIELF

HuALFK   CDLPHTHSLG HRRTMMLLAQ MRRISLFSCL KDRHDFRFPQ EEFDGRFRPQ AEAISVLHEV IQQTFNLFST KDSSVAWDER LLDKLYTELY
HuALFL   CDLPQTHTLR NRRALILLGQ MGRISPFSCL KDRHDFRIPQ EEFDGNQFQK AQAISVLHEM IQQTFNLFST EDSSAAWEQS LLELFSTELY

BoALF4   CDLSPNHVLV GRGNLRLLGQ MRRLSPRFCL QDRKDFAFPQ EMVEVSQFQE AQAISVLHEM LQQSFNLFHK ERSSAAWDTT LLEQLLTGLH
```

FIG. 26A

```
              100        110        120        130        140        150        160        170
CaALF1   EQLDDLEACP LQEAGLAETP LMHEDSTL-- RTYFQRISLY LQDRNHSPCA WEMVRAEIGR SFFSSTILQE RIRRRK

BoALF1   QQLTDLQACL RQEEGLPGAP LLKEDSSLAV RKYFHRLTLY LQEKRHSPCA WEVVRAQVMR AFSSSTNLQE RFRRKD
BoALF2   QQLTDLQACL RQEEGLRGAP LLKEDASLAV RKYFHRLTLY LQEKRHSPCA WEVVRAEVMR AFSSSTNLQE KFRRKD
BoALF3   QQLTDLQFCL RQEEELQGAP LLKEDSSLAV RKYFHRLTLY LQEKRHSPCA WEVVRAQVMR AFSSSTNLQE SFRRKD

MuALF1   QQLNDLQGCL MQQVGVQEFP LTQEDALLAV RKYFHRITVY LREKKHSPCA WEVVRAEVWR ALSSSANVLG RLREEK
MuALF2   QQLNDLQTCH MQQVGVQEPP LTQEDALLAV RKYFHRITVY LREKKHSPCA WEVVRAEVWR ALSSSVNLLP RLSEEKE

RaALF    QQLSGLQACL MQQVGVQESP LTQEDSLLAV REYFHRITVY LRENKHSPCA WEVVKAEVWR ALSSSANLMG RLREERNES
HuALFA   QQLNDLEACV IQGVGVTETP LMKEDSILAV RKYFQRITLY LKEKKYSPCA WEVVRAEIMR SFSLSTNLQE SLRSKE
HuALFB   QQLNDLEVLC DQEVGVIESP LMYEDSILAV RKYFQRITLY LTEKKYSSCA WEVVRAEIMR SFSLSINLQK RLKSKE
HuALFC   QQLNDLEACV IQEVGVEETP LMNEDSILAV RKYFQRITLY LIERKYSPCA WEVVRAEIMR SLSFSTNLQK RLRRKD
HuALFD   QQLNDLEACV MQEERVGETP LMMVDSILAV KKYFQRITLY LTEKKYSPCA WEVVRAEIMR SLSLSTNLQK RLRRKE
HuALFF   QQLNDMEACV IQEVGVEETP LMNVDSILAV RKYFRRITLY LTEKKYSPCA WEVVRAEIMR SFSLSKIFQE RLRRKE
HuALFG   QQLNDLEACM MQEVGVEDTP LMNVDSILTV RKYFQRITLY LTEKKYSPCA WEVVRAEIMR SFSLSANLQE RLRRKE
HuALFH   QQMNDLEACV IQEVGVEETP LMNEDSILAV KKYFQRITLY LMEKKYSPCA WEVVRAEIMR SFSFSTNLQK RLRRKD
HuALFK   QQLNDLEACV MQEVWVGGTP LMNEDSILAV RKYFQRITLY LTEKKYSPCA WEVVRAEIMR SFSSSRNLQE RLRRKE
HuALFL   QQLNDLEACV IQEVGVEETP LMNEDSILAV RKYFQRITLY LIERKYSPCA NEVVRAEIMR SLSFSTNLQK RLRRKD

BoALF4   QQLDDLDACL GLLTGEEDSA LGRTGPTLAM KRYFQGIHVY LQEKGYSDCA WEIVRLEIMR SLSSSTSLDE RLRMDGDLK SP
```

Percent sequence identity matrix for interferon-α sequences:

| | Co-α1 | Bo-α1 | Bo-α2 | Bo-α3 | Mu-α1 | Mu-α2 | Ro-α | Hu-αA | Hu-αB | Hu-αC | Hu-αD | Hu-αF | Hu-αG | Hu-αH | Hu-αI | Hu-αJ | Hu-αK | Bo-α4 |
|---|---|---|---|---|---|---|---|---|---|---|---|---|---|---|---|---|---|---|
| Ca IFN-α1 | — | 55 | 55 | 54 | 49 | 48 | 50 | 52 | 52 | 57 | 53 | 55 | 54 | 55 | 63 | 61 | 55 | 49 |
| Bo IFN-α1 | | — | 94 | 92 | 56 | 54 | 57 | 61 | 62 | 63 | 64 | 61 | 63 | 64 | 63 | 64 | 65 | 54 |
| Bo IFN-α2 | | | — | 91 | 58 | 56 | 58 | 61 | 61 | 64 | 63 | 62 | 63 | 63 | 61 | 60 | 64 | 53 |
| Bo IFN-α3 | | | | — | 55 | 54 | 57 | 61 | 60 | 62 | 62 | 59 | 61 | 62 | 58 | 60 | 61 | 45 |
| Mu IFN-α1 | | | | | — | 87 | 84 | 60 | 61 | 60 | 62 | 59 | 62 | 59 | | 59 | 59 | 51 |
| Mu IFN-α2 | | | | | | — | 80 | 60 | 60 | 59 | 59 | 57 | 60 | 58 | 81 | | 57 | 46 |
| Ra IFN-α | | | | | | | — | | 60 | 59 | 62 | 57 | 60 | 59 | 80 | 80 | 59 | 48 |
| Hu IFN-αA | | | | | | | | — | 81 | 81 | 83 | 82 | 85 | 83 | 94 | 79 | 86 | 54 |
| Hu IFN-αB | | | | | | | | | — | 81 | 77 | 81 | 83 | 83 | 80 | 92 | 81 | 54 |
| Hu IFN-αC | | | | | | | | | | — | 81 | 89 | 84 | 86 | 89 | 78 | 83 | 58 |
| Hu IFN-αD | | | | | | | | | | | — | 83 | 86 | 81 | | 86 | 84 | 55 |
| Hu IFN-αF | | | | | | | | | | | | — | 88 | 83 | 84 | | 83 | 56 |
| Hu IFN-αG | | | | | | | | | | | | | — | 86 | | 84 | 83 | 55 |
| Hu IFN-αH | | | | | | | | | | | | | | — | | 91 | 84 | 58 |
| Hu IFN-αI | | | | | | | | | | | | | | | — | | 81 | 56 |
| Hu IFN-αJ | | | | | | | | | | | | | | | | — | 80 | 54 |
| Hu IFN-αK | | | | | | | | | | | | | | | | | — | 54 |
| Bo IFN-α4 | | | | | | | | | | | | | | | | | | — |

```
                            AAATCAGAGATATTATAAGTACACATATCCCTATTAACGGCCTAGTTGG              49

CAAGAATGTCATCAGAGAACCTCGGTCCAAGTTCAGAGACACCCAGTCTCAGCCAGCAGCACCCTCGTTTTCCCC                128
        -20              -15              -10               -5
        Met Ala Leu Leu Pro Ser Leu Leu Thr Ala Leu Val Val Tyr Glu Leu Trp Pro Cys Gly
        ATG GCC CTC CTG CCC TCT CTC TTG ACG GCC CTG GTG GTG TAC GAG TTA TGG CCC TGT GGA    188
          -1   1                  5                      10                 15
        Ala Leu Gly Cys Asp Leu Pro Gln Asn His Ile Leu Val Ser Arg Lys Asn Phe Val Leu
        GCT CTG GGC TGT GAC CTG CCT CAG AAC CAC ATC CTG GTT AGC AGG AAG AAC TTC GTG CTT    248
                20                      25                  30                 35
        Leu Gly Gln Met Ser Arg Ile Ser Ser Ala Ile Cys Leu Lys Asp Arg Lys Asp Phe Arg
        CTG GGC CAA ATG AGC AGA ATC TCC TCC GCA ATC TGT CTG AAG GAC AGA AAA GAC TTC AGG    308
                40                      45                  50                 55
        Phe Pro Gln Asp Met Ala Asp Gly Arg Gln Phe Pro Glu Ala Gln Ala Ala Ser Val Leu
        TTC CCC CAG GAC ATG GCG GAT GGT AGG CAG TTC CCA GAG GCC CAG GCC GCG TCT GTC CTC    368
                60                      65                  70                 75
        His Glu Met Leu Gln Gln Ile Phe Ser Leu Phe His Thr Glu Arg Ser Ser Ala Ala Trp
        CAC GAG ATG CTC CAG CAG ATC TTC AGC CTC TTC CAC ACA GAG CGC TCT TCT GCT GCC TGG    428
```

FIG.31A

```
                                  80                        85                        90                         95
Asn Thr Thr Leu Leu Asp Glu Leu Cys Thr Gly Leu Leu Arg Gln Leu Glu Asp Leu Asp
AAC ACG ACC CTC CTG GAC GAA CTC TGC ACG GGA CTC CTT CGG CAG CTG GAA GAC CTG GAC    488

100                       105                       110                       115
Thr Cys Leu Glu Gln Glu Met Gly Glu Glu Glu Ser Ala Leu Gly Thr Val Arg Pro Thr
ACC TGT TTG GAG CAG GAG ATG GGA GAG GAA GAA TCT GCC CTG GGA ACT GTG CGC CCT ACA    548

120                       125                       130                       135
Leu Ala Val Lys Arg Tyr Phe Arg Gly Ile His Leu Tyr Leu Lys Glu Lys Lys Tyr Ser
CTG GCC GTG AAG AGG TAC TTC CGG GGG ATC CAT CTC TAC CTG AAA GAG AAG AAA TAC AGT    608

140                       145                       150                       155
Asp Cys Ala Trp Glu Ile Val Arg Met Glu Ile Met Arg Ser Phe Ser Ser Ser Ala Asn
GAC TGT GCC TGG GAG ATT GTC CGA ATG GAA ATC ATG AGA TCC TTC TCT TCA TCA GCA AAC    668

160                       165                       170
Leu Gln Gly Arg Leu Arg Met Lys Asp Gly Asp Leu Gly Ser Pro    *
CTG CAA GGA AGG TTA AGA ATG AAG GAT GGA GAC CTG GGC TCA CCT TGA AATGATTCTCCTTAA    731

CTACTGGGTCATGTTACCCTTGCATATGTCCTTGGTCATTCAAAAGGCTCTTATTTCTGCTTTAGTCTAG             802
```

```
                    Leu Pro Ala Ser Leu Asp Leu Arg Lys Gln Glu Thr Leu Arg Val Leu His Gln Met Glu Thr Ile Ser Pro Pro
EqIFN-α1            CTG CCT GCG AGC CTT GAC TTG AGA AAG CAG GAG ACC CTC AGA GTT CTG CAC CAG ATG GAG ACA ATC TCT CCT CCT   149
                     * *         *       * *       * * *       *                       * *                 * * *             *
EqIFN-α2            CTG CCT CAG AAC ATC CAC CTG GTT AGC AGG AAG CAA ATC TTC CTT CTG CAA ATG AGC AGA ATC TCC GCA           149
                    Leu Pro Gln Asn His Ile Leu Val Ser Arg Lys Asn Ile Phe Leu Leu Gln Met Ser Arg Ile Ser Ala

Ser Cys Leu Lys His Arg Thr Asp Phe Arg Phe Pro Gln Glu Gln Leu Asp Gly Arg Gln Phe Pro Glu Ala Gln
EqIFN-α1            TCC TGT CTG AAG CAC AGG ACA GAC TTC AGG TTC CCC CAG GAG CAG CTG GAT GGC AGG CAG TTC CCA GAG GCC CAG   224
                     * *                     *       *     *                             *   * *                                       224
EqIFN-α2            ATC TGT CTG AAG GAC AGA AAA GAC TTC AGG TTC CCC CAG ATG GAC GCG ATG GAT GGC ATG GCG AGG CAG GCC CAG
                    Ile Cys Leu Lys Asp Arg Lys Asp Phe Arg Phe Pro Gln Met Asp Ala Met Asp Gly Met Ala Arg Gln Ala Gln

Ala Thr Ser Val Leu Gln Met Leu Gln Gln Ile Val Ser Leu Phe His Thr Glu Arg Ser Ser Ala Ala Trp
EqIFN-α1            GCC ACC TCT GTC CTC CAG ATG CTC CAG CAG ATC GTC AGC CTC TTC CAC ACA GAG CGC TCG TCT GCT GCC TGG       299
                            *                                                                 *                                       299
EqIFN-α2            GCC GCC TCT GTC CTC CAG ATG CTC CAG CAG ATC CAG ATC TTC AGC CTC TTC CAC ACA GAG CGC TCT GCT GCC TGG
                    Ala Ala Ser Val Leu Gln Met Leu Gln Gln Ile Gln Ile Phe Ser Leu Phe His Thr Glu Arg Ser Ala Ala Trp
```

```
                    80                    85                    90                    95                   100
EqIFN-α1  Asn Thr Leu Leu Asp Arg Leu Leu Ala Gly Leu His Gln Leu Glu Asp Leu Asn Thr Cys Leu Asp Glu
          AAC ACT CTC CTG GAC CGA CTC CTC GCG GGA CTC CAT CAG CTG GAA GAC CTC AAC ACC TGC TTG GAT GAG  374
                            *                       **          *                   *       *   *
EqIFN-α2  AAC ACC CTC CTG GAC CTT CTC ACG TGC GAA CTC CTT CAG CAG GAA GAC CTG GAA GAC TGT TTG GAG CAG  374
          Asn Thr Leu Leu Asp Leu Leu Thr Cys Glu Leu Leu Gln Gln Glu Asp Leu Glu Asp Cys Leu Glu Gln 105                   110                   115                   120                   125
EqIFN-α1  Gln Thr Gly Glu Glu Ser Ala Leu Gly Thr Val Gly Pro Thr Leu Ala Leu Val Lys Arg Tyr Phe Arg Ile
          CAG ACA GGA GAG GAA TCC GCC CTG GGA ACT GTG GGC CCT ACA CTG GCC CTG GTG AAG AGG TAC TTC CGG ATC  449
              **                                      *           *                       *       *   **
EqIFN-α2  CAG ATG GGA GAG GAG TCT GCC CTG GGA CTC GTG CGC CCT ACA CTG GCC CTG GTG AAG AGG TAC TTC CGG ATC  449
          Gln Met Gly Glu Glu Ser Ala Leu Gly Leu Val Arg Pro Thr Leu Ala Leu Val Lys Arg Tyr Phe Arg Ile 130                   135                   140                   145                   150
EqIFN-α1  Arg Leu Tyr Leu Thr Glu Lys Lys Tyr Ser Asp Cys Ala Trp Glu Ile Val Arg Val Asp Ile Met Arg Ser Phe
          CGT CTC TAC CTG ACA GAG AAA AAG TAC AGT GAC TGT GCC TGG GAG ATT GTC AGA GTG GAC ATC ATG AGA TCC TTC  524
                  *                       *                           *                       *
EqIFN-α2  CAT CTC TAC CTG AAA GAG AAG AAG TAC AGT GAC TGT GCC TGG GAG ATT GTC CGA GAG ATG ATC ATG AGA TCC TTC  524
          His Leu Tyr Leu Lys Glu Lys Lys Tyr Ser Asp Cys Ala Trp Glu Ile Val Arg Glu Met Ile Met Arg Ser Phe 155                   160                   165                   170
EqIFN-α1  Ser Ser Ala Asn Leu Gln Gly Arg Leu Met Lys Asp Gly Asp Leu Gly Ser Pro *
          TCT TCA GCA AAC CTG CAA GGA AGG TTA ATG AAG GAT GGA GAC CTG GGG TCA CCT TGA AATGATTCTCCTACA  602
                                      *       **          *                   *                        **
EqIFN-α2  TCT TCA TCA GCA AAC CTG CAA GGA AGG TTA AGA ATG AAG GAT GGA GAC CTG GGG TCA CCT TGA AATGATTCTCCTTAA  602
          Ser Ser Ser Ala Asn Leu Gln Gly Arg Leu Arg Met Lys Asp Gly Asp Leu Gly Ser Pro *
```

```
                                                                    688   673
EqIFN-α1  CTACTGGGCCATGGCACCCTTGCACCTGTCTTTAGTCATTTCAAAAGGCTCTTATTTCTGCTTTGGTCATATACTTTATTGAATTC
                  *  **        **              *                          *  ***
EqIFN-α2  CTACTGGGTCATGTTACCCTTGCATATGTCCTTGGTCATTTCAAAAGGCTCTTATTTCTGCTTTAGTCTAG
```

FIG. 32D

| PERCENT HOMOLOGY | Eq α1 | Eq α2 | Co α1 | Bo α1 | Bo α2 | Bo α3 | Bo αA | Bo αB | Bo αC | Bo αD | Mu α1 | Mu α2 | Mu α4 | Mu α5 | Mu α6 | Mu α6a | Mu αA | Ra α |
|---|---|---|---|---|---|---|---|---|---|---|---|---|---|---|---|---|---|---|
| EqIFN-α1 | -- | 99 | 59 | 65 | 65 | 65 | 67 | 65 | 66 | 65 | 59 | 57 | 54 | 57 | 55 | 58 | 59 | 61 |
| EqIFN-α2 |  | -- | 59 | 65 | 66 | 66 | 67 | 66 | 67 | 65 | 59 | 57 | 54 | 57 | 55 | 58 | 59 | 61 |
| CoIFN-α 1+2 |  |  | -- | 55 | 55 | 54 | 54 | 55 | 54 | 54 | 49 | 48 | 48 | 50 | 48 | 48 | 51 | 50 |
| BoIFN-α1 |  |  |  | -- | 94 | 92 | 91 | 93 | 92 | 99 | 56 | 54 | 51 | 55 | 54 | 57 | 56 | 57 |
| BoIFN-α2 |  |  |  |  | -- | 92 | 93 | 96 | 92 | 94 | 58 | 56 | 52 | 56 | 55 | 57 | 57 | 58 |
| BoIFN-α3 |  |  |  |  |  | -- | 92 | 92 | 99 | 92 | 55 | 54 | 50 | 54 | 55 | 56 | 55 | 57 |
| BoIFN-αA |  |  |  |  |  |  | -- | 93 | 92 | 91 | 56 | 55 | 52 | 55 | 54 | 57 | 56 | 57 |
| BoIFN-αB |  |  |  |  |  |  |  | -- | 92 | 93 | 56 | 54 | 52 | 55 | 54 | 57 | 56 | 58 |
| BoIFN-αC |  |  |  |  |  |  |  |  | -- | 92 | 55 | 54 | 50 | 54 | 55 | 56 | 55 | 57 |
| BoIFN-αD |  |  |  |  |  |  |  |  |  | -- | 55 | 54 | 51 | 55 | 54 | 56 | 55 | 57 |
| MuIFN-α1 |  |  |  |  |  |  |  |  |  |  | -- | 87 | 80 | 89 | 87 | 89 | 89 | 84 |
| MuIFN-α2 |  |  |  |  |  |  |  |  |  |  |  | -- | 84 | 83 | 80 | 80 | 83 | 80 |
| MuIFN-α4 |  |  |  |  |  |  |  |  |  |  |  |  | -- | 80 | 78 | 75 | 81 | 74 |
| MuIFN-α5 |  |  |  |  |  |  |  |  |  |  |  |  |  | -- | 87 | 82 | 89 | 80 |
| MuIFN-α6 |  |  |  |  |  |  |  |  |  |  |  |  |  |  | -- | 80 | 85 | 79 |
| MuIFN-α6a |  |  |  |  |  |  |  |  |  |  |  |  |  |  |  | -- | 83 | 80 |
| MuIFN-αA |  |  |  |  |  |  |  |  |  |  |  |  |  |  |  |  | -- | 79 |
| RaIFN-α |  |  |  |  |  |  |  |  |  |  |  |  |  |  |  |  |  | -- |
| HuIFN-αA |  |  |  |  |  |  |  |  |  |  |  |  |  |  |  |  |  |  |
| HuIFN-αB |  |  |  |  |  |  |  |  |  |  |  |  |  |  |  |  |  |  |
| HuIFN-αC |  |  |  |  |  |  |  |  |  |  |  |  |  |  |  |  |  |  |
| HuIFN-αD |  |  |  |  |  |  |  |  |  |  |  |  |  |  |  |  |  |  |
| HuIFN-αF |  |  |  |  |  |  |  |  |  |  |  |  |  |  |  |  |  |  |
| HuIFN-αG |  |  |  |  |  |  |  |  |  |  |  |  |  |  |  |  |  |  |
| HuIFN-αH |  |  |  |  |  |  |  |  |  |  |  |  |  |  |  |  |  |  |
| HuIFN-αI |  |  |  |  |  |  |  |  |  |  |  |  |  |  |  |  |  |  |
| HuIFN-αJ |  |  |  |  |  |  |  |  |  |  |  |  |  |  |  |  |  |  |
| HuIFN-αK |  |  |  |  |  |  |  |  |  |  |  |  |  |  |  |  |  |  |
| HuIFN-αL |  |  |  |  |  |  |  |  |  |  |  |  |  |  |  |  |  |  |
| HuIFN-αN |  |  |  |  |  |  |  |  |  |  |  |  |  |  |  |  |  |  |
| HuIFN-ω1 |  |  |  |  |  |  |  |  |  |  |  |  |  |  |  |  |  |  |
| BoIFN-α4 |  |  |  |  |  |  |  |  |  |  |  |  |  |  |  |  |  |  |
| EqIFN-ω1 |  |  |  |  |  |  |  |  |  |  |  |  |  |  |  |  |  |  |
| EqIFN-ω2 |  |  |  |  |  |  |  |  |  |  |  |  |  |  |  |  |  |  |
| EqIFN-β |  |  |  |  |  |  |  |  |  |  |  |  |  |  |  |  |  |  |
| HuIFN-β |  |  |  |  |  |  |  |  |  |  |  |  |  |  |  |  |  |  |
| BoIFN-β1 |  |  |  |  |  |  |  |  |  |  |  |  |  |  |  |  |  |  |
| MuIFN-β |  |  |  |  |  |  |  |  |  |  |  |  |  |  |  |  |  |  |

| Hu αA | Hu αB | Hu αC | Hu αD | Hu αF | Hu αG | Hu αH | Hu αI | Hu αJ | Hu αK | Hu αL | Hu αN | Hu ω1 | Bo α4 | Eq ω1 | Eq ω2 | Eq β | Hu β | Bo β1 | Mu β | |
|---|---|---|---|---|---|---|---|---|---|---|---|---|---|---|---|---|---|---|---|---|
| 76 | 71 | 76 | 73 | 73 | 75 | 74 | 76 | 73 | 76 | 73 | 77 | 57 | 57 | 57 | 60 | 30 | 34 | 27 | 27 | EqIFN-α1 |
| 76 | 71 | 76 | 73 | 73 | 75 | 74 | 76 | 73 | 76 | 73 | 77 | 57 | 57 | 57 | 60 | 30 | 34 | 27 | 27 | EqIFN-α2 |
| 52 | 52 | 57 | 53 | 55 | 54 | 55 | 54 | 54 | 54 | 57 | 54 | 47 | 49 | 44 | 48 | 26 | 27 | 22 | 24 | CaIFN-α1+2 |
| 61 | 61 | 63 | 63 | 61 | 63 | 63 | 62 | 61 | 65 | 62 | 61 | 51 | 54 | 51 | 51 | 27 | 28 | 28 | 26 | BoIFN-α1 |
| 61 | 61 | 65 | 63 | 62 | 63 | 63 | 64 | 64 | 65 | 63 | 63 | 51 | 53 | 49 | 51 | 28 | 29 | 27 | 26 | BoIFN-α2 |
| 61 | 60 | 62 | 62 | 59 | 61 | 62 | 61 | 60 | 65 | 61 | 61 | 49 | 51 | 47 | 50 | 29 | 30 | 30 | 27 | BoIFN-α3 |
| 63 | 61 | 64 | 63 | 62 | 64 | 65 | 63 | 63 | 65 | 62 | 63 | 50 | 52 | 48 | 50 | 27 | 29 | 26 | 25 | BoIFN-αA |
| 61 | 61 | 63 | 63 | 61 | 63 | 63 | 63 | 62 | 65 | 61 | 63 | 51 | 53 | 49 | 50 | 29 | 31 | 28 | 27 | BoIFN-αB |
| 61 | 60 | 63 | 63 | 60 | 62 | 63 | 61 | 61 | 65 | 61 | 61 | 49 | 51 | 47 | 49 | 29 | 30 | 30 | 27 | BoIFN-αC |
| 61 | 60 | 63 | 63 | 61 | 63 | 63 | 62 | 61 | 65 | 61 | 61 | 51 | 53 | 49 | 51 | 27 | 27 | 28 | 25 | BoIFN-αD |
| 62 | 63 | 62 | 63 | 61 | 62 | 60 | 61 | 61 | 60 | 62 | 61 | 52 | 51 | 52 | 52 | 31 | 31 | 28 | 24 | MuIFN-α1 |
| 59 | 61 | 59 | 60 | 58 | 60 | 58 | 58 | 59 | 58 | 59 | 60 | 48 | 47 | 50 | 47 | 30 | 29 | 26 | 24 | MuIFN-α2 |
| 56 | 57 | 57 | 59 | 55 | 56 | 54 | 56 | 54 | 55 | 55 | 57 | 44 | 46 | 45 | 44 | 27 | 27 | 23 | 23 | MuIFN-α4 |
| 63 | 64 | 63 | 64 | 61 | 62 | 61 | 61 | 61 | 61 | 63 | 62 | 49 | 51 | 49 | 49 | 32 | 29 | 26 | 24 | MuIFN-α5 |
| 58 | 59 | 57 | 60 | 57 | 58 | 55 | 57 | 55 | 57 | 57 | 57 | 48 | 49 | 49 | 49 | 29 | 28 | 24 | 24 | MuIFN-α6 |
| 62 | 61 | 61 | 63 | 59 | 61 | 59 | 61 | 60 | 61 | 61 | 60 | 49 | 49 | 48 | 49 | 29 | 31 | 29 | 23 | MuIFN-α6a |
| 61 | 63 | 63 | 63 | 61 | 61 | 61 | 61 | 63 | 62 | 63 | 61 | 48 | 50 | 49 | 50 | 28 | 27 | 25 | 24 | MuIFN-αA |
| 60 | 60 | 59 | 62 | 57 | 60 | 59 | 58 | 58 | 60 | 59 | 59 | 49 | 49 | 49 | 51 | 29 | 29 | 27 | 23 | RaIFN-α |
| -- | 81 | 81 | 83 | 82 | 85 | 83 | 81 | 80 | 86 | 79 | 82 | 62 | 54 | 54 | 58 | 31 | 34 | 29 | 29 | HuIFN-αA |
| | -- | 81 | 77 | 81 | 83 | 82 | 80 | 79 | 81 | 79 | 83 | 58 | 54 | 56 | 58 | 32 | 31 | 27 | 29 | HuIFN-αB |
| | | -- | 81 | 89 | 84 | 86 | 94 | 92 | 83 | 98 | 86 | 60 | 58 | 55 | 60 | 32 | 33 | 29 | 27 | HuIFN-αC |
| | | | -- | 83 | 86 | 81 | 80 | 78 | 84 | 79 | 78 | 58 | 55 | 56 | 60 | 32 | 32 | 29 | 27 | HuIFN-αD |
| | | | | -- | 88 | 84 | 89 | 86 | 83 | 87 | 83 | 57 | 55 | 55 | 58 | 31 | 32 | 26 | 27 | HuIFN-αF |
| | | | | | -- | 86 | 83 | 81 | 87 | 82 | 84 | 59 | 55 | 57 | 59 | 33 | 34 | 28 | 27 | HuIFN-αG |
| | | | | | | -- | 84 | 84 | 83 | 84 | 86 | 57 | 58 | 55 | 58 | 35 | 34 | 29 | 29 | HuIFN-αH |
| | | | | | | | -- | 91 | 81 | 92 | 86 | 58 | 56 | 54 | 58 | 33 | 33 | 29 | 27 | HuIFN-αI |
| | | | | | | | | -- | 80 | 90 | 84 | 57 | 54 | 54 | 58 | 32 | 33 | 29 | 26 | HuIFN-αJ |
| | | | | | | | | | -- | 80 | 81 | 58 | 54 | 54 | 58 | 31 | 32 | 29 | 28 | HuIFN-αK |
| | | | | | | | | | | -- | 83 | 59 | 57 | 55 | 60 | 32 | 32 | 28 | 27 | HuIFN-αL |
| | | | | | | | | | | | -- | 57 | 55 | 55 | 59 | 32 | 34 | 28 | 29 | HuIFN-αN |
| | | | | | | | | | | | | -- | 63 | 61 | 67 | 32 | 32 | 26 | 31 | HuIFN-ω1 |
| | | | | | | | | | | | | | -- | 64 | 70 | 33 | 35 | 27 | 29 | BoIFN-α4 |
| | | | | | | | | | | | | | | -- | 75 | 32 | 35 | 27 | 29 | EqIFN-ω1 |
| | | | | | | | | | | | | | | | -- | 32 | 37 | 28 | 30 | EqIFN-ω2 |
| | | | | | | | | | | | | | | | | -- | 59 | 50 | 44 | EqIFN-β |
| | | | | | | | | | | | | | | | | | -- | 51 | 47 | HuIFN-β |
| | | | | | | | | | | | | | | | | | | -- | 35 | BoIFN-β1 |
| | | | | | | | | | | | | | | | | | | | -- | MuIFN-β |

CONTINUED FROM FIG.33B

FIG.33B

```
                                                                         AAAGC    5

GCATAAAGAAAACGAAAACAGAAGTAGAAAGTAAGGAAAACATGCAGAAAATGGAAACTAGTTCCCTATTTAAGACACA   84

TGCACAAAGGAAGGTCTTCAGAGAACCCAGAGAGACCAAGGCTCACAGGGTCACCCACCAGCAGCATCTGCAAGATCCCCA  163

-20             -15              -10              -5
Met Ala Leu Pro Val Ser Leu Leu Met Ala Leu Val Val Leu Ser Cys His Ser Ser Cys
ATG GCT CTG CCT GTT TCC TTA CTG ATG GCC CTG GTG GTG CTC AGC TGC CAC TCC AGC TGC   223

-1   1                           5                          10              15
Ser Leu Gly Cys Asp Leu Pro His Thr His Ser Leu Gly Asn Thr Arg Val Leu Met Leu
TCT CTG GGA TGT GAC CTG CCT CAC ACC CAT AGC CTG GGC AAC ACA AGG GTC TTG ATG CTC   283

20              25              30              35
Leu Gly Gln Met Arg Arg Ile Ser Pro Phe Ser Cys Leu Lys Asp Arg Asn Asp Phe Gly
CTG GGA CAA ATG AGG AGA ATC TCC CCC TTC TCC TGC CTG AAG GAC AGA AAT GAC TTT GGA   343

40              45              50              55
Phe Pro Gln Glu Val Phe Asp Gly Asn Gln Phe Arg Lys Pro Gln Ala Ile Ser Ala Val
TTC CCC CAG GAG GTG TTT GAC GGG AAC CAG TTC CGG AAG CCT CAA GCC ATC TCT GCG GTC   403

60              65              70              75
His Glu Thr Ile Gln Ile Phe His Leu Phe Ser Thr Asp Gly Ser Ser Ala Ala Trp
CAT GAG ACG ATC CAA CAG ATC TTC CAC CTC TTC AGC ACA GAC GGC TCG TCT GCT GCC TGG   463
```

FIG.34A

```
              80                    85                   90                    95
Asp Glu Ser Leu Leu Asp Lys Leu Tyr Thr Gly Leu Tyr Gln Gln Leu Thr Glu Leu Glu
GAC GAG AGC CTC CTA GAC AAG CTC TAC ACT GGA CTC TAT CAG CAG CTG ACT GAG CTG GAA     523

100                   105                  110                   115
Ala Cys Leu Ser Gln Glu Val Gly Val Gly Glu Glu Thr Pro Leu Met Asn Glu Asp Ser Leu
GCC TGT CTG AGC CAG GAG GTG GGG GTG GAA GAG ACG CCC CTG ATG AAC GAG GAC TCC CTG     583

120                   125                  130                   135
Leu Ala Val Arg Arg Tyr Phe Gln Arg Ile Ala Leu Tyr Leu Gln Glu Lys Lys Tyr Ser
CTG GCT GTG AGG AGA TAC TTC CAA AGA ATC GCT CTC TAT CTG CAA GAG AAG AAA TAC AGC     643

140                   145                  150                   155
Pro Cys Ala Trp Glu Ile Val Arg Ala Glu Ile Met Arg Ser Phe Ser Ser Thr Asn
CCT TGT GCC TGG GAG GAG ATC GTC AGA GCA GAA ATC ATG AGA TCC TTC TCT TCA ACA AAC     703

160
Leu Pro Gln Ser *
TTG CCG CAG AGT TAA GGAGGAAGAAATGACACCTGGTTCAACATGGAAATGCTTCTCATGGACTGATAATATCA     777

CACTTCCACTTGCTCTGCCATCTCAAGGACTCTCCATGTCTGCTGTAATCATGACCTGAATTGAATCAATTTTTCAAATG    856

TTTTCAGTAGTATTAATGAATGTTGGGTCTAACCCTGTGGACATTAGTCTGATACAGAGACCATGTTGATCTATTTAT     935

TTATTTATTTACATATTTATTTAATTATTTATGAGATTTAAATTATTTTTGTTGCTATAACATTATGTGCACCTTTACA    1014

CTGTAGTTTAATATAACAAAATGTATGCTTCATA                                                 1048
```

FIG. 34B

```
                                TCACAGGTCACCCACCCCAGCAGGCCAGCAGCATCTGCAAGATCCCCA                    49
                -20                    -15                    -10                    -5
           Met Ala Leu Pro Phe Ser Leu Leu Met Ala Leu Val Val Leu Ser Cys His Ser Ser Cys
           ATG GCT CTA CCC TTT TCC TTA CTG ATG GCC CTG GTG GTG CTC AGC TGC CAC TCC AGC TGC    109
                 -1  1                          5                             10                    15
           Ser Leu Gly Cys Asp Leu Pro His Thr His Ser Leu His Gly Asn Thr Arg Val Leu Met Leu
           TCT CTG GGA TGT GAC CTG CCT CAC ACC CAT AGC CTG GGC AAC ACA AGG GTC TTG ATG CTC    169
                       20                            25                            30                            35
           Leu Gly Gln Met Arg Arg Ile Ser Pro Phe Ser Cys Leu Lys Asp Arg Asn Asp Phe Gly
           CTG GGA CAA ATG AGG AGG ATC TCC CCC TTC TCC TGC CTG AAG GAC AGA AAT GAC TTT GGA    229
                       40                            45                            50                            55
           Phe Pro Gln Glu Val Phe Asp Gly Asn Gln Phe Arg Lys Pro Gln Ala Ile Ser Ala Val
           TTC CCC CAG GAG GTG TTT GAC GGC AAC CAG TTC CGG AAG CCT CAA GCC ATC TCC GCG GTC    289
                       60                            65                            70                            75
           His Glu Thr Ile Gln Gln Ile Phe His Leu Phe Ser Thr Asp Gly Ser Ser Ala Ala Trp
           CAT GAG ACG ATC CAA CAG ATC TTC CAC CTC TTC AGC ACA GAC GGC TCG TCT GCC GCC TGG    349
                       80                            85                            90                            95
           Asp Glu Ser Leu Leu Asp Lys Leu Tyr Thr Gly Leu Tyr Gln Gln Leu Thr Glu Leu Glu
           GAC GAG AGC CTC CTA GAC AAG CTC TAC ACT GGA CTC TAT CAG CAG CTG ACT GAG CTG GAA    409

FIG.35A
```

```
                100                           105                          115
Ala Cys Leu Ser Gln Glu Val Gly Val Glu Glu Thr Pro Leu Met Asn Glu Asp Ser Leu
GCC TGT CTG AGC CAG GAG GTG GGG GTG GAA GAG ACG CCC CTG ATG AAC GAG GAC TCC CTG       469

120                           125                          135
Leu Ala Val Arg Arg Tyr Phe Gln Arg Ile Thr Leu Tyr Leu Gln Glu Lys Tyr Ser
CTG GCT GTG AGG AGA TAC TTC CAA AGA ATC ACT CTG TAT CTG CAA GAG AAG TAC AGC           529

140                           145                          155
Pro Cys Ala Trp Glu Ile Val Arg Ala Glu Ile Met Arg Ser Phe Ser Ser Thr Asn
CCT TGT GCC TGG GAG ATC GTC AGA GCA GAA ATC ATG AGA TCC TTC TCT TCA ACA AAC           589

160
Leu Pro Gln Ser  *
TTG CCG CAA AGT TAA GGAGGAAGAAATGACACCTGGTTCAACATGGAAATGTGTCTCACTGACTGATAATATCA       663

CACTTCCACTTGCTCTGCCATGTCAAGGACTCTCACTTCTGCTGTAATCATGATCTGAACTCAATCAAATTTGTCAAAT      742

GTTTCAATAGTATTAATGAATATTGTGCTTAACCCTGTGGACACTAGTCTGATACAGATGACCAGGTTGATCTATTTA       821

TTTATCTATTTAAATATTTATTTATTTATTTATGAG                                                  861
```

FIG.35B

```
                        10         20         30         40         50         60
EqALF1      CDLPHTHSLG NTRVLMLLGQ MRRISPFSCL KDRNDFGFPQ EVFDGNQFRK PQAISAVHET
EqALF2      CDLPHTHSLG NTRVLMLLGQ MRRISPFSCL KDRNDFGFPQ EVFDGNQFRK PQAISAVHET
CaALF1      CHLPDTHGLR NWRVLTLLGQ MRRLSAGSCD HYTNDFAFPK ELFDGQRLQE AQALSVVHVM
BoALF1      CHLPHSHSLA KRRVLTLLRQ LRRVSPSSCL QDRNDFAFPQ EALGGSQLQK AQAISVLHEV
BoALF2      CHLPHTHSLP NRRVLTLLRQ LRRVSPSSCL QDRNDFAFPQ EALGGSQLQK AQAISVLHEV
BoALF3      CHLPHTHILA NRRVLMLLGQ LRRVSPSSCL QDRNDFAFPQ EALGGSQLQK AQAISVLHEV
BoALFA      CHLPHTHSLA NRRVLMLLQQ LRRVSPSSCL QDRNDFEFLQ EALGGSQLQK AQAISVLHEV
BoALFB      CHLPHTHSLP NRRVLTLLRQ LRRVSPSSCL QDRNDFAFPQ EALGGSQLQK AQAISVLHEV
BoALFC      CHLPHTHSLA NRRVLMLLGQ LRRVSPSSCL QDRNDFAFPQ EALGGSQLQK AQAISVLHEV
BoALFD      CHLPHSHSLA KRRVLTLLRQ LRRVSPSSCL QDRNDFAFPQ EALGGSQLQK AQAISVLHEV
MuALFA      CDLPQTHNLR NKRALTLLVQ MRRLSPLSCL KDRKDFRFPQ EKVDAQQIQN AQAIPVLQEL
MuALF1      CDLPQTHNLR NKRALTLLVQ MRRLSPLSCL KDRKDFGFPQ EKVDAQQIKK AQAIPVLSEL
MuALF2      CDLPHTYNLR NKRALKVLAQ MRRLPFLSCL KDRQDFGFPL EKVDNQQIQK AQAIPVLRDL
MuALF4      CDLPHTYNLG NKRALTVLEE MRRLPPLSCL KDRKDFGFPL EKVDNQQIQK AQAILVLRDL
MuALF5      CDLPQTHNLR NKRALTLLVK MRRLSPLSCL KDRKDFGFPQ EKVGAQQIQE AQAIPVLSEL
MuALF6      CDLPQTHNLR NKRALTLLVK MRRLSPLSCL KDRKDFGFPQ EKVGAQQIQE AQAIPVLTEL
MuALF6a     CDLPQTHKLR NKRALTLLIQ MRRLSPLSCL KDRKDFGFPQ EKVDTLKIQK EKAIPVLSEV
RaALF       CDLPHTHNLR NKRVFTLLAQ MRRLSPVSCL KDRKYFGFPL EKVDGQQIQK AQAIPVLHEL
HuALFA      CDLPQTHSLG SRRTLMLLAQ MRKISLFSCL KDRHDFGFPQ EEF-GNQFQK AETIPVLHEM
HuALFB      CDLPQTHSLG NRRALILLAQ MRRISPFSCL KDRHDFEFPQ EEFDDKQFQK AQAISVLHEM
HuALFC      CDLPQTHSLG NRRALILLGQ MGRISPFSCL KDRHDFRIPQ EEFDGNQFQK AQAISVLHEM
HuALFD      CDLPETHSLD NRRTLMLLAQ MSRISPSSCL MDRHDFGFPQ EEFDGNQFQK APAISVLHEL
HuALFF      CDLPQTHSLG NRRALILLAQ MGRISPFSCL KDRHDFGFPQ EEFDGNQFQK AQAISVLHEM
HuALFG      CDLPQTHSLS NRRTLMIMAQ MGRISPFSCL KDRHDFGFPQ EEFDGNQFQK AQAISVLHEM
HuALFH      CNLSQTHSLN NRRTLMLMAQ MRRISPFSCL KDRHDFEFPQ EEFDGNQFQK AQAISVLHEM
HuALFI      CDLPQTHSLG NRRALILLAQ MGRISPFSCL KDRPDFGLPQ EEFDGNQFQK TQAISVLHEM
HuALFJ      CDLPQTHSLR NRRALILLAQ MGRISPFSCL KDRHEFRFPE EEFDGHQFQK TQAISVLHEM
HuALFK      CDLPQTHSLG HRRTMMLLAQ MRRISLFSCL KDRHDFRFPQ EEFDGNQFQK AEAISVLHEV
HuALFL      CDLPQTHTLR NRRALILLGQ MGRISPFSCL KDRHDFRIPQ EEFDGNQFQK AQAISVLHEM
HuALFN      CDLPQTHSLG NRRALILLAQ MGRISHFSCL KDRYDFGFPQ EVFDGNQFQK AQAISAFHEM
HuOMEGA1    CDLPQNHGLL SRNTLVLLHQ MRRISPFLCL KDRRDFRFPQ EMVKGSQLQK AHVMSVLHEM
BoALF4      CDLSPNHVLV GRQNLRLLGQ MRRLSPRFCL QDRKDFAFPQ EMVEVSQFQE AQAISVLHEM
EqOMEGA1    CDLPASLDLR KQETLRVLHQ METISPPSCL KHRTDFRFPQ EQLDGRQFPE AQATSVLQEM
EqOMEGA2    CDLPQNHILV SRKNFVLLGQ MSRISSAICL KDRKDFRFPQ DMADGRQFPE AQAASVLHEM
EqBETA  VNY DLLRSQLRSS NSACLMLLRQ L-NGAPQRCP EDTMNFQVPE EIEQAQQFQK EDAALVIYEM
HuBETA  MSY NLLGFLQRSS NFQCQKLLWQ L-NGRLEYCL KDRMNFDIPE EIKQLQQFQK EDAALTIYEM
BoBETA1 RSY SLLRFQQRQS LKECQKLLGQ L-PSTSQHCL EARMDFQMPE EMKQEQQFQK EDAILVMYEV
MuBETA  INY KQLQLQERTN IRKCQELLEQ L-NGKI--NL TYRADFKIPM EMTE-KM-QK SYTAFAIQEM
```

FIG.36A

```
                     70         80         90        100        110        120
EqALF1    IQQIFHLFST DGSSAAWDES LLDKLYTGLY QQLTELEACL SQEVGVEETP LMNEDSLLAV
EqALF2    IQQIFHLFST DGSSAAWDES LLDKLYTGLY QQLTELEACL SQEVGVEETP LMNEDSLLAV
CaALF1    TQKVFHLFCP DTSSAPWNMT LLEELCSGLS EQLDDLEACP LQEAGLAETP LMHEDSTL--
BoALF1    TQHTFQLFST EGSAAVWDES LLDRLRTALD QQLTDLQACL RQEEGLPGAP LLKEDSSLAV
BoALF2    TQHTFQLFST EGSAAVWDQS LLDKLRAALD QQLTDLQACL RQEEGLRGAP LLKEDASLAV
BoALF3    TQHTFQLFST EGSATMWDES LLDKLRDALD QQLTDLQFCL RQEEELQGAP LLKEDSSLAV
BoALFA    TQHTFQLFST EGSPATWDKS LLDKLRAALD QQLTDLQACL TQEEGLRGAP LLKEDSSLAV
BoALFB    TQHTFQLFST EGSATTWDES LLDKLHAALD QQLTDLQACL RQEEGLRGAP LLKEGSSLAV
BoALFC    TQHTFQLFST EGSATMWDES LLDKLRDALD QQLTDLQFCL PQEEELQGAP LLKEDSSLAV
BoALFD    TQHTFQLSST EGSAAVWDES LLDKLRTALD QQLTDLQACL RQEEGLPGAP LLKEDSSLAV
MuALFA    TQQVLNIFTS KDSSAAWDAS LLDSFCNDLH QQLNDLKACV MQEVGVQEPP LTQEDYLLAV
MuALF1    TQQILNIFTS KDSSAAWNAT LLDSFCNDLH QQLNDLQGCL MQQVGVQEFP LTQEDALLAV
MuALF2    TQQTLNLFTS KASSAAWNAT LLDSFCNDLH QQLNDLQTCL MQQVGVQEPP LTQEDALLAV
MuALF4    TQQILNLFTS KDLSATWNAT LLDSFCNDLH QQLNDLKACV MQ-----EPP LTQEDSLLAV
MuALF5    TQQVLNIFTS KDSSAAWNAT LLDSFCNEVH QQLNDLKACV MQQVGVQESP LTQEDSLLAV
MuALF6    TQQILTLFTS KDSSAAWNAT LLDSFCNDLH QLLNDLQGCL MQQVEIQALP LTQEDSLLAV
MuALF6a   TQQILNIFTS KDSSAAWDAT LLDTFCNDLY QQLNDLQACL VQQVRLQEPP LTQEVSLLAV
RaALF     TQQILSLFTS KESSTAWDAT LLDSFCNDLQ QQLSGLQACL MQQVGVQESP LTQEDSLLAV
HuALFA    IQQIFNLFST KDSSAAWDET LLDKFYTELY QQLNDLEACV IQGVGVTETP LMKEDSILAV
HuALFB    IQQTFNLFST KDSSAALDET LLDEFYIELD QQLNDLEVLC DQEVGVIESP LMYEDSILAV
HuALFC    IQQTFNLFST EDSSAAWEQS LLEKFSTELY QQLNDLEACV IQEVGVEETP LMNEDSILAV
HuALFD    IQQIFNLFTT KDSSAAWDED LLDKFCTELY QQLNDLEACV MQEERVGETP LMNVDSILAV
HuALFF    IQQTFNLFST KDSSATWEQS LLEKFSTELN QQLNDMEACV IQEVGVEETP LMNVDSILAV
HuALFG    IQQTFNLFST KDSSATWDET LLDKFYTELY QQLNDLEACM MQEVGVEDTP LMNVDSILTV
HuALFH    MQQTFNLFST KNSSAAWDET LLEKFYIELF QQMNDLEACV IQEVGVEETP LMNEDSILAV
HuALFI    IQQTFNLFST EDSSAAWEQS LLEKFSTELY QQLNNLEACV IQEVGMEETP LMNEDSILAV
HuALFJ    IQQTFNLFST EDSSAAWEQS LLEKFSTELY QQLNDLEACV IQEVGVKETP LMNEDFILAV
HuALFK    IQQTFNLFST KDSSVAWDER LLDKLYTELY QQLNDLEACV MQEVWVGGTP LMNEDSILAV
HuALFL    IQQTFNLFST EDSSAAWEQS LLELFSTELY QQLNPLEACV IQEVGVEETP LMNEDSILAV
HuALFN    IQQTFNLFST KDSSAAWDET LLDKFYIELF QQLNDLEACV TQEVGVEEIA LMNEDSILAV
HuOMEGA1  LQQIFSLFHT ERSSAAWNMT LLDQLHTGLH QQLQHLETCL LQVVGEGESA GAISSPALTL
BoALF4    LQQSFNLFHK ERSSAAWDTT LLEQLLTGLH QQLDDLDACL GLLTGEEDSA LGRTGPTLAM
EqOMEGA1  LQQIVSLFHT ERSSAAWNTT LLDRLLAGLH QQLEDLNTCL DEQTGEEESA LGTVGPTLAV
EqOMEGA2  LQQIFSLFHT ERSSAAWNTT LLDELCTGLL RQLEDLDTCL EQEMGEEESA LGTVRPTLAV
EqBETA    LQHTWRIFRR NFASTGWNET IVKNLLVEVH LQMDRLETNL EEIMEEESST WGNTTI-LRL
HuBETA    LQNIFAIFRQ DSSSTGWNET IVENLLANVY HQINHLKTVL EEKLEKEDFT RGKLMSSLHL
BoBETA1   LQHIFGILTR DFSSTGWSET IIEDLLKELY WQMNRLQPIQ KEIMQKQNST TEDTIV-PHL
MuBETA    LQNVFLVFRN NFSSTGWNET IVVRLLDELH QQTVFLKTVL EEKQE-ERLT WEMSSTALHL
```

FIG.36B

|          | 130        | 140        | 150        | 160        | 170    |
|----------|------------|------------|------------|------------|--------|
| EqALF1   | RRYFQRIALY | LQEKKYSPCA | WEIVRAEIMR | SFSSSTNLPQ | S      |
| EqALF2   | RRYFQRIALY | LQEKKYSPCA | WEIVRAEIMR | CFSSSTNLQQ | S      |
| CaALF1   | RTYFQRISLY | LQDRNHSPCA | WEMVRAEIGR | SFFSSTILQE | RIRRRK |
| BoALF1   | RKYFHRLTLY | LQEKRHSPCA | WEVVRAQVMR | AFSSSTNLQE | RFRRKD |
| BoALF2   | RKYFHRLTLY | LQEKRHSPCA | WEVVRAEVMR | AFSSSTNLQE | KFRRKD |
| BoALF3   | RKYFHRLTLY | LQEKRHSPCA | WEVVRAQVMR | AFSSSTNLQE | SFRRKD |
| BoALFA   | RKYFHRLTLY | LQEKRHSPCA | WEVVRAEVMR | AFSSSTNLQE | SFRRKD |
| BoALFB   | RKYFHRLTLY | LQEKRHSPCA | WEVVRAEVMR | AFSSSTNLQE | KFRRKD |
| BoALFC   | RKYFHRLTLY | LGEKRHSPCA | WEVVRAQVMR | AFSSSTNLQE | SFRRKD |
| BoALFD   | RKYFHRLTLY | LQEKRHSPCA | WEVVRAQVMR | AFSSSTNLQE | RFRRKD |
| MuALFA   | RTYFHRITVY | LREKKHSPCA | WEVVRAEVWR | AMSSSAKLLA | RLSEEKE |
| MuALF1   | RKYFHRITVY | LREKKHSPCA | WEVVRAEVWR | ALSSSANVLG | RLREEK |
| MuALF2   | RKYFHRITVY | LREKKHSPCA | WEVVRAEVWR | ALSSSVNLLP | RLSEEKE |
| MuALF4   | RTYFHRITVY | LRKKKHSLCA | WEVIRAEVWR | ALSSSTNLLA | RLSEEKE |
| MuALF5   | RKYFHRITVY | LREKKHSPCA | WEVVRAEVWR | ALSSSVNLLA | RLSKEE |
| MuALF6   | RTYFHRITVF | LREKKHSPCA | WEVVRAEVWR | ALSSSAKLLA | RLNEDE |
| MuALF6a  | RKYFHRITVY | LREKKHSPCA | WEVVRAEVWR | ALSSSANVLG | RLREEK |
| RaALF    | REYFHRITVY | LRENKHSPCA | WEVVKAEVWR | ALSSSANLMG | RLREERNES |
| HuALFA   | RKYFQRITLY | LKEKKYSPCA | WEVVRAEIMR | SFSLSTNLQE | SLRSKE |
| HuALFB   | RKYFQRITLY | LTEKKYSSCA | WEVVRAEIMR | SFSLSINLQK | RLKSKE |
| HuALFC   | RKYFQRITLY | LIERKYSPCA | WEVVRAEIMR | SLSFSTNLQK | RLRRKD |
| HuALFD   | KKYFRRITLY | LTEKKYSPCA | WEVVRAEIMR | SLSLSTNLQE | RLRRKE |
| HuALFF   | KKYFQRITLY | LTEKKYSPCA | WEVVRAEIMR | SFSLSKIFQE | RLRRKE |
| HuALFG   | RKYFQRITLY | LTEKKYSPCA | WEVVRAEIMR | SFSLSANLQE | RLRRKE |
| HuALFH   | KKYFQRITLY | LMEKKYSPCA | WEVVRAEIMR | SFSFSTNLQK | RLRRKD |
| HuALFI   | RKYFQRITLY | LTEKKYSPCA | WEVVRAEIMR | SLSFSTNLQK | ILRRKD |
| HuALFJ   | RKYFQRITLY | LMEKKYSPCA | WEVVRAEIMR | SFSFSTNLKK | GLRRKD |
| HuALFK   | RKYFQRITLY | LTEKKYSPCA | WEVVRAEIMR | SFSSSRNLQE | RLRRKE |
| HuALFL   | RKYFQRITLY | LIERKYSPCA | NEVVRAEIMR | SLSFSTNLQK | RLRRKD |
| HuALFN   | RKYFQRITLY | LMGKKYSPCA | WEVVRAEIMR | SFSFSTNLQK | GLRRKD |
| HuOMEGA1 | RRYFQGIRVY | LKEKKYSDCA | WEVVRMEIMK | SLFLSTNMQE | RLRSKDRDLG SS |
| BoALF4   | KRYFQGIHVY | LQEKGYSDCA | WEIVRLEIMR | SLSSSTSLQE | RLRMMDGDLK SP |
| EqOMEGA1 | KRYFRRIRLY | LTEKKYSDCA | WEIVRVDIMR | SFSSSANLQG | RLGMKDGDLG SP |
| EqOMEGA2 | KRYFRGIHLY | LKEKKYSDCA | WEIVRMEIMR | SFSSSANLQG | RLRMKDSDLG SP |
| EqBETA   | KKYYGRISQY | LKAKKYSHCA | WTVVQAEMLR | NLAFLNGLTD | YLQN |
| HuBETA   | KRYYGRILHY | LKAKEYSHCA | WTIVRVEILR | NFYFINRLTG | YLRN |
| BoBETA1  | GKYYFNLMQY | LESKEYDRCA | WTVVQVQILT | NVSFLMRLTG | YVRD |
| MuBETA   | KSYYWRVQRY | LKLMKYNSYA | WMVVRAEIFR | NFLIIRRLTR | NFQN |

FIG.36C

```
  1                   5                        10                       15
Cys Asp Leu Pro Gln Asn His Ile Leu Val Ser Arg Lys Asn Phe
TGT GAC CTG CCT CAG AAC CAC ATC CTG GTT AGC AGG AAG AAC TTC
                     20                       25                       30
Val Leu Leu Gly Gln Met Ser Arg Ile Ser Ser Ala Ile Cys Leu
GTG CTT CTG GGC CAA ATG AGC AGA ATC TCC TCC GCA ATC TGT CTG
                     35                       40                       45
Lys Asp Arg Lys Asp Phe Arg Phe Pro Gln Asp Met Ala Asp Gly
AAG GAC AGA AAA GAC TTC AGG TTC CCC CAG GAC ATG GCG GAT GGC
                     50                       55                       60
Arg Gln Phe Pro Glu Ala Gln Ala Ala Ser Val Leu His Glu Met
AGG CAG TTC CCA GAG GCC CAG GCC GCG TCT GTC CTC CAC GAG ATG
                     65                       70                       75
Leu Gln Gln Ile Phe Ser Leu Phe His Thr Glu Arg Ser Ser Ala
CTC CAG CAG ATC TTC AGC CTC TTC CAC ACA GAG CGC TCG TCT GCT
                     80                       85                       90
Ala Trp Asn Thr Thr Leu Leu Asp Glu Leu Cys Thr Gly Leu Leu
GCC TGG AAC ACG ACC CTC CTG GAC GAA CTC TGC ACG GGA CTC CTT
                     95                      100                      105
Arg Gln Leu Glu Asp Leu Asp Thr Cys Leu Glu Gln Glu Met Gly
CGG CAG CTG GAA GAC CTG GAC ACC TGT TTG GAG CAG GAG ATG GGA
                    110                      115                      120
Glu Glu Glu Ser Ala Leu Gly Thr Val Arg Pro Thr Leu Ala Val
GAG GAA GAA TCT GCC CTG GGA ACT GTG CGC CCT ACA CTG GCC GTG
                    125                      130                      135
Lys Arg Tyr Phe Arg Gly Ile His Leu Tyr Leu Lys Glu Lys Lys
AAG AGG TAC TTC CGG GGG ATC CAT CTC TAC CTG AAA GAG AAG AAA
                    140                      145                      150
Tyr Ser Asp Cys Ala Trp Glu Ile Val Arg Met Glu Ile Met Arg
TAC AGT GAC TGT GCC TGG GAG ATT GTC CGA ATG GAA ATC ATG AGA
                    155                      160                      165
Ser Phe Ser Ser Ser Ala Asn Leu Gln Gly Arg Leu Arg Met Lys
TCC TTC TCT TCA TCA GCA AAC CTG CAA GGA AGG TTA AGA ATG AAG
                    170
Asp Gly Asp Leu Gly Ser Pro  *
GAT GGA GAC CTG GGC TCA CCT TGA
```

FIG.37

```
  1                   5                        10                      15
Cys Asp Leu Pro His Thr His Ser Leu Gly Asn Thr Arg Val Leu
TGT GAC CTG CCT CAC ACC CAT AGC CTG GGC AAC ACA AGG GTC TTG
                    20                       25                       30
Met Leu Leu Gly Gln Met Arg Arg Ile Ser Pro Phe Ser Cys Leu
ATG CTC CTG GGA CAA ATG AGG AGA ATC TCC CCC TTC TCC TGC CTG
                    35                       40                       45
Lys Asp Arg Asn Asp Phe Gly Phe Pro Gln Glu Val Phe Asp Gly
AAG GAC AGA AAT GAC TTT GGA TTC CCC CAG GAG GTG TTT GAC GGC
                    50                       55                       60
Asn Gln Phe Arg Lys Pro Gln Ala Ile Ser Ala Val His Glu Thr
AAC CAG TTC CGG AAG CCT CAA GCC ATC TCT GCG GTC CAT GAG ACG
                    65                       70                       75
Ile Gln Gln Ile Phe His Leu Phe Ser Thr Asp Gly Ser Ser Ala
ATC CAA CAG ATC TTC CAC CTC TTC AGC ACA GAC GGC TCG TCT GCT
                    80                       85                       90
Ala Trp Asp Glu Ser Leu Leu Asp Lys Leu Tyr Thr Gly Leu Tyr
GCC TGG GAC GAG AGC CTC CTA GAC AAG CTC TAC ACT GGA CTC TAT
                    95                      100                      105
Gln Gln Leu Thr Glu Leu Glu Ala Cys Leu Ser Gln Glu Val Gly
CAG CAG CTG ACT GAG CTG GAA GCC TGT CTG AGC CAG GAG GTG GGG
                   110                      115                      120
Val Glu Glu Thr Pro Leu Met Asn Glu Asp Ser Leu Leu Ala Val
GTG GAA GAG ACG CCC CTG ATG AAC GAG GAC TCC CTG CTG GCT GTG
                   125                      130                      135
Arg Arg Tyr Phe Gln Arg Ile Ala Leu Tyr Leu Gln Glu Lys Lys
AGG AGA TAC TTC CAA AGA ATC GCT CTC TAT CTG CAA GAG AAG AAA
                   140                      145                      150
Tyr Ser Pro Cys Ala Trp Glu Ile Val Arg Ala Glu Ile Met Arg
TAC AGC CCT TGT GCC TGG GAG ATC GTC AGA GCA GAA ATC ATG AGA
                   155                      160
Ser Phe Ser Ser Ser Thr Asn Leu Pro Gln Ser  *
TCC TTC TCT TCA TCC ACA AAC TTG CCG CAG AGT TAA
```

FIG. 38

```
  1                  5                      10                     15
Cys Asp Leu Pro His Thr His Ser Leu Gly Asn Thr Arg Val Leu
TGT GAC CTG CCT CAC ACC CAT AGC CTG GGC AAC ACA AGG GTC TTG
                    20                     25                     30
Met Leu Leu Gly Gln Met Arg Arg Ile Ser Pro Phe Ser Cys Leu
ATG CTC CTG GGA CAA ATG AGG AGA ATC TCC CCC TTC TCC TGC CTG
                    35                     40                     45
Lys Asp Arg Asn Asp Phe Gly Phe Pro Gln Glu Val Phe Asp Gly
AAG GAC AGA AAT GAC TTT GGA TTC CCC CAG GAG GTG TTT GAC GGC
                    50                     55                     60
Asn Gln Phe Arg Lys Pro Gln Ala Ile Ser Ala Val His Glu Thr
AAC CAG TTC CGG AAG CCT CAA GCC ATC TCC GCG GTC CAT GAG ACT
                    65                     70                     75
Ile Gln Gln Ile Phe His Leu Phe Ser Thr Asp Gly Ser Ser Ala
ATC CAA CAG ATC TTC CAC CTC TTC AGC ACA GAC GGC TCG TCT GCC
                    80                     85                     90
Ala Trp Asp Glu Ser Leu Leu Asp Lys Leu Tyr Thr Gly Leu Tyr
GCC TGG GAC GAG AGC CTC CTA GAC AAG CTC TAC ACT GGA CTC TAT
                    95                     100                    105
Gln Gln Leu Thr Glu Leu Glu Ala Cys Leu Ser Gln Glu Val Gly
CAG CAG CTG ACT GAG CTG GAA GCC TGT CTG AGC CAG GAG GTG GGG
                    110                    115                    120
Val Glu Glu Thr Pro Leu Met Asn Glu Asp Ser Leu Leu Ala Val
GTG GAA GAG ACG CCC CTG ATG AAC GAG GAC TCC CTG CTG GCT GTG
                    125                    130                    135
Arg Arg Tyr Phe Gln Arg Ile Thr Leu Tyr Leu Gln Glu Lys Lys
AGG AGA TAC TTC CAA AGA ATC ACT CTC TAT CTG CAA GAG AAG AAA
                    140                    145                    150
Tyr Ser Pro Cys Ala Trp Glu Ile Val Arg Ala Glu Ile Met Arg
TAC AGC CCT TGT GCC TGG GAG ATC GTC AGA GCA GAA ATC ATG AGA
                    155                    160
Ser Phe Ser Ser Ser Thr Asn Leu Pro Gln Ser  *
TCC TTC TCT TCA TCC ACA AAC TTG CCG CAA AGT TAA
```

FIG.39

RECOMBINANT PRODUCTION OF DOG AND HORSE TYPE I INTERFERONS

This application is a division of application Ser. No. 08/302,391, filed Sep. 8, 1994, now U.S. Pat. No. 5,605,688, which is a continuation of application Ser. No. 07/851,691, filed Mar. 13, 1992, abandoned, which is a division of application Ser. No. 07/005,300, filed Dec. 17, 1986, abandoned, which is a continuation of 06/810,377, filed Dec. 18, 1985, abandoned.

The present invention relates to a process for preparing recombinant horse and dog interferons and the interferons themselves.

Interferons are proteins which are secreted by eukaryotic cells after virus infection or other stimulation and which may in turn protect the cells from virus infections. At present, four classes of interferons are known; they are referred to as alpha-interferon, beta-interferon, omega-interferon and gamma-interferon (abreviated to IFN-α, IFN-β, IFN-ω, and IFN-γ). They differ in their structure and in their effects. Thus, interferons may have a regulatory effect on the cells of the immune system or they may influence the differentiation of cells and the growth of tumours.

For a long time it had been assumed that interferons have a species-specific activity. However, in vitro tests show that IFN preparations from cattle may have an antiviral activity in monkeys and in humans (32). This inter-species activity is possibly connected to the greater or lesser degree of homology of the genes or proteins; owing to the small quantities of animal interferons this assumption could not be checked.

In spite of the inter-species activity found, side effects such as antigeneities could be expected when using inter-ferons from different species, which are not acceptable for therapy.

However, since on the other hand the keeping of agricultural and domestic animals constitutes a manor economic factor, there is a need for interferons for the different species which can be used by veterinary surgeons.

Furthermore, highly purified animal interferon from the various species would present the welcome opportunity to investigate the mechanisms of activity of interferons in order to arrive at models which could be applied to humans.

The first investigations with animal interferons were carried out with preparations from natural cell material; the yield and purity of the interferons prepared by this process render them unsuitable for the preparation of pharmaceutical compositions.

As a result of the development of the recombinant DNA technology it is possible to induce microorganisms to produce heterologous proteins. Human interferons (HU-IFN) were also prepared by this method; most recently, a cattle α-interferon and a cattle β-interferon have also been prepared.

The present invention relates to new horse and dog interferons (EqIFN and CaIFN) and their optionally N-glycosylated derivatives.

The invention further relates to the gene sequences coding for these interferons and recombinant molecules which contain these sequences, expression vectors such as plasmids containing the sequences as inserts and various host organisms or cultures which permit the preparation of the horse interferons.

The invention particularly relates to the horse interferons and the sequences of the following formulae which code for them:

Formula I

| 1 | | | | 5 | | | | | 10 | | | | | 15 |
|---|---|---|---|---|---|---|---|---|---|---|---|---|---|---|
| Cys | Asp | Leu | Pro | His | Thr | His | Ser | Leu | Gly | Asn | Thr | Arg | Val | Leu |
| TGT | GAC | CTG | CCT | CAC | ACC | CAT | AGC | CTG | GGC | AAC | ACA | AGG | GTC | TTG |
| | | | | 20 | | | | | 25 | | | | | 30 |
| Met | Leu | Leu | Gly | Gln | Met | Arg | Arg | Ile | Ser | Pro | Phe | Ser | Cys | Leu |
| ATG | CTC | CTG | GGG | CAA | ATG | AGG | AGA | ATC | TCC | CCC | TTC | TCC | TGC | CTG |
| | | | | 35 | | | | | 40 | | | | | 45 |
| Lys | Asp | Arg | Asn | Asp | Phe | Gly | Phe | Pro | Gln | Glu | Val | Phe | Asp | Gly |
| AAG | GAC | AGA | AAT | GAC | TTT | GGA | TTC | CCC | CAG | GAG | GTG | TTT | GAC | GGC |
| | | | | 50 | | | | | 55 | | | | | 60 |
| Asn | Gln | Phe | Arg | Lys | Pro | Gln | Ala | Ile | Ser | Ala | Val | His | Glu | Thr |
| AAC | CAG | TTC | CGG | AAG | CCT | CAA | GCC | ATC | TCT | GCG | GTC | CAT | GAG | ACG |
| | | | | 65 | | | | | 70 | | | | | 75 |
| Ile | Gln | Gln | Ile | Phe | His | Leu | Phe | Ser | Thr | Asp | Gly | Ser | Ser | Ala |
| ATC | CAA | CAG | ATC | TTC | CAC | CTC | TTC | AGC | ACA | GAC | GGC | TCG | TCT | GCC |
| | | | | 80 | | | | | 85 | | | | | 90 |
| Ala | Trp | Asp | Glu | Ser | Leu | Leu | Asp | Lys | Leu | Tyr | Thr | Gly | Leu | Tyr |
| GCC | TGG | GAC | GAG | AGC | CTC | CTA | GAC | AAA | CTC | TAC | ACT | GGA | CTC | TAT |
| | | | | 95 | | | | | 100 | | | | | 105 |
| Gln | Gln | Leu | Thr | Glu | Leu | Glu | Ala | Cys | Leu | Ser | Gln | Glu | Val | Gly |
| CAG | CAG | CTG | ACT | GAG | CTG | GAA | GCC | TGT | CTG | AGC | CAG | GAG | GTG | GGG |
| | | | | 110 | | | | | 115 | | | | | 120 |
| Val | Glu | Glu | Thr | Pro | Leu | Met | Asn | Glu | Asp | Ser | Leu | Leu | Ala | Val |
| GTG | GAA | GAG | ACG | CCC | CTG | ATG | AAC | GAG | GAC | TCC | CTG | CTG | GCT | GTG |
| | | | | 125 | | | | | 130 | | | | | 135 |
| Arg | Arg | Tyr | Phe | Gln | Arg | Ile | Ala | Leu | Tyr | Leu | Gln | Glu | Lys | Lys |
| AGG | AGA | TAC | TTC | CAA | AGA | ATC | GTC | CTC | TAT | CTG | CAA | GAG | AAG | AAA |

-continued
Formula I

| | | | | 140 | | | | | 145 | | | | | 150 |
|---|---|---|---|---|---|---|---|---|---|---|---|---|---|---|
| Tyr | Ser | Pro | Cys | Ala | Trp | Glu | Ile | Val | Arg | Ala | Glu | Ile | Met | Arg |
| TAC | AGC | CCT | TGT | GCC | TGG | GAG | ATC | GTC | AGA | GCA | GAA | ATC | ATG | AGA |
| | | | | 155 | | | | | 160 | | | | | 165 |
| Ser | Phe | Ser | Ser | Ser | Thr | Asn | Leu | Pro | Gln | Ser | + | | | |
| TCC | TTC | TCT | TCA | TCC | ACA | AAC | TTG | CCG | CAG | AGT | TAA, | | | |

Formula II

| 1 | | | | 5 | | | | | 10 | | | | | 15 |
|---|---|---|---|---|---|---|---|---|---|---|---|---|---|---|
| Cys | Asp | Leu | Pro | His | Thr | His | Ser | Leu | Gly | Asn | Thr | Arg | Val | Leu |
| TGT | GAC | CTG | CCT | CAC | ACC | CAT | AGC | CTG | GGC | AAC | ACA | AGG | GTC | TTG |
| | | | | 20 | | | | | 25 | | | | | 30 |
| Met | Leu | Leu | Gly | Gln | Met | Arg | Arg | Ile | Ser | Pro | Phe | Ser | Cys | Leu |
| ATG | CTC | CTG | GGA | CAA | ATG | AGG | AGA | ATC | TCC | CCC | TTC | TCC | TGC | CTG |
| | | | | 35 | | | | | 40 | | | | | 45 |
| Lys | Asp | Arg | Asn | Asp | Phe | Gly | Phe | Pro | Gln | Glu | Val | Phe | Asp | Gly |
| AAG | GAC | AGA | AAT | GAC | TTT | GGA | TTC | CCC | CAG | GAG | GTG | TTT | GAC | GGC |
| | | | | 50 | | | | | 55 | | | | | 60 |
| Asn | Gln | Phe | Arg | Lys | Pro | Gln | Ala | Ile | Ser | Ala | Val | His | Glu | Thr |
| AAC | CAG | TTC | CGG | AAG | CCT | CAA | GCC | ATC | TCC | GCG | GTC | CAT | GAG | ACG |
| | | | | 65 | | | | | 70 | | | | | 75 |
| Ile | Gln | Gln | Ile | Phe | His | Leu | Phe | Ser | Thr | Asp | Gly | Ser | Ser | Ala |
| ATC | CAA | CAG | ATC | TTC | CAC | CTC | TTC | AGC | ACA | GAC | GGC | TCG | TCT | GCT |
| | | | | 80 | | | | | 85 | | | | | 90 |
| Ala | Trp | Asp | Glu | Ser | Leu | Leu | Asp | Lys | Leu | Tyr | Thr | Gly | Leu | Tyr |
| GCC | TGG | GAC | GAG | AGC | CTC | CTA | GAC | AAG | CTC | TAC | ACT | GGA | CTC | TAT |
| | | | | 95 | | | | | 100 | | | | | 105 |
| Gln | Gln | Leu | Thr | Glu | Leu | Glu | Ala | Cys | Leu | Ser | Gln | Glu | Val | Gly |
| CAG | CAG | CTG | ACT | GAG | CTG | GAA | GCC | TGT | CTG | AGC | CAG | GAG | GTG | GGG |
| | | | | 110 | | | | | 115 | | | | | 120 |
| Val | Glu | Glu | Thr | Pro | Leu | Met | Asn | Glu | Asp | Ser | Leu | Leu | Ala | Val |
| GTG | GAA | GAG | ACG | CCC | CTG | ATG | AAC | GAG | GAC | TCC | CTG | CTG | GCT | GTG |
| | | | | 125 | | | | | 130 | | | | | 135 |
| Arg | Arg | Tyr | Phe | Gln | Arg | Ile | Ala | Leu | Tyr | Leu | Gln | Glu | Lys | Lys |
| AGG | AGA | TAC | TTC | CAA | AGA | ATC | GTC | CTC | TAT | CTG | CAA | GAG | AAG | AAA |
| | | | | 140 | | | | | 145 | | | | | 150 |
| Tyr | Ser | Pro | Cys | Ala | Trp | Glu | Ile | Val | Arg | Ala | Glu | Ile | Met | Arg |
| TAC | AGC | CCT | TGT | GCC | TGG | GAG | ATC | GTC | AGA | GCA | GAA | ATC | ATG | AGA |
| | | | | 155 | | | | | 160 | | | | | 165 |
| Cys | Phe | Ser | Ser | Ser | Thr | Asn | Leu | Gln | Gln | Ser | + | | | |
| TGC | TTC | TCT | TCA | TCC | ACA | AAC | TTG | CAG | CAG | AGT | TAA, | | | |

Formula III

| | | | | 5 | | | | | 10 | | | | | 15 |
|---|---|---|---|---|---|---|---|---|---|---|---|---|---|---|
| Val | Asn | Tyr | Asp | Leu | Leu | Arg | Ser | Gln | Leu | Arg | Ser | Ser | Asn | Ser |
| GTG | AAC | TAT | GAC | TTG | CTT | CGG | TCC | CAA | CTA | AGA | AGC | AGC | AAT | TCA |
| | | | | 20 | | | | | 25 | | | | | 30 |
| Ala | Cys | Leu | Met | Leu | Leu | Arg | Gln | Leu | Asn | Gly | Ala | Pro | Gln | Arg |
| GCA | TGT | CTG | ATG | CTC | CTG | CGG | CAG | TTG | AAT | GGA | GCC | CCT | CAA | CGT |
| | | | | 35 | | | | | 40 | | | | | 45 |
| Cys | Pro | Glu | Asp | Thr | Met | Asn | Phe | Gln | Val | Pro | Glu | Glu | Ile | Glu |
| TGC | CCC | GAG | GAC | ACA | ATG | AAC | TTC | CAG | GTC | CCT | GAG | GAG | ATT | GAG |
| | | | | 50 | | | | | 55 | | | | | 60 |
| Gln | Ala | Gln | Gln | Phe | Gln | Lys | Glu | Asp | Ala | Ala | Leu | Val | Ile | Tyr |
| CAA | GCA | CAG | CAG | TTC | CAG | AAG | GAG | GAT | GCT | GCA | TTG | GTC | ATC | TAT |

-continued
Formula III

```
                              65                          70                          75
Glu   Met   Leu   Gln   His   Thr   Trp   Arg   Ile   Phe   Arg   Arg   Asn   Phe   Ala
GAG   ATG   CTC   CAG   CAC   ACC   TGG   CGT   ATT   TTC   AGA   AGA   AAT   TTC   GCT 80                          85                          90
Ser   Thr   Gly   Trp   Asn   Glu   Thr   Ile   Val   Cys   Asn   Leu   Leu   Val   Glu
AGC   ACT   GGC   TGG   AAT   GAG   ACC   ATC   GTT   AAG   AAC   CTC   CTT   GTG   GAA 95                          100                         105
Val   His   Leu   Gln   Met   Asp   Arg   Leu   Glu   Thr   Asn   Leu   Glu   Glu   Ile
GTC   CAT   CTG   CAG   ATG   GAC   CGT   CTG   GAG   ACA   AAC   CTG   GAG   GAA   ATA 110                         115                         120
Met   Glu   Glu   Glu   Ser   Ser   Thr   Trp   Gly   Asn   Thr   Thr   Ile   Leu   Arg
ATG   GAG   GAG   GAA   AGC   TCC   ACC   TGG   GGA   AAC   ACA   ACC   ATT   CTG   CGC 125                         130                         135
Leu   Lys   Lys   Tyr   Tyr   Gly   Arg   Ile   Ser   Gln   Tyr   Leu   Lys   Ala   Lys
CTG   AAG   AAA   TAC   TAC   GGA   AGG   ATC   TCG   CAG   TAC   CTG   AAG   GCC   AAG 140                         145                         150
Lys   Tyr   Ser   His   Cys   Ala   Trp   Thr   Val   Val   Gln   Ala   Glu   Met   Leu
AAG   TAC   AGC   CAC   TGT   GCC   TGG   ACA   GTG   GTC   CAA   GCG   GAA   ATG   CTC 155                         160                         165
Arg   Asn   Leu   Ala   Phe   Leu   Asn   Gly   Leu   Thr   Asp   Tyr   Leu   Gln   Asn +
AGG   AAC   TTG   GCC   TTC   CTT   AAC   GGA   CTC   ACA   GAT   TAC   CTC   CAA   AAC

TGA
and
```

Formula IV

```
  1                           5                           10                          15
Cys   Asp   Leu   Pro   Ala   Ser   Leu   Asp   Leu   Arg   Lys   Gln   Glu   Thr   Leu
TGC   GAC   CTG   CCT   GCG   AGC   CTT   GAC   TTG   AGA   AAG   CAG   GAG   ACC   CTC 20                          25                          30
Arg   Val   Leu   His   Gln   Met   Glu   Thr   Ile   Ser   Pro   Pro   Ser   Cys   Leu
AGA   GTT   CTG   CAC   CAG   ATG   GAG   ACA   ATC   TCT   CCT   CCT   TCC   TGT   CTG 35                          40                          45
Lys   His   Arg   Thr   Asp   Phe   Arg   Phe   Pro   Gln   Glu   Gln   Leu   Asp   Gly
AAG   CAC   AGG   ACA   GAC   TTC   AGG   TTC   CCC   CAG   GAG   CAG   CTG   GAT   GGC 50                          55                          60
Arg   Gln   Phe   Pro   Glu   Ala   Gln   Ala   Thr   Ser   Val   Leu   Gln   Glu   Met
AGG   CAG   TTC   CCA   GAG   GCC   CAG   GCC   ACG   TCT   GTC   CTC   CAG   GAG   ATG 65                          70                          75
Leu   Gln   Gln   Ile   Val   Ser   Leu   Phe   His   Thr   Glu   Arg   Ser   Ser   Ala
CTC   CAG   CAG   ATC   GTC   AGC   CTC   TTC   CAC   ACA   GAG   CGC   TCG   TCT   GCT 80                          85                          90
Ala   Trp   Asn   Thr   Thr   Leu   Leu   Asp   Arg   Leu   Leu   Ala   Gly   Leu   His
GCC   TGG   AAC   ACG   ACT   CTG   CTG   GAC   CGA   CTC   CTC   GCG   GGA   CTC   CAT 95                          100                         105
Gln   Gln   Leu   Glu   Asp   Leu   Asn   Thr   Cys   Leu   Asp   Glu   Gln   Thr   Gly
CAG   CAG   CTG   GAA   GAC   CTC   AAC   ACC   TGC   TTG   GAT   GAG   CAG   ACA   GGA 110                         115                         120
Glu   Glu   Glu   Ser   Ala   Leu   Gly   Thr   Val   Gly   Pro   Thr   Leu   Ala   Val
GAG   GAA   GAA   TCC   GCC   CTG   GGA   ACT   GTG   GGC   CCT   ACA   CTG   GCC   GTG 125                         130                         135
Lys   Arg   Tyr   Phe   Arg   Arg   Ile   Arg   Leu   Tyr   Leu   Thr   Glu   Lys   Lys
AAG   AGG   TAC   TTC   AGG   AGA   ATC   CGT   CTG   TAC   CTG   ACA   GAG   AAG   AAA 140                         145                         150
Tyr   Ser   Asp   Cys   Ala   Trp   Glu   Ile   Val   Arg   Val   Asp   Ile   Met   Arg
TAC   AGT   GAC   TGT   GCC   TGG   GAG   ATT   GTC   AGA   GTG   GAC   ATC   ATG   AGA 155                         160                         165
Ser   Phe   Ser   Ser   Ser   Ala   Asn   Leu   Gln   Gly   Arg   Leu   Gly   Met   Arg
TCC   TTC   TCT   TCA   TCA   GCA   AAC   CTG   CAA   GGA   AGG   TTA   GGA   ATG   AAG
```

-continued
Formula IV

```
                        170                  175              180
Asp  Gly  Asp  Leu  Gly  Ser  Pro  +
GAT  GGA  GAC  CTG  GGG  TCA  CCT  TGA
```

Formula V and dog interferon and the sequence of the following formula coding for it:

```
1                       5                              10                              15
Cys  His  Leu  Pro  Asp  Thr  His  Gly  Leu  Arg  Asn  Trp  Arg  Val  Leu
TGC  CAC  CTG  CCC  GAC  ACC  CAC  GGC  CTG  CGC  AAC  TGG  AGG  GTC  CTG 20                             25                              30
Thr  Leu  Leu  Gly  Gln  Met  Arg  Arg  Leu  Ser  Ala  Gly  Ser  Cys  Asp
ACG  CTC  CTG  GGA  CAG  ATG  AGG  AGA  CTC  TCC  GCC  GGC  TCT  TGT  GAC 35                             40                              45
His  Tyr  Thr  Asn  Asp  Phe  Ala  Phe  Pro  Lys  Glu  Leu  Phe  Asp  Gly
CAC  TAC  ACC  AAT  GAC  TTT  GCC  TTC  CCC  AAG  GAG  CTG  TTT  GAT  GGC 50                             55                              60
Gln  Arg  Leu  Gln  Glu  Ala  Gln  Ala  Leu  Ser  Val  Val  His  Val  Met
CAG  CGG  CTC  CAG  GAG  GCG  CAG  GCC  CTC  TCT  GTG  GTC  CAC  GTG  ATG 65                             70                              75
Thr  Gln  Lys  Val  Phe  His  Leu  Phe  Cys  Pro  Asp  Thr  Ser  Ser  Ala
ACC  CAG  AAG  GTC  TTC  CAC  CTC  TTC  TGC  CCG  GAC  ACG  TCC  TCT  GCT 80                             85                              90
Pro  Trp  Asn  Met  Thr  Leu  Leu  Glu  Glu  Leu  Cys  Ser  Gly  Leu  Ser
CCT  TGG  AAC  ATG  ACT  CTC  CTG  GAG  GAA  CTG  TGC  TCG  GGG  CTC  TCT 95                             100                             105
Glu  Gln  Leu  Asp  Asp  Leu  Glu  Ala  Cys  Pro  Leu  Gln  Glu  Ala  Gly
GAG  CAG  CTG  GAT  GAC  CTG  GAG  GCC  TGT  CCC  CTG  CAG  GAG  GCG  GGG 110                            115                             120
Leu  Ala  Glu  Thr  Pro  Leu  Met  His  Glu  Asp  Ser  Thr  Leu  Arg  Thr
CTG  GCC  GAG  ACC  CCC  CTC  ATG  CAT  GAG  GAC  TCC  ACC  CTG  AGG  ACC 125                            130                             135
Tyr  Phe  Gln  Arg  Ile  Ser  Leu  Tyr  Leu  Gln  Asp  Arg  Asn  His  Ser
TAC  TTC  CAA  AGG  ATC  TCC  CTC  TAC  CTG  CAA  GAC  AGG  AAC  CAC  AGC 140                            145                             150
Pro  Cys  Ala  Trp  Glu  Met  Val  Arg  Ala  Glu  Ile  Gly  Arg  Ser  Phe
CCG  TGT  GCC  TGG  GAG  ATG  GTC  CGA  GCA  GAA  ATC  GGG  AGA  TCC  TTC 155                            160                             165
Phe  Ser  Ser  Thr  Ile  Leu  Gln  Glu  Arg  Ile  Arg  Arg  Arg  Lys  +
TTC  TCC  TCG  ACA  ATC  TTG  CAA  GAA  AGA  ATC  AGG  AGG  AGG  AAA  TGA
```

BRIEF DESCRIPTION OF THE DRAWINGS

FIGS. 2A and 2B are restriction maps of clone λEqα1 and of the resulting plasmid pAH50.

FIGS. 3A and 3B are restriction maps of clone λEq-β6 and of the resulting plasmid pAH60.

FIGS. 4A, 4B, and 4C show the nucleotide and putative amino acid sequences of EqIFN-α1 (pAH50 HindIII fragment).

FIG. 5 is a comparison of Eq-α1 interferon with alpha interferon from horse (Eq), cattle (Bo), mouse (Mu), rat (Ra) and man (Hu), showing the degree of homology among the mature proteins. The references Eq, Bo, Mu, Ra, Hu and also canine (Ca) are used consistently in the remaining figures.

FIG. 6 is a comparison of beta interferon is a variety of species, and shows the similarities and differences among the species.

FIGS. 7A and 7B are a comparison of EqIFN-α1 with alpha interferons in other species, showing the amino acid differences among the species tested.

FIGS. 8A, 8B and 8C show the nucleotide and putative amino acid sequences of EqIFN-β (pAH60 HindIII fragment).

FIGS. 10A and 10B show the nucleotide and putative amino acid sequence of EqIFN-α2 (pRH63).

FIGS. 11A, 11B, 11C and 11D show a side-by-side comparison of the genes encoding EqIFN-α1 (pAH50) and EqIFN-α2 (pRH63) as well as the putative amino acid sequences.

FIGS. 12A, 12B and 12C show the nucleotide and putative amino acid sequences of EqIFN-omega (pRH61 EcoR1 fragment).

FIG. 17 shows a hybridization blot comparing the protein expression products of pER103, pER21/1, pAH52, pAH53, pAH53/2, pAH62 and pAH62ΔG1.

FIGS. 19A, 19B and 19C show a comparison between Eq-alpha interferon and the alpha and beta interferons of various other species.

FIGS. 20A and 20B are charts showing the percentage of homology between the proteins encoded by the comparative samples used in FIGS. 19A–19C.

FIG. 23 is a restriction map of clone Ca-α2 (pAH4, p AH2).

FIGS. 24A, 24B and 24C show nucleotide and putative amino acid sequences of CaIFN-α2 (pAH2 HindIII fragment).

FIGS. 25A, 25B and 25C show the nucleotide and putative amino acid sequences of CaIFN-α1 (pAH4 HindIII fragment).

FIGS. 26A and 26B show a comparison of Ca-α1 interferon with alpha interferons in other species, showing the amino acid differences among the species tested.

FIG. 27 is a comparison of Ca-α1 interferon with alpha interferons in other species, showing the degree of homology with the mature protein.

FIGS. 31A and 31B show the nucleotide and putative amino acid sequences of EqIFN-ω2 (pRH62).

FIGS. 32A, 32B, 32C and 32D show a side-by-side comparison of the genes encoding EqIFN-ω1 and EqIFN-ω2, along with the putative amino acid sequence.

FIGS. 33A and 33B show a chart showing the percentage of homology between interferons from various species.

FIGS. 34A and 34B show the nucleotide and putative amino acid sequences of EqIFN-α3 (pRH83).

FIGS. 35A and 35B show the nucleotide and putative amino acid sequences of EqIFN-α4 (pRH82).

FIGS. 36A, 36B and 36C show a comparison between Eq-alpha interferon and the alpha, beta and omega interferons of various other species.

FIG. 37 shows the nucleotide and putative amino acid sequences of the mature form of EqIFN-ω2.

FIG. 38 shows the nucleotide and putative amino acid sequences of the mature form of EqIFN-α3.

FIG. 39 shows the nucleotide and putative amino acid sequences of the mature form of EqIFN-α4.

The aim of the invention was achieved by isolating high-molecular DNA from the tissues of the animals mentioned, preferably from the liver, by a modified process described by Blin and Stafford (18) and statistically fragmenting it with the aid of special endonucleases. The resulting fragments of different sizes were fractionated according to their size, preferably to form 10–23 kb fragments, in order to be cloned in a vector, for example, a lambda-vector. These vectors were then replicated in a bacterium, preferably E. coli.

The horse DNA was screened with the aid of the DNA coding for mature human interferon-alpha2ARG and the cDNA coding for human β-interferon under non-stringent conditions.

The dog DNA was screened using the DNA coding for mature human interferon-alpha2ARG under non-stringent conditions.

Because of the lack of stringency, clones were also obtained which differ substantially in their sequences from the HuIFN-alpha-2Arg and HuIFN-β.

When the horse DNA was probed with the human alpha gene, several bands were found, as in the case of cattle, pigs and humans, by Southern analysis, so that one can assume that there must also be a class of alpha-interferon genes in horses.

Phage DNA was prepared from the hybridizing recombinants and restriction maps (FIGS. 2A–2B and 3A–3B) were drawn up from the resulting clones Eq-alpha1, Eq-beta6. Furthermore, two lambda clones, Eq-alpha16 and Eq-alpha20 hybridizing with the human IFN probe were obtained. A 3.2 kb Hind III fragment from the clone Eq-alpha1, a 4.5 kb PvuII fragment of the clone Eq-beta6, a 3.3 kb EcORI fragment of the clone Eq-alpha16 or a 2.2 kb EcoRI fragment of the clone Eq-alpha20 was sub-cloned in a vector, for example pUC9, and then transformed into a host organism, for example E. coli JM101. Isolation of the correct phenotypes yielded the plasmids pAH50, pAH60, pRH63 and pRH61 which contain as inserts the sequences coding for the horse interferons.

Figure 9:
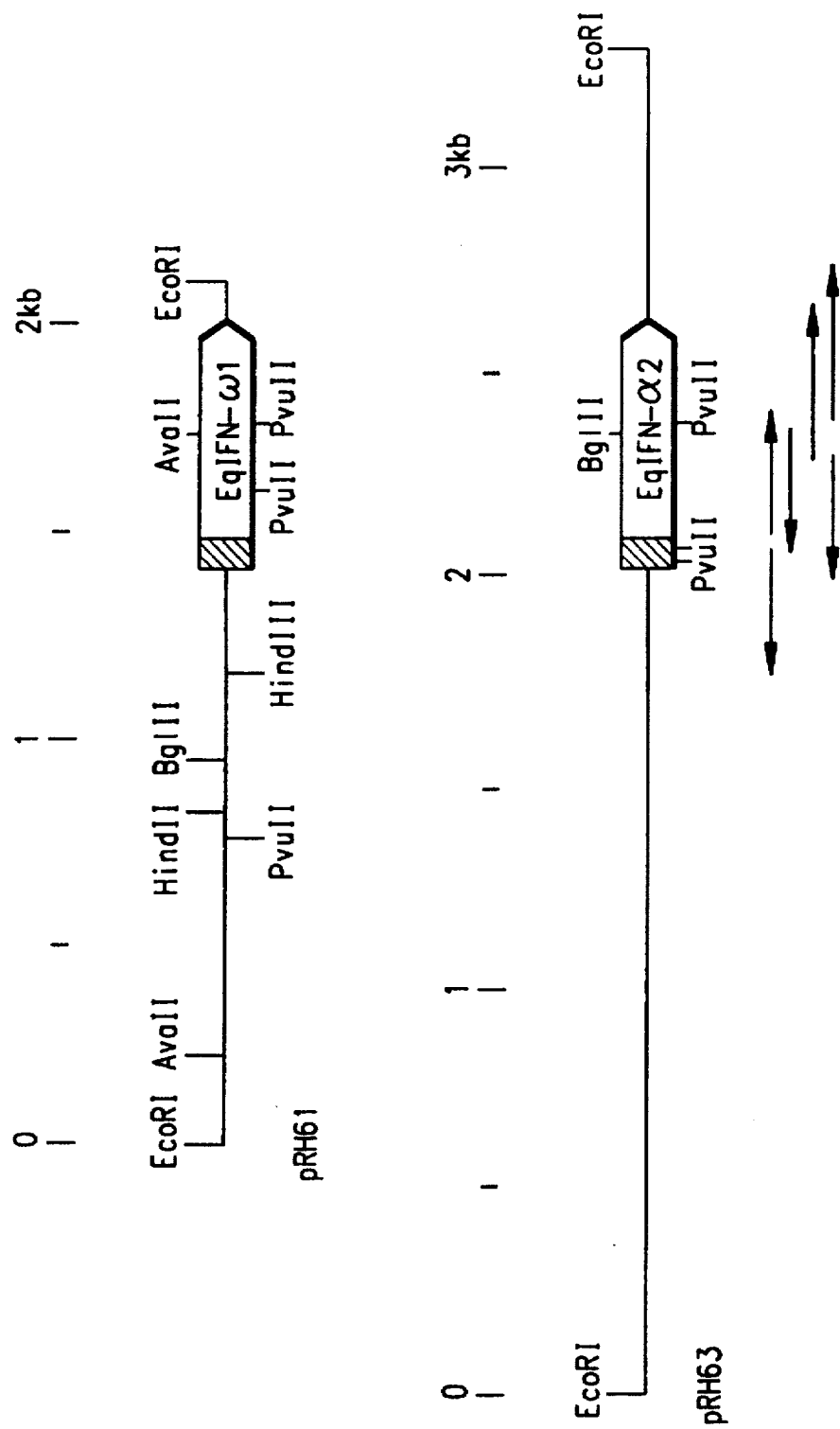
FIG. 9 is a restriction map of expression plasmids pRH61 and pRH63.

The restriction maps for pRH61 and pRH63 are shown in FIG. 9.

The inserts of the plasmids were sequenced by the dideoxy method described by Sanger (23) usine the "shotgun method". The partial sequences of these inserts were combined, using a modified computer program, to form a total sequence (FIGS. 4A–4C, 8A–8C, 10A–10B and 12A–12C).

The longest open reading fame for the Eq-IFN-alpha gene from the clone Eq-alpha1 encodes a polypeptide with 184 amino acids. It is worth noting the significant homology with known alpha-interferons of other species. As in the case of human, bovine and murine alpha-interferons, this horse alpha-interferon consists of a hydrophobic signal peptide with 23 amino acids which preceeds a mature protein with, surprisingly, only 161 amino acids (Eq-IFN-alpha1). Four cysteine groups at positions 1, 29, 99 and 139 are preserved exactly among the species horse, cattle, mouse, rat and man (FIG. 7A–7B). The shortening of this horse alpha-interferon to 161 amino acids must have been brought about by the deletion of a base after the 159 amino acid without which the transcription would have continued up to the 166th amino acid, up to the stop codon TGA.

This finding indicates that the polypeptide chain for mature horse interferom alpha1 may have a length of 161 amino acids but that other forms with up to 166 amino acids may exist. These peptides are, of course, further objects of the present invention.

Surprisingly, a pair-by-pair comparison of the amino acid sequences showed that the horse interferon alpha1 shows greater homology to human alpha interferons (71–77%) than to cattle (57–67%), rat (61%) or mouse alpha-interferons (54–59%) (FIG. 5). The homology between the different alpha-interferons of a genus is significantly greater than between different species (e.g. man 77–100%, cattle 91–99%).

The longest open reading frame for the Eq-IFN-alpha gene from the clone Eq-alpha16 also codes a polypeptide with 184 amino acids (signal peptide 23 amino acids, mature protein 161 amino acids).

The DNA sequence of the clone pRH63 is very similar to that of the clone pAH50 in the protein-coding region, a fact which can be exploited for the expression of the gene (see Example M; FIGS. 11A–11D and 15). The interferon from clone pRH63 was entitled Eq-IFN-alpha2, owing to its great homology with Eq-IFN-alpha1 (from clone pAH50). Mature Eq-IFN-alpha2, compared with Eq-IFN-alpha1, has only two different amino acid groups at the C-terminal end, whilst as a result of the interchange at position 151 Ser-Cys, in Eq-IFN-alpha2 there is a fifth cysteine group at a position which has not hitherto been observed in any other interferon (see FIGS. 19A–19C).

Otherwise, what was said regarding Eq-IFN-alpha1 also applies to Eq-IFN-alpha2!

The DNA fragment of Eq-alpha20 contains the coding sequence for a protein with 172 amino acids and a hydrophobic signal peptide with 23 amino acids. At position 78–80 of the mature protein there is a potential N-glycosylation site Asn-Thr-Thr, which corresponds exactly to that of Eq-IFN-β, Hu-IFN-β, Mu-IFN-β, Mu-IFN-alpha1,2,4,5,6 (FIGS. 19A–19C).

The protein sequences in this Figure were arranged so as to achieve maximum homology between the individual interferons. In order to compare IFN-alpha and IFN-β sequences, the latter were displaced by three amino acids and a gap was introduced. The pair-by-pair comparison of the amino acid sequences in FIGS. 20A–20B was effected starting from this arrangement over the longest common length of the proteins.

FIGS. 19 and 20A–20B show that the protein coded by the DNA sequence of the clone pRH63 is related to the type I interferons (α- and β-IFN). The characteristics of 172 amino acids, glycosylation site at position 78 and the approximately equal homology of the interferons of this class between different species (man, cattle, horses) and between these longer interferons and the α-interferons within a genus, and the different sets of DNA fragments hybridizing with α-interferon and probes from the clone pRH63 (FIG. 18) lead one to assume that the insert of clone pRH63 belongs to a new class of type I interferons which is designated omega-interferon (33). This name is less confusing than the one used by Capon et al. (34): type I, class II interferon, which might lead to confusion with type II interferon (IFN-gamma).

The sequence of horse-beta-interferon was determined analogously to that of the alpha-interferon. The longest open reading frame for the beta-IFN gene codes for a polypeptide with 186 amino acids, whilst once again the homology with known beta-interferons of other species is noticable. As in the case of human beta-interferon, the 3 bovine beta-interferons and the murine-beta-interferons, horse beta-interferon has a hydrophobic signal peptide with 21 amino acids.

Surprisingly, in beta-interferon, too, a pair-by-pair comparison of the amino acid sequences showed that horse beta-interferon has a greater homology to human beta-interferon (59%) than to cattle (50–55%) or mouse beta-interferons (44%) (FIG. 6).

On the other hand, in spite of the surprisingly high homology between horse and human beta-interferon, as with the three bovine beta-interferons the amino acid located at position 119 in human beta-interferon is absent from horse beta-interferon!

Horse beta-interferon carries two potential N-glycosylation sites: at position 80 of the mature protein (Asn-Glu-Thr, as in human and mouse beta-interferon) and at position 115 (Asn-Thr-Thr). In the bovine beta-interferons two possible N-glycosylation sites are located at posit ion 110 (Asn-Phe-Thr or Asn-Ser-Phe) and 152 (Asn-Val-Ser or Asn-Phe-Ser).

As in cattle and humans the three cysteine groups are kept exactly the same (positions 17, 31 and 140 or 141 in the case of humans).

When investigating dog DNA with the human alpha gene, several bands were found just as in cattle, pigs and humans which means that we can presume that there must be a class of alpha-interferon genes in dogs.

Figure 22:
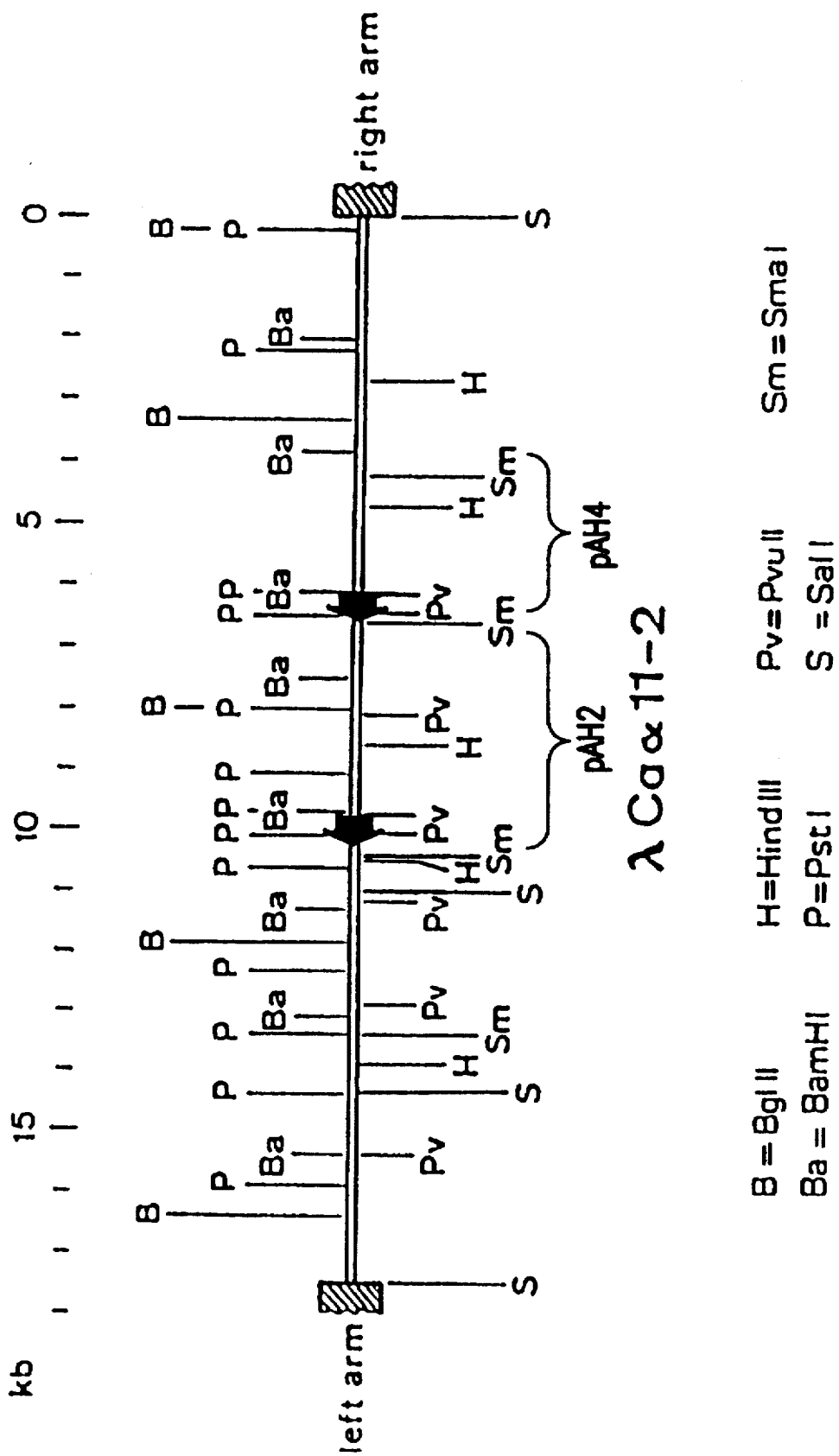
FIG. 22 is a restriction map of clone λCaα-11-2.

Phage DNA was prepared from the hybridizing recombinants and a restriction map was drawn up from the resulting clone Ca alpha11-2 (FIG. 22). A 3,7 kb SmaI fragment and a 2,4 kg SmaI fragment of this clone were subcloned in a vector, for example, pUC9, and then transformed into a microorganism, for example E. coli JM101. Isolation of the correct phenotypes yielded two plasmids pAH2 and pAH4 which contain as insertions the sequences coding for the dog interferons.

The insertions in these plasmids were sequenced by the dideoxy method described by Sanger (23) using the "Shotgun method". The partial sequences of these insertions were combined using a modified commuter program to form a total sequence (FIGS. 24A–24C and 25A–25C).

Surprisingly, the longest open reading frame of both plasmid sequences codes for totally identical polypeptides with 187 amino acids. The significant homology with known alpha-interferons of other species is noticable. The protein-coding sequences are exactly the same; 170 bases of the 5'-non-translated region differ by only 3 nucleotides (1.8%) (cf. 28). As in human, bovine and murine alpha-interferons, dog-alpha-interferon consists of a hydrophobic signal peptide with 23 amino acids which preceeds a mature protein with surprisingly only 161 amino acids. Compared with the protein sequences of other alpha-interferon genes described, dog alpha-interferon lacks two amino acids at positions 119 and 120 of the mature protein (FIGS. 26A–26B).

Surprisingly, mature dog alpha-interferon is the only alpha-interferon as yet known which has six cysteine groups; thus, three intramolecular disulfide bridges are possible!

Four of these cysteine groups at positions 1, 29, 99 and 139 are exactly the same between the species dog, cattle, mouse, rat and man. The cysteine at position 86 is preserved between CAIFN-alpha1, CaIFN-alpha2, MuIFN-alpha1, MuIFN-alpha2, RaIFN-alpha and HuIFN-alphaD.

Surprisingly, dog alpha-interferon has two potential N-glycosylation sites namely at positions 78 (Asn-Met-Thr) and 133 (Asn-His-Ser). The glycosylation site at position 78 corresponds to that in MuIFN-alpha1 and 2 (Asn-Ala-Thr); it also corresponds to the glycosylation site of the beta-interferons from man and mouse at position 80 (Asn-Glu-Thr)!

Pair-by-pair comparison of the amino acid sequences showed that dog alpha-interferon has a homology of 52–57% with human alpha-interferon, 54–55% with cattle alpha-interferons, 50% with rat alpha-interferons and 48–51% with mouse alpha-interferons (FIG. 27).

It should be mentioned at this point that the interferons according to the invention are not only the mature interferons which are described in detail but also any modification of these polypeptides which do not essentially alter the horse/dog-IFN activity. These modifications, include, for example, shortening of the molecule e.g. at the N- or C-terminal end, replacement of amino acids by other groups, chemical or biochemical bonding of the molecule to other molecules which are inert or active. These latter modifications may concern, for example, hybrid molecules from one or more interferons according to the invention and/or known alpha- or beta-interferons.

The invention therefore relates not only to gene sequences which code specifically for the interferons according to the invention but also to modifications which may easily and routinely be obtained by mutation, degradation, transposition or addition. All sequences which code for the interferons according to the invention (i.e. which have the biological activity spectrum described herein) and which are degenerate compared with those shown are also included; experts in this field are capable of degenerating DNA sequences of the coding regions. Similarly all sequences which code for a polypeptide with the activity spectrum of the interferons according to the invention and which hybridize with the sequences shown (or parts thereof) under stringent conditions (for example conditions which select for more than 85%, preferably more than 90% homology) are also included.

The hybridizations are carried out in 6×SSC/5× Denhardt's solution/0.1% SDS at 65° C. The degree of stringency is determined in the washing step. Thus, for selection of DNA sequences with approximately 85% or more homology, suitable conditions are 0.2×SSC/0.01%, SDS/65° C. and for selection of DNA sequences with approximately 90% homology or more, the suitable conditions are 0.1×SSC/0.01% SDS/65° C.

Interferon genes according to the invention may be introduced into any organism under conditions which result in high yields. Suitable hosts and vectors are well known to those skilled in the art; your attention is drawn, for example, to European Patent Application 0,093,619.

Prokaryotes are particularly preferred for expression, for example *E. coli* K 12, strain 294 (ATCC No. 31 446) or *E. coli* X1776 (ATCC No. 31,537). Apart from the above mentioned strains it is also possible to use *E. coli* w 3110 (F⁻, Lambda⁻, prototroph, ATCC No. 27325), bacilli such as *Bacillus subtilis* and other enterobacteriaceae, such as *Salmonella typhimurium* or *Serratia marcescens* and various Pseudomonads.

In general, plasmid vectors which contain replicon and control sequences originating from species which are compatable with the host cells may be used in conjunction with these hosts. The vector usually carries, beside a replication site, recognition sequences which make it possible to select the transformed cells phenotypically. For example, *E. coli* is usually transformed with pBR322, a plasmid which originates from the species *E. coli* (Bolivar, et al., Gene 2, 95 (1977). pBR322 contains genes for ampicillin and tetracyclin resistance and thus affords simple means of identifying transformed cells. The pBR322 plasmid or other plasmid must, in addition, contain promoters themselves or must be modified so that they contain promoters which can be used by the microbial organism for the expression of its own proteins. The promoters most frequently used in the preparation of recombinant DNA include beta-lactamase (penicillinase) and lactose promoter systems (Chang et al., Nature 275, 615 (1978); Itakura et al., Science 198, 1056 (1977); Goeddel et al., Nature 281, 544 (1979)) and Tryptophan(trp) Promoter Systems (Goeddel et al., Nucleic Acids Res. 8, 4057 (1980); EP-A-0,036,776). Whereas these are the most common promoters, other microbial promoters have also been developed and used. The genetic sequence for the interferons according to the invention may be used, for example, under the control of the leftward promoter of the bacteriophage lambda ($P_L$). This promoter is one of the promoters known to be particularly powerful and is also controllable. Control is made possible by the lambda repressor of which adjacent restriction cutting sites are known.

A temperature-sensitive allele of this repressor gene may be inserted in a vector which contains a complete IFN-omega sequence. If the temperature is increased to 42° C., the repressor is deactivated and the promoter is expressed up to its maximum concentration. The total of the mRNA produced under these conditions should be sufficient to obtain a cell which contains, among its new synthetic ribonucleic acids, approximately 10% originating from the $P_L$ promotor. In this way it is possible to establish a clone bank in which a functional IFN sequence is placed in the neighbourhood of a ribosome bonding site at varying distances from the lambda $P_L$ promotor. These clones can then be checked and those with the highest yield selected.

The expression and translation of a sequence coding for the proteins according to the invention may also be effected under the control of other regulating systems which may be regarded as "homologous" to the organism in its untransformed form. Thus, for example, chromosomal DNA from a lactose-dependant *E. coli* contains a lactose or lac-operon which enables lactose degradation by secreting the enzyme beta-galactosidase.

The lac-control elements may be obtained from the bacteriophage lambda-plac5, which is infectious for E. coli. The Lac-operon of the phage may be obtained from the same bacterial species by transduction. Regulating systems which may be used in the process according to the invention may originate from plasmidic DNA which is native to the organism. The lac-promoter-operator system may be induced by IPTG.

Other promoter-operator systems or parts thereof may be used with equally good effect: for example arabinose operator, colicine $E_1$-operator, galactose operator, alkaline phosphatase operator, trp operator, xylose-A-operator, tac-promotor, etc.

In addition to prokaryotes, eukaryotic microorganisms such as yeast cultures may also be used. *Saccharomyces cerevisiae* is the most commonly used of the eukaryotic microorganisms, although a number of other species are generally obtainable. For expression in *Saccharomyces*, the plasmid YTp7 is normally used, for example (Stinchcomb et al., Nature 282, 39 (1979); Kingsman et al., Gene 7, 141 (1979); Tschumper et al., Gene 10, 157 (1980)) and the plasmid YEp 13 (Bwach et al., Gene 8, 121–133 (1979)) is also conventionally used. The plasmid YRp7 contains the TRP1 gene which presents a selectable marker for a yeast mutant which is incapable of growing in tryptophan-free medium; for example ATCC No. 44076.

The presence of the TRP1 defect as a characteristic of the yeast host genome then constitutes an effective aid to detecting transformation, in which cultivation is carried out without tryptophan. The situation is very similar with the plasmid YEp13, which contains the yeast gene LEU 2, which can be used to complement a LEU-2-minus mutant. Suitable promoter sequences for yeast vectors contain the 5'-flanking region of the genes of ADH I (Ammerer G., Methods of Enzymology 101, 192–201 (1983)), 3-phosphoglycerate-kinase (Hitzeman et al., J. Biol. Chem. 255 2073 (1980), or other glycolytic enzymes (Kawaski and Fraenkel, BBRC 108, 1107–1112 (1982)) such as enolase, glycer-aldehyde-3-phosphate-dehydrogenase, hexokinase, pyruvate decarboxylase, phosphofructokinase, glucose-6-phosphate-isomerase, phosphoglucose-isomerase and -glucokinase. By constructing suitable expression plasmids, the termination sequences associated with these genes may also be inserted in the expression vector at the 3'-end of the sequence which is to be expressed, in order to predict poly-adenylation and termination of the MRNA.

Other promoters which also have the advantage of transcription controlled by growth conditions are the promoter regions of the genes for alcohol dehydro-genase-2, isocytochrome C, acid phosphatase degrading enzymes which are coupled to the nitrogen metabolism, the above mentioned glyceraldehyde-3-phosphate-dehydrogenase and enzymes which are responsible for the processing of maltose and galactose. Promoters which are regulated by the yeast Mating Type Locus, for example promoters of the genes BAR1, MFα1, STE2, STE3 and STE5, may be used in temperature-regulated systems by the use of temperature dependent sir mutations. (Rhine Ph.D. in Thesis, University of Oregon, Eugene, Oreg. (1979), Herskowitz and Oshima, the Molecular Biology of the Yeast *Saccharomyces*, part I, 181–209 (1981), Cold Spring Harbour Laboratory). These mutations affect the expression of the resting Mating Type cassettes of yeasts and thus indirectly the Mating Type dependant promoters. Generally, however, any plasmid vector which contains a yeast-compatible promoter, original replication and termination sequences, is suitable.

In addition to microorganisms, cultures of multicellular organisms are als o suitable host organisms. In theory, any of these cultures may be used, whether obtained from vertebrate or invertebrate animal cultures. However, the greatest interest has been in vertebrate cells, with the result that the multiplication of vertebrate cells in culture (tissue culture) has become a routine method in recent years (Tissue Culture, Academic Press, Editors Kruse and Patterson, (1973)). Examples of useful host cell lines of this kind include VERO and HeLa cell, chinese hamster ovary (CHO) cells and W138, BHK, COS-7 and MDCK cell lines. Expression vectors for these cells generally contain (when necessary) a replication site, a promoter which is located in front of the gene to be expressed, together with any necessary ribosome bonding site, RNA splicing, polyadenylation site and transcriptional termination sequences.

When used in mammalian cells, the control functions in the expression vector are often obtained from viral material. For example, the promoters normally used originate from polyoma adenovirus 2 and particularly frequently from simian virus 40 (SV 40). The early and late promoters of SV 40 are particularly useful since both can easily be obtained from the virus as a fragment with also contains the viral replication site of the SV 40. (Fiers et al., Nature 273, 113 (1978)). It is also possible to use smaller or larger fragments of SV 40, provided that they contain the sequence, approximately 250 bp long, which extends from the HindIII cutting site to the Bgl 1 cutting site in the viral replication site. Furthermore it is also possible and frequently, desirable to use promoter or control sequences which are normally linked to the desired genetic sequences, provided that these control sequences are compatable with the host cell systems.

A replication site may either be provided by corresponding vector construction in order to incorporate an exogenic site, for example from SV 40 or other viral sources (e.g. polyoma, adeno, VSV, PBV, etc.) or it may be provided by the chromosomal replication mechanisms of the host cell. If the vector is integrated in the host cell chromosome, the latter measure is usually sufficient.

However the genes may preferably be expressed in an expression plasmid pER103 (E. Rastl-Dworkin et al., Gene 21, 237–248 (1983) and EP-A-0,115,613 -deposited at the DSM under the number DSM 2773 on 20 Dec., 1983) or in the plasmid parpER33 (EP-A-0,115,613), since these vectors all contain regulating elements which lead to a high expression rate for the cloned genes.

Starting from the expression plasmid parpER33, the "par" sequence responsible for the increased plasmid stability in *E. coli* and the tryptophan promoter-operator sequence together with the artificial ribosomal bonding site was inserted in the plasmid vector pAT153. pAT153 is a shortened derivative of the plasmid pBR322, which lacks a fragment necessary for the mobilisation of DNA (36).

Figure 13:
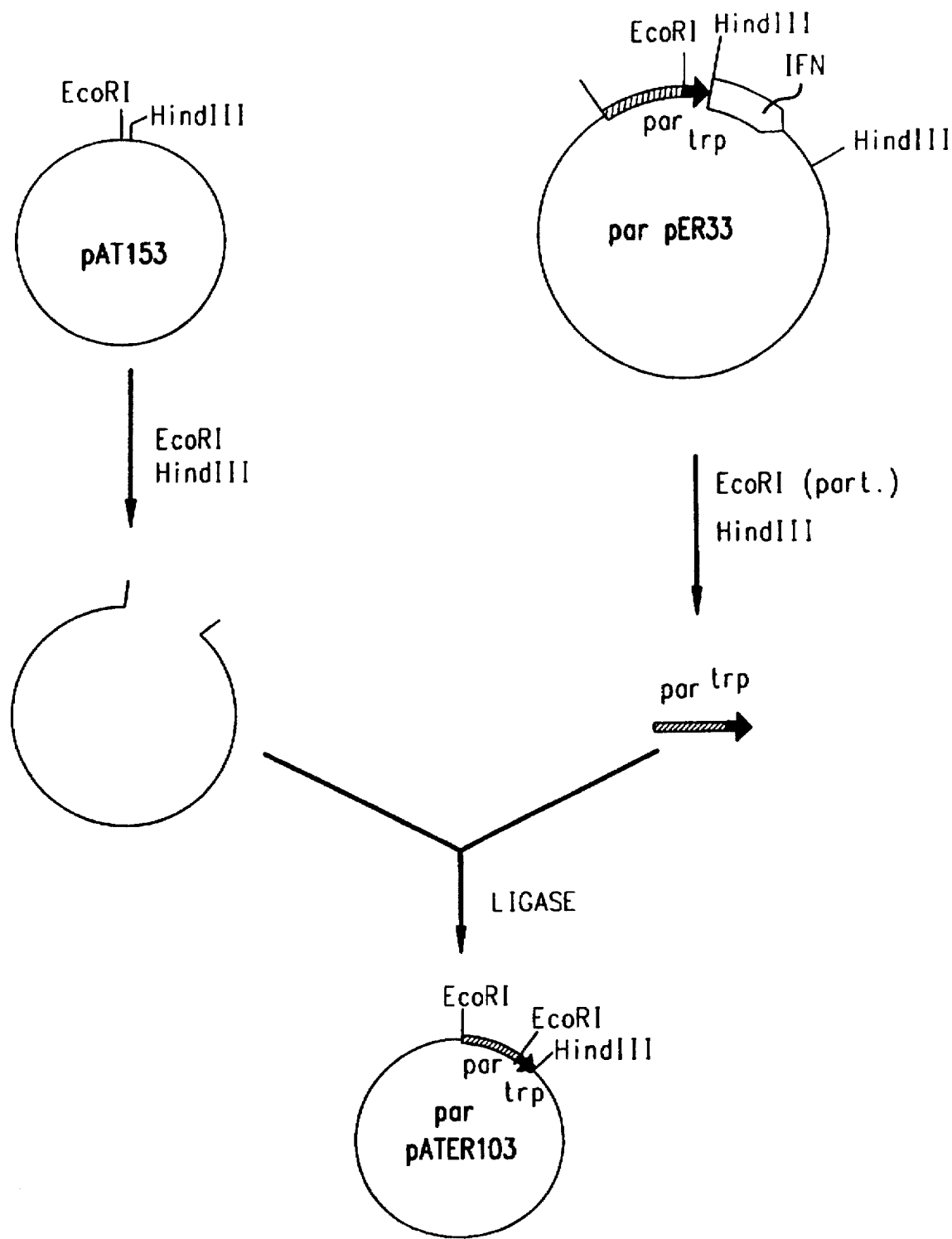
FIG. 13 diagrammatically describes the preparation of plasmid parpATER 103.

The procedure for the preparation of plasmid parpATER103 is shown in FIG. 13. The plasmid parpER33 was fully cut with HindIII and partially cut with EcoRI, the resulting DNA fragment 0.47 kb long was isolated from an agarose gel and purified and ligated with pAT153 which had been cut twice with EcoRI and HindIII. A plasmid of the desired structure obtained after transformation of *E. coli* HB101 and identified by digestion with various restriction enzymes was designated parpATER103. This plasmid contains the replication origin and the ampicillin resistance gene of plasmid pAT153 and the par sequence which is effective for stabilisation in *E. coli* and the trytophan promoter-operator region which may be used for the efficient expression of genes and the ribosomal bonding site.

Figure 14A:
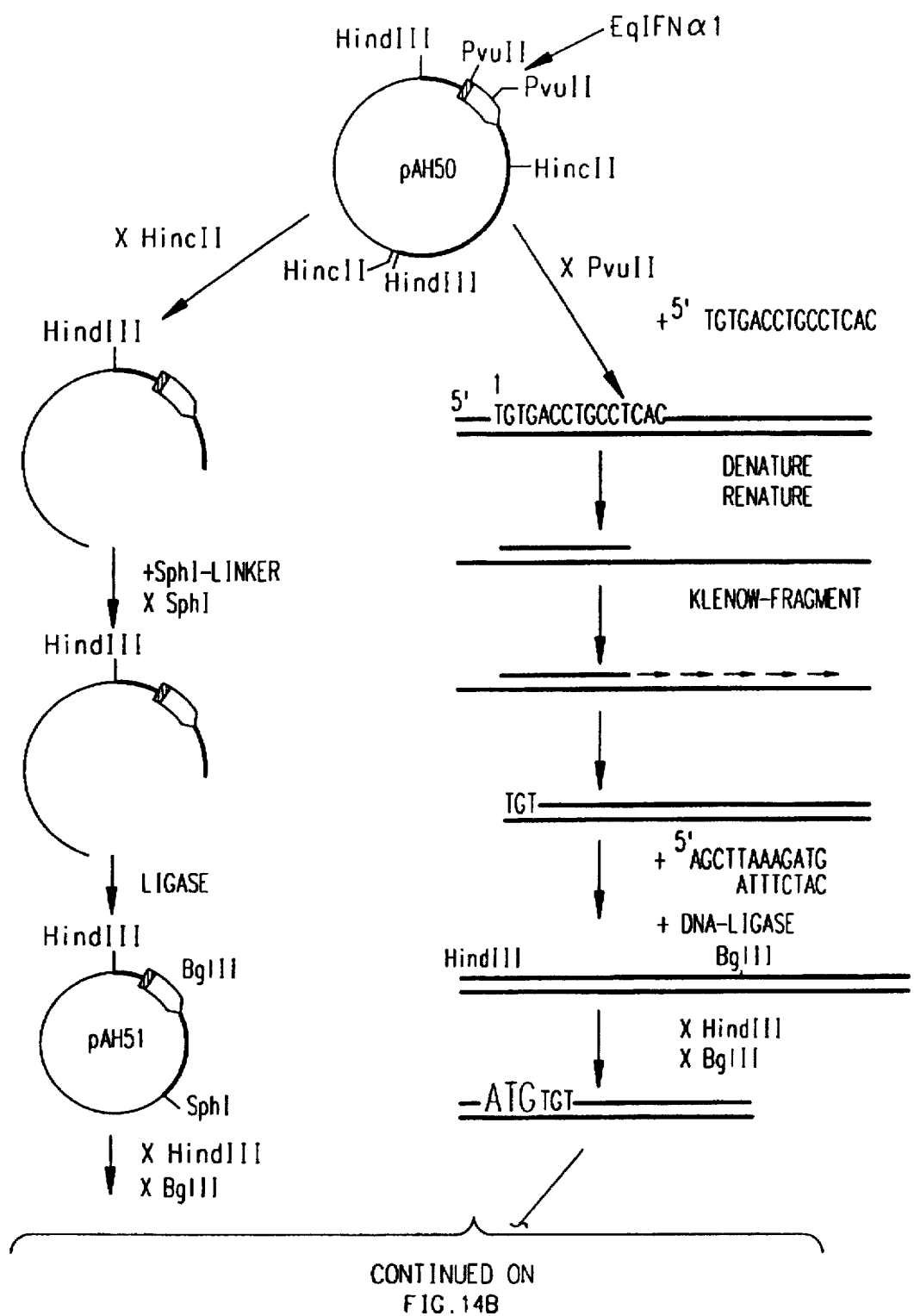
FIGS. 14A, 14B and 14C diagrammatically describe the preparation of expression plasmids pAH52, pAH52/2 and pAH53.
Figure 14B:
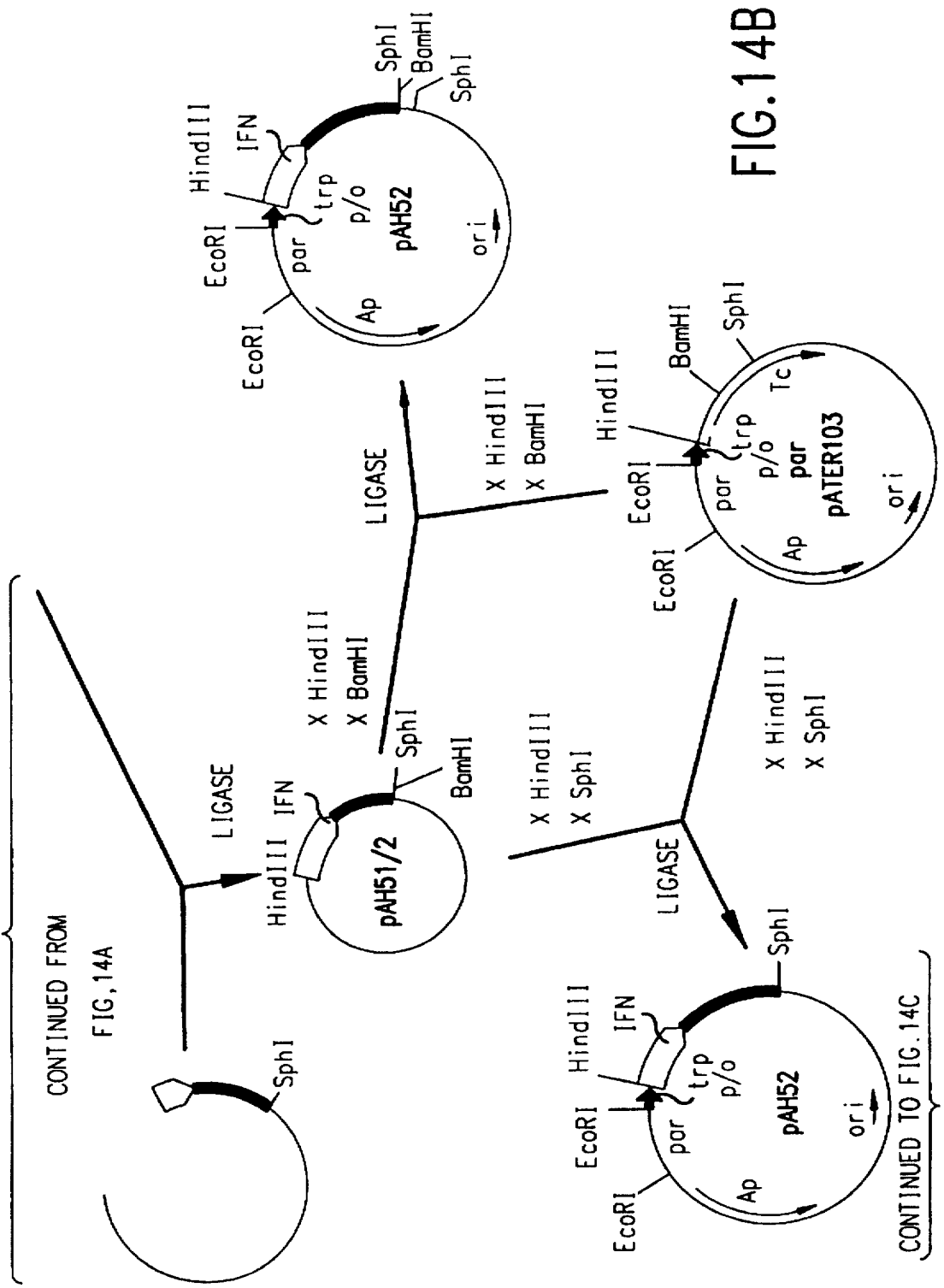
Figure 14C:
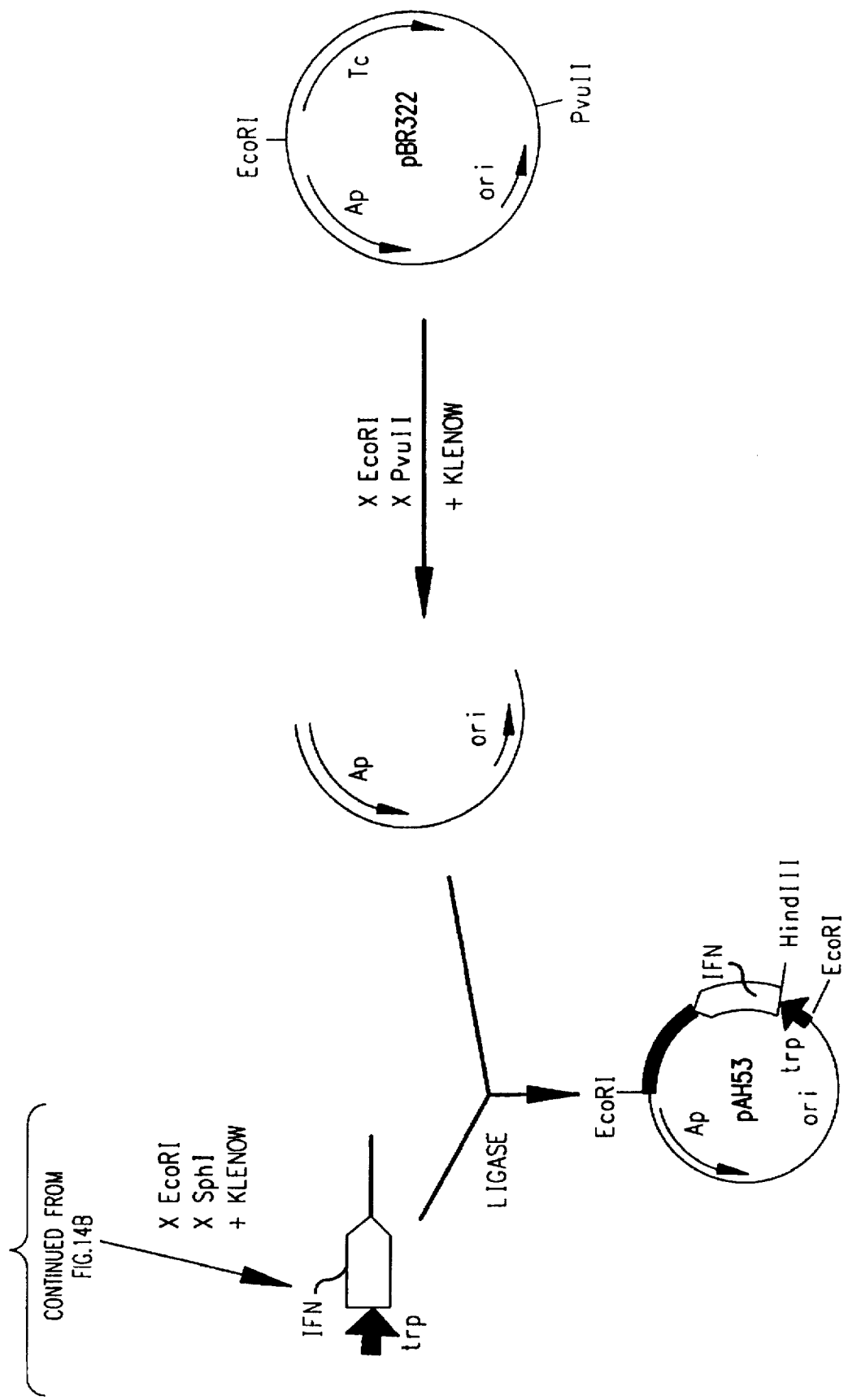

The preparation of the expression plasmids pAH52, pAH52/2 and pAH53 and the preliminary stages thereof is shown in FIGS. 14A–14C. In order to prepare the expression plasmids, the plasmid pAH50 was digested with HindII and the DNA fragment 4.2 kb long containing the entire EqIFN-α1 gene was isolated and purified. The ends of the HindII fragment were provided with SphI linkers. Then the DNA was digested with SphI, extracted with phenol and chloroform and precipitated with ethanol. The DNA was circularised with ligase and transformed with *E. coli* HB101. A plasmid of the desired structure was designed pAH51. It contains the EqIFN-α1 gene with a shortened 3'-non-translated region and an additional SphI cutting site.

In order to bond the DNA sequence for the mature horse α-interferon at the correct distance to the promoter sequence in the final structure, a DNA fragment 0.4 kb long was used which was isolated from plasmid pAH50 cut with PvuII.

Synthetic 15-mer oligonucleotide with the sequence 5'-TGTGACCTGCCTCAC was kinased with polynucleotide kinase. It contains the sequence which codes for the first 5 amino acids of the mature EqIFN-α1 from clone pAH50. The 15-mer was mixed with the 0.5 kb PvuII fragment, the DNA double strand was denatured. The oligonucleotide primer bonded to the single strand was extended with the klenow fragment. In order to ensure that any 3'-overhang left was safely eliminated, the DNA was then incubated with T4 DNA polymerase. The resulting DNA with blunt ends was extracted with phenol and chloroform and precipitated. A mixture of two phosphorylated oligonucleotides complimentary to one another, namely 12 mer 5'-AGCTTAAAGATG, and 8 mer 5'-CATCTTTA (European Patent Application No. 83 112 812.9) was ligated to this DNA fragment, this mixture producing a HindIII cutting site and the translation start codon ATG. Both oligonucleotides were ligated to the DNA fragment with ligase. After deactivation of the enzyme, the DNA obtained was cut with HindIII and BglII and DNA fragments about 190 bp long were isolated and purified. The resulting DNA fragment was ligated with pAH51 vector doubly cut with HindIII and BglII and transformed with *E. coli* HB101. Of the 65 colonies obtained, a HindIII/BamHI DNA fragment was isolated from 4 plasmids having the desired restriction pattern and this DNA fragment was sequenced by the Sanger method, two clones having exactly the required sequence. This plasmid was designated pAH51/2. It contains the sequence for mature EqIFN-α1 with a preceding translation start codon ATG and HindIII cutting site.

In order to prepare the expression plasmids pAH52 and pAH52/2, the plasmid pAH51/2 was cut twice with SphI and HindIII, the resulting DNA fragment 1.0 kb long was isolated from an agarose gel and ligated with plasmid parpATER103 doubly cut with HindIII and SphI. A plasmid of the desired structure obtained after transformation of *E. coli* HB101 was designated pAH52. It contains all the information necessary for inducible expression of mature EqIFN-α1. Analogously, the plasmid pAH52/2 was prepared from pAH51/2 doubly cut with HindIII and BamHI and from parpATER103 cut with HindIII/BamHI. This expression plasmid is about 0.2 kb larger than pAH52 and additionally has a singular BamHI cutting site.

A substantially smaller expression plasmid for producing mature EqIFN-α1 in *E. coli*, in which the tryptophan promoter, the interferon gene, the ampicillin resistance gene and the replication origin are oriented in one direction, was prepared from the plasmids pAH52 and pBR322: namely pAH53. pAH52 was cut with SphI and EcoRI, the enzymes were deactivated at 70° C. and the DNA ends were made blunt after the addition of dATP, dGTP, dCTP and dTTP with klenow fragment. The DNA fragments were fractionated according to size on an agarose gel and a fragment 1.1 kb long containing promoter and interferon gene was isolated. pBR322 was doubly digested with EcoRI and PvuII, the ends were blunted with klenow fragment as described above and then dephosphorylated with calves intestinal phosphatase. A DNA fragment 2.4 kb long was isolated from an agarose gel. The two DNA fragments thus obtained were ligated with T4 DNA ligase and transformed with *E. coli* HB101. The plasmid thus obtained in which two EcoRI recognition sites were created was designated pAH53.

Figure 15:
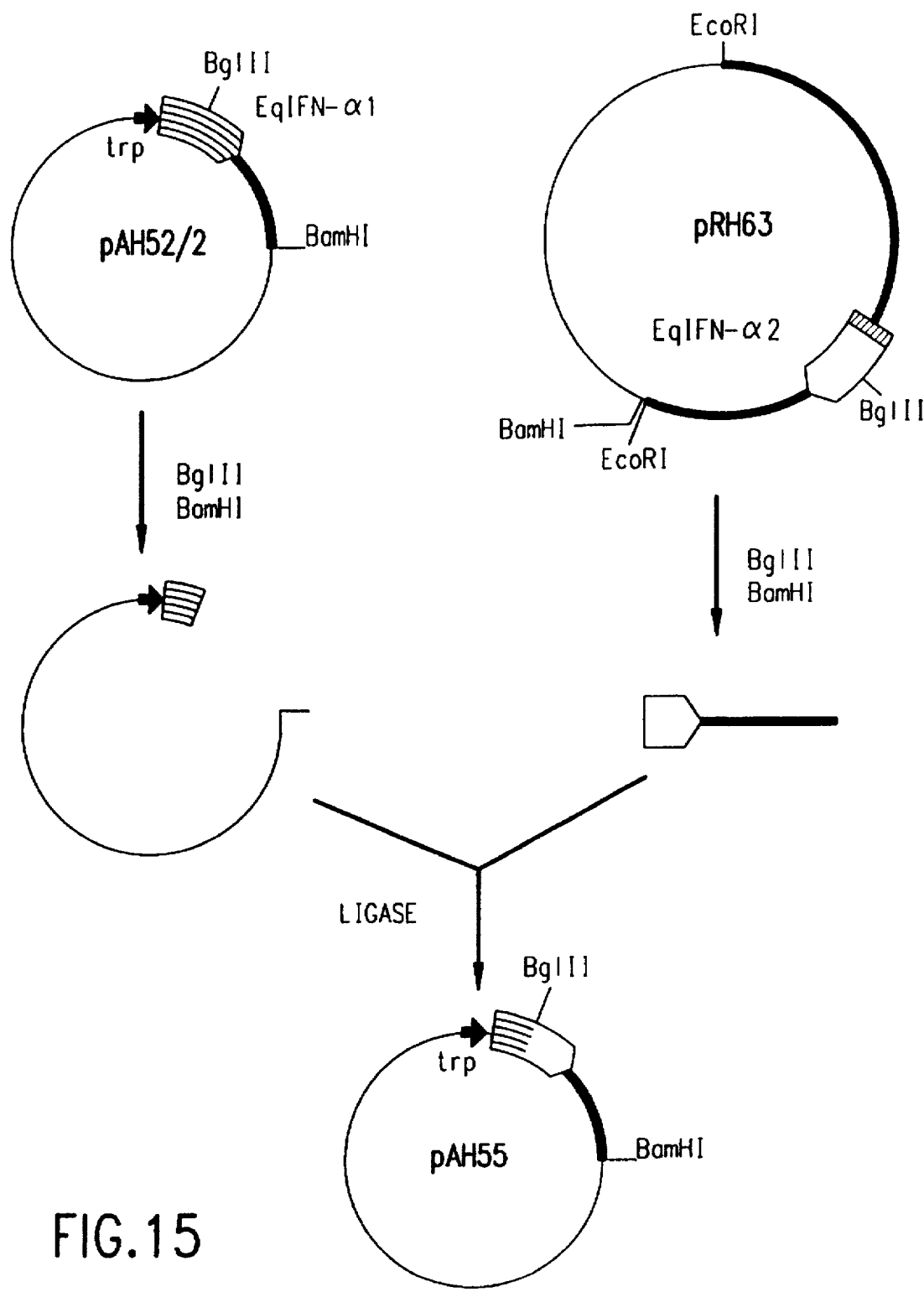
FIG. 15 diagrammatically describes the preparation of expression plasmid pAH55 from expression plasmid pAH52/2 and λ subclone pRH63.

In view of the great homology of the genes for EqIFN-α1 (pAH50) and EqIFN-α2 (pRH63, FIGS. 11A-11D) it is possible to prepare an expression plasmid for EqIFN-α2 from the expression plasmid pAH52/2 and the lambda subclone pRH63 (FIG. 15). Since there are only two base differences up to the common BglII site in the region coding for mature interferon but these differences do not bring about an amino acid difference, owing to the degenerate amino acid code, the first part of the gene for EqIFN-α1 in the expression plasmid pAH52/2 can also be used for the expression of EqIFN-α2. pRH63 was cut twice with BglII and BamHI and the resulting DNA fragment 1.0 kb long which contains the coding sequence for EqIFN-α2 from the 64th amino acid was isolated from an agarose gel. pAH52/2 was also cut with BglII and BamHI, the ends were dephosphorylated with calves intestinal phosphatase and the larger of the two resulting DNA fragments were obtained from an agarose gel. This DNA fragment contains the plasmid vector part, the promoter and the coding sequence for the first 63 amino acids of the mature interferon. The two DNA fragments described were ligated with ligase and transformed with *E. coli* HB101. The plasmid thus obtained which contains the insert in the correct orientation (capable of being cut with BamHI and BglII!) was designated pAH55. This plasmid makes it possible to express mature EqIFN-α2 in *E. coli*.

For preparing an expression plasmid for EqIFN-β, first of all the horse DNA insert from plasmid pAH60 was shortened at the 3' end and this was then manipulated so that a mature EqIFN-β protein is expressed by a bacterial promoter. The procedure is diagrammatically shown in FIGS. 16A–16C. pAH60 was cut with HgiAI. After deactivation of the enzyme, the 3'-overhanging DNA ends were blunted with T4 DNA polymerase (addition of dATP, dGTP, dCTP, dTTP). SphI linkers were ligated to the blunt ends and the resulting DNA was cut with SphI and HindIII. A resulting DNA fragment 1.85 kb long was isolated from an agarose gel and ligated with plasmid parpATER103 doubly cut with HindIII and SphI. A clone with the desired plasmid obtained after transformation of *E. coli* HB101 was designated pAH61. This plasmid constitutes an intermediate stage for further construction of the expression plasmid. pAH61 was cut twice with BamHI and SalI and a resulting DNA fragment 1.3 kb long was isolated from an agarose gel, purified and ligated with M13mp9 phage DNA doubly digested with BamHI/5SalI. After transformation of *E. coli* JM101, single-strand phage DNA could be obtained from a recombinant M13 phage (M13pAH61). This single strand DNA was mixed with the phosphorylated 15mer oligonucleotide 5'-GTGAACTATGACTTG, heated to 95° C. and slowly cooled to ambient temperature. The oligonucleotide binds precisely to the first base of the sequence of the β-interferons. The synthesis of the second strand on the basis of the individual strand starting from the 15mer-primer was carried out after the addition of dATP, dGTP, dCTP, dTTP and klenow fragment. The DNA was extracted and precipitated. Any remaining single-strand DNA portions were digested with S1-nuclease. The mixture of the 12 mer and 8 mer oligonucleotides 5'-AGCTTAAAGATG and 5'-CATCTTTA was ligated onto the DNA which had been made blunt-ended by this treatment and the resulting DNA was cut with HindIII and SphI. A DNA fragment of the desired length of 1.1 kb was isolated from an agarose gel and ligated with plasmid parpATER103 which had been doubly cut with hindIII/SphI. After transformation of *E. coli* HB101, 54 colonies were obtained. From 9 plasmid DNAs isolated therefrom, an EcoRI/SalI fragment 1.3 kb long was isolated and sequenced by the Sanger method. A plasmid obtained therefrom and having the desired sequence was designated pAH62. This plasmid permits efficient expression of mature EqIFN-β protein in *E. coli*. A plasmid which carries a deletion of the first base (G) of the mature β-IFN gene was designated pAH62deltaG1. This plasmid permits expression of a β-IFN shortened at the amino terminus by a translation start at the next ATG (corresponds to amino acid 19 in the mature β-IFN), which surprisingly has antiviral activity, although significantly less than that of the unabbreviated protein.

In order to demonstrate the expression of the interferon activity by *E. coli* HB101 containing the plasmid pAH52, pAH52/2, pAH53, pAH55 or pAH62, the bacteria were lysed after incubation in a suitable culture medium and the supernatant was first filtered sterile and then tested for interferon activity in an assay which measures the cytopathic effect (CPE) of VSV or EMCV. NBL-6 cells (ATCC CCL57, epidermis cells from horses' hide) which had been infected with vesicular stomatitis virus (VSV) and/or A549 (ATCC CCL185, human lung cancer cell line) which had been infected with encephalomyocarditis virus (EMCV) were used for this. The results are listed in Example O.

Detection of the expressed horse interferons was carried out by labelling the proteins in maxicells. Plasmid-coded proteins can be selectively labelled in vivo using the maxicell technique (37). The *E. coli* strain CSR603 (CGSC 5830) (F⁻, thr-1, leuβ6, proA2, phr-1, recA1, argE3, thi-1, uvrA6, ara-14, lacY1, galK2, xyl-5, mtl-1, gyrA98 (nalA98), rpsL31, tsx-33, λ⁻, supE44,) has no mechanisms for repairing damage to DNA caused by UV radiation. Irradiation with a suitable dosage of UV rays destroys the bacterial chromosome, whilst some of the substantially smaller plasmid DNAs which are present in several copies per cell remain functional. After all the undamaged multiplying cells have been killed off by the antibiotic D-cycloserin and the endogenous mRNA has been used up, only genes coded on the plasmid are transcribed and translated in the remaining cells and the proteins formed can be radioactively labelled and detected by the introduction of $^{35}$S-methionine. *E. coli* CSR603 was transformed by conventional methods with the expression plasmids and transformed bacteria selected on ampicillin-containing agar dishes. The preparation of the maxicells and the labelling of the proteins were carried out as described by A. Sancar (37). FIG. 17 shows the autoradiograph of the dried gel. A $^{14}$C-methylated protein mixture (Amersham) was used as a molecular weight standard. The controls used were the plasmid pER103 which contains only the promoter with no interferon gene and the plasmid PER21/1 which contains two copies of the human IFN-2arg gene. The protein bands at about 18 kd are the interferons expressed by the plasmids.

Figure 18:
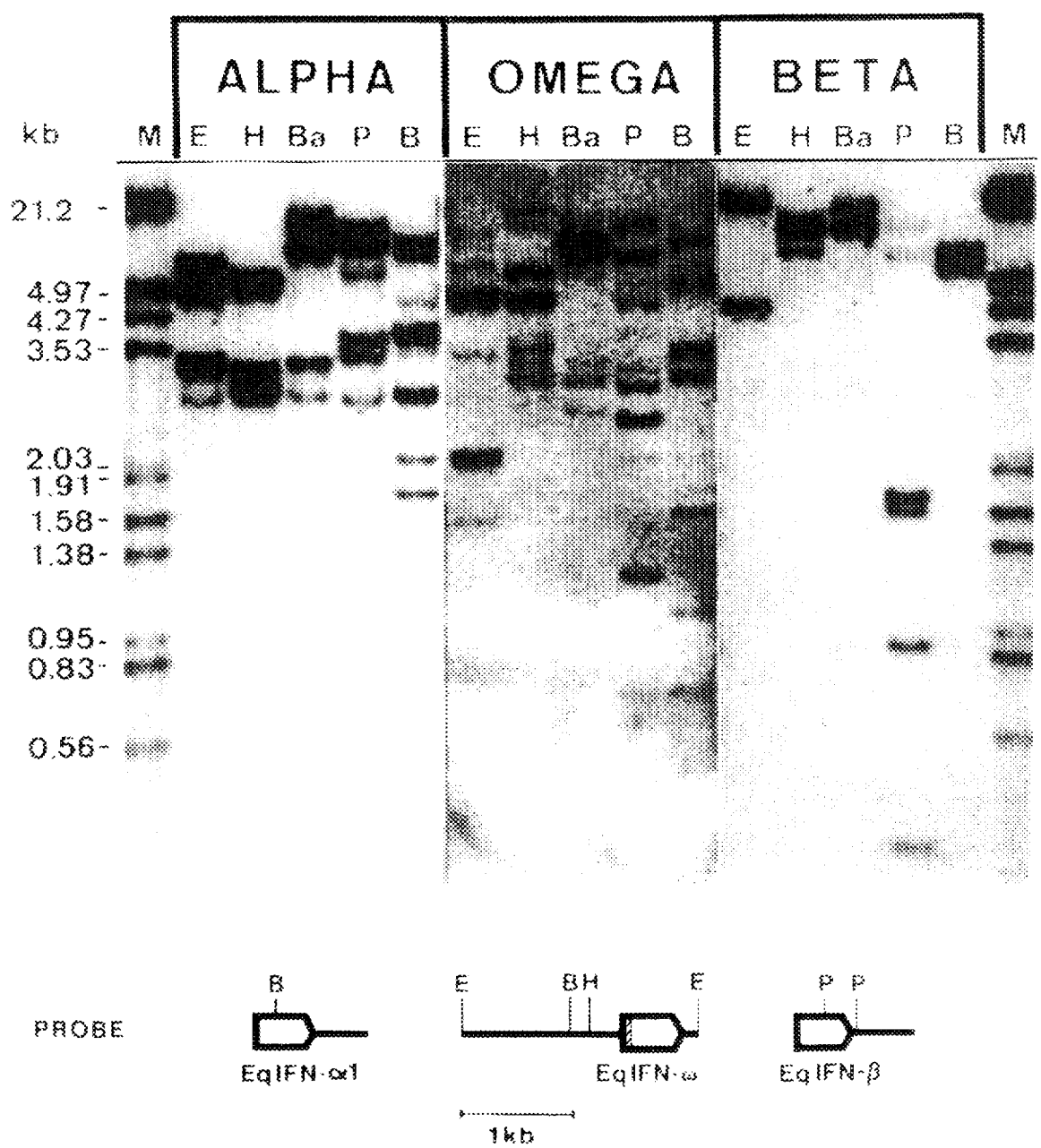
FIG. 18 is a Southern blot showing the hybridization maps resulting when alpha, beta and omega interferons from various species are probed with EqIFN-α1, EqIFN-β and EqIFN-ω, respectively.

In order to detect the total number of sequences in the horse genome which have high homology with interferon genes of classes IFN-α,IFN-β and IFN-omega, high-molecular weight horse DNA was totally digested with an appropriate restriction enzyme and this cut DNA was separated according to size. After southern transfer onto nitrocellulose filters, denaturing and fixing of the DNA, each filter was hybridised with nick-translated probe. The probe used for EqIFN- was a 1.0 kb long HindIII SphI fragment from plasmid pAH52, whilst the probe used for EqIFN-β was a 1.1 kb long HindIII/SphI fragment of plasmid pAH62, both of which contain the coding sequence for the entire mature interferon. The 2.1 kb EcoRI insert from plasmid pRH61 was used as a probe for EqIFN-omega. The filters were then washed under stringent conditions so that no cross-hybridisation can occur between these three interferon, sequences. Autoradiography was carried out on DuPont Cronex X-ray film using Kodak Lanex-Regular intensifier film for 7 days at −80° C. The results are shown in FIG. 18. It was surprisingly found that the horse genome contains at least 7 genes of the IFN-α class, at least 2 genes of the TFN-β class and at least 8 genes of the IFN-omega class.

In order to prepare the expression plasmid pRH 100, the plasmid pER 103 (Eva Dworkin-Rastl et al., Gene 21 (1983) 237–248, EP-A-0.115–613) was linearised with the restriction endonuclease HindIII and the 5' terminal phosphate residues were removed.

This plasmid DNA was mixed and ligated with the phosphorylated oligonucleotides d(AGCTTAAAGATGAGCT) and d(CATCTTTA). The ligase reaction was digested with the restriction endonuclease SacI and ligated by the addition of T4-PNK. The oligonucleotides were prepared analogously to the method described in EP-A-0.115–613.

Competent *E. coli* Hb101 was added to this ligase reaction and incubated.

Of the resulting bacterial colonies, 12 were chosen at random and the plasmids were isolated from them on a microscopic scale (Birnboim and Doly, Nucl. Acids Res. 7 (1979) 1513–1523). The resulting DNA was cut with the restriction endonuclease SacI and the DNA was separated on an agarose gel (1%, 1x TBE buffer). The migration of the DNA as a linear molecule measuring about 4,400 bp confirmed the introduction of a SacI-recognition site into the plasmid. One of these plasmids was arbitrarily sought out. *E. coli* HB101 was again transformed with the DNA from the associated mini preparation. From the resulting transformed bacteria a colony was selected and grown on a larger scale. The plasmid isolated from it was cut with the restriction endonucleases EcoRI and BamHI, the DNA was separated on a 1% agarose gel and the smaller fragment was isolated from the gel by electroelution. This EcoRI-BamHI DNA fragment about 460 hp long was sequenced according to Sanger. (F. Sanger et al., Proc. Natl. Acad. Sci. (1977) 5463–5467). The plasmid analysed in this way was designated pRH 100.

In order to prepare the expression plasmid pAH4/2, the plasmid pRH100 was totally cut with the restriction endonuclease BamHI and then the 5' terminal phosphate residues were removed with calves' intestinal phosphatase (CIP).

The plasmid pAH4 was digested with BamHI and a DNA fragment 0.6 kb long which contains the entire coding sequence for CaIFN-alpha1, was isolated and purified.

This 0.6 kb DNA fragment was ligated with the pRH100 vector DNA linearised with BamHI; competent *E. coli* HB 101 was transformed and spread on LB agar.

Figure 28:
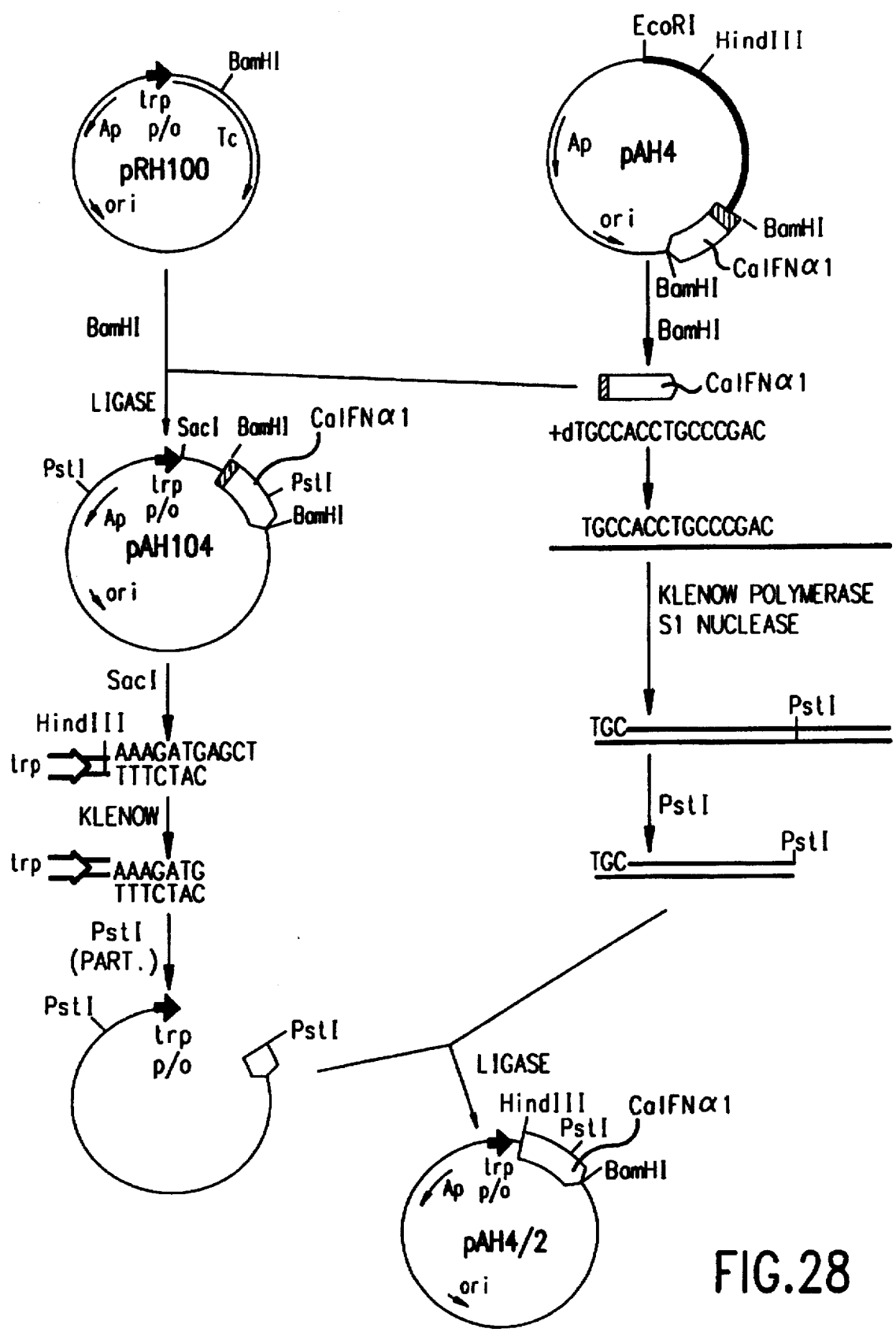
FIG. 28 diagrammatically describes the preparation of expression plasmid pAH4/2 for mature CaIFN-α1 from pRH100 and pAH4.

From the resulting bacterial colonies, plasmids were isolated on a microscopic scale and characterised by restriction analysis with various enzymes. A plasmid which contained the interferon gene and tryptophan promoter in the same orientation was designated pAH104 (FIG. 28). This plasmid constitutes an intermediate stage for the preparation of the final expression plasmid for mature CaIFN-alpha1.

The 0.6 kb long BamHI fragment from the plasmid pAH4 was mixed with synthetic oligonucleotide (5 'TGCCACCTGCCCGAC), prepared analogously to EP-A-0.115-613. The 15 mer oligonucleotide contains the coding sequence for the N-terminal 5 amino acids of the mature dog alpha-interferon. The DNA solution was heated and then cooled, whilst the oligonucleotide, present in a large excess, bonds to the complementary site of the DNA single strand.

Then the second strand was synthesised starting from the bonded oligonucleotide primer. The remaining single-strand DNA portions were removed with S1 nuclease. The DNA obtained was digested and then resolved by electrophoresis. DNA fragments with a length of about 300 pb were isolated and purified.

The plasmid pAH104 was digested and incubated with klenow polymerase in order to make the DNA ends blunt. The DNA obtained was partially cut, the DNA was resolved by electrophoresis and fragments with a length of 4.3 kb were isolated and purified.

The resulting DNA was ligated with the 0.3 kb long DNA fragment described hereinbefore. By means of this ligase reaction, E. coli B101 was transformed and spread on LB agar containing ampicillin.

The resulting bacterial colonies were transferred to fresh agar plates and in duplicate to nitrocellulose filters which had been placed on agar plates. After incubation, the bacteria were lysed in accordance with the procedure described by Grunstein and Hogness (M. Grunstein & D. Hogness, Proc. Natl. Acad. Sci. USA (1975) 72, 3961) and the DNA, after denaturing, was bonded to the nitrocellulose. The cell debris was removed. The filters were then hybridised with $^{32}$P-labelled oligodeoxynucleotide d(TGCCACCTGCCCGAC).

The filters were exposed on Kodak X-omat S X-ray film using Kodak X-omat regular intensifier films at −80° C. Plasmid DNA was isolated by a mini preparation process from bacterial colonies which yielded a positive hybridisation signal in the autoradiogram. The plasmids were completely cut with HindIII and BamHI. After electrophoretic resolution in an agarose gel, 0.5 kb long restriction fragments were isolated and subjected to DNA sequence analysis according to Sanger.

A plasmid having the desired structure was designated pAH4/2. It enabled the expression of mature CaIFN-alpha in E. coli.

In order to prepare the plasmid pAH4/3, the gene manipulated for the bacterial expression of CaIFN-alpha1 was subcloned from the plasmid pAH4/2 in a modified plasmid vector parpATER103 which has a higher copy number per cell and increased plasmid stability.

The HindIII/BamHI fragment of pAH4/2 0.5 kb long was cut with HindIII and BamHI and ligated with gel-purified plasmid vector parpATER103. Competent E. coli HB 101 was transformed with the ligase reaction and plated.

From the bacterial colonies produced, 6 were chosen at random and the plasmids were isolated from them on a microscopic scale. A plasmid which has the desired structure after restriction analysis with various restriction endonucleases was designated pAH4/3.

In order to detect the expression of the interferon activity by E. coli HB 101 which contain the plasmid pAH4/2 or pAH4/3, after incubation in a suitable culture medium the bacteria were broken open and the supernatent was sterilised by filtering and then tested for interferon activity in an assay which measures the cytopathic effect (CPE) of VSV. A-72 cells were used (ATCC CRL 1542, canine tumour) which had been infected with Vesicular stomatitis virus (VSV). The results are listed in Example K.

In order to detect the total number of sequences in the dog genome which have high homology with interferon genes of classes IFN-alpha and IFN-omega, high molecular dog DNA was completely digested with the corresponding restriction enzymes and cut DNA was separated according to size. After Southern Transfer to nitrocellulose filters, denaturing and fixing of the DNA, each filter was hybridised with nick-translated DNA probe.

As the probe for CaIFN-alpha, a 0.6 kb long BamHI fragment from plasmid pAH4 was used which contains the entire coding sequence for interferon. The 2.1 kb EcoRI insert of the plasmid pRH61 was used as a probe for EqIFNq-omega.

The hybridised filters were then washed under stringent conditions. Autoradiography was effected on DuPont Cronex X-ray film using Kodak Lanex Regular Intensifying film for 7 days at −80° C.

Figure 29:
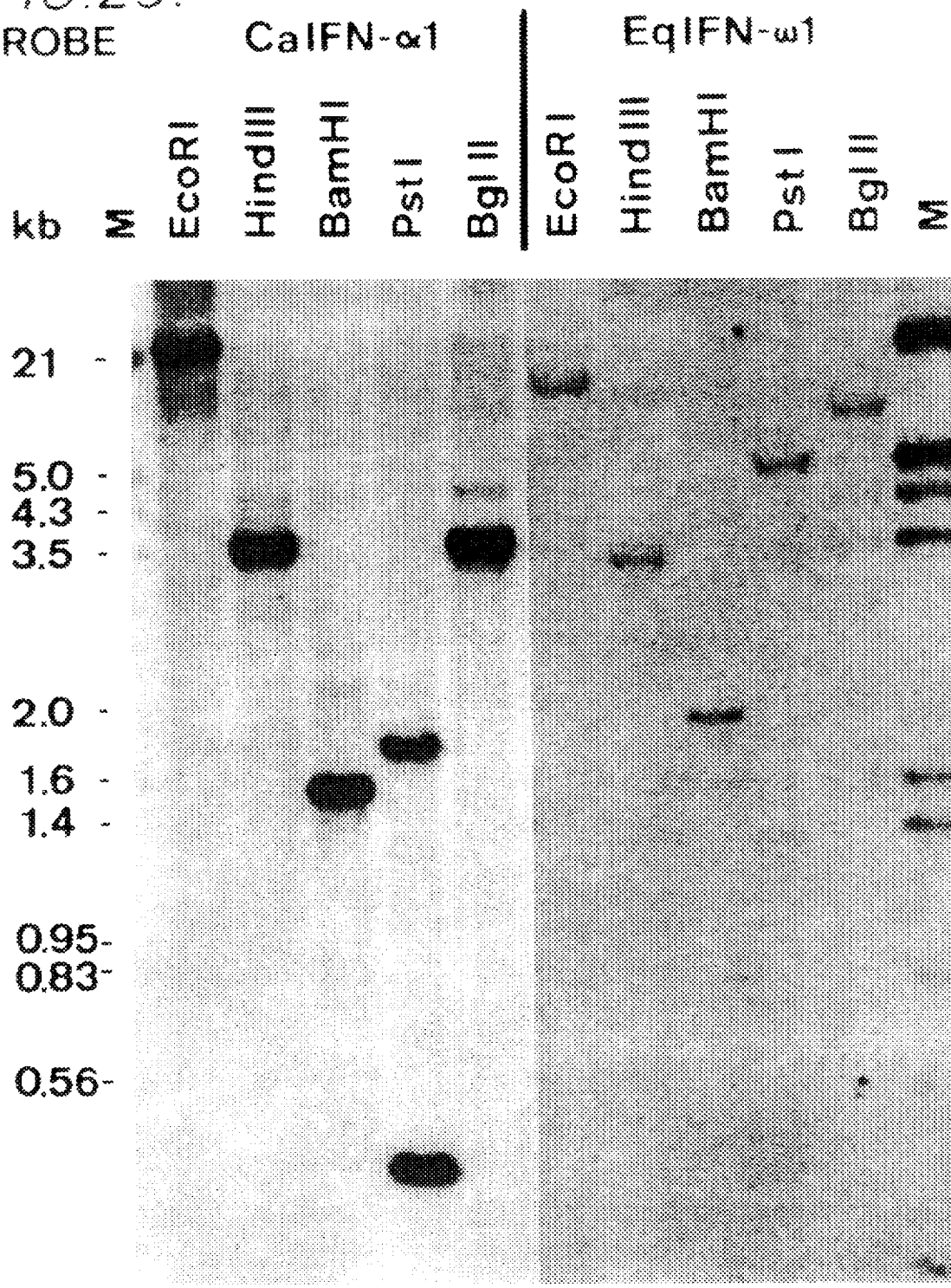
FIG. 29 is a DNA comparison of restriction fragments of CaIFN-α1 and EqIFN-ω1.

The autoradiogram (FIG. 29) shows that in the dog genome, apart from the two genes coding for identical alpha-interferons, no other sequences can be detected which show a similarly high degree of homology with CaIFN-alpha1 as occurs in other species within an interferon class. With the DNA for EqIFN-omega, at least one gene can be detected under less stringent conditions which is different from the alpha-interferons of the dog described.

Transformation of the cells with the vectors can be achieved by a number of methods. For example, it can be affected using calcium, either by washing the cells in magnesium and adding the DNA to the cells suspended in calcium or by subjecting the cells to a coprecipitate of DNA and calcium phosphate.

In the sequence genetic expression, the cells are transferred to media which select for transformed cells.

After the transformation of the host, expression of the gene and fermentation or cell cultivation have been carried out under conditions in which the proteins according to the invention are expressed, the product may usually be extracted by known chromatographic methods of separation in order to obtain a material which contains the proteins with or without leader and trailing sequences. The interferons according to the invention may be expressed with a leader sequence at the N-terminus (pre-IFN) which can be removed from some host cells. If not, the leader polypeptide (if present) must be split off in order to obtain mature IFN. Alternatively, the IFN clone may be modified so that the mature protein is produced directly in the microorganism instead of the pre-IFN. In this instance, the precursor sequence of the yeast mating pheromone MF-alpha-1 can be used in order to ensure correct "maturation" of the fused protein and precipitation of the products into the growth medium or the periplasmic space. The DNA sequence for functional or mature IFN can be connected with MF-alpha-1 to the supposed cathepsin-like cutting site (after Lys-Arg) at position 256 starting from the initiation codon ATG (Kurjan, Herskowitz, Cell 30, 933–943 (1982)).

Based on their biological spectrum of activity, the new interferons according to the invention may be used for any type of treatment for which the known interferons are used. These treatments include, for example, herpes, rhinovirus, equine/canine abortion virus, various types of cancer and the like. The new interferons may be used on their own or in conjunction with other known interferons or biologically active products, such as IFN-alpha, IL-2, other immuno modulators and the like.

The interferons according to the invention may be administered by the parenteral route in cases where an antitumour or antiviral treatment is required and in cases where immunosuppressive properties are present. The dosage and dosage rate may be similar to those currently used in clinical trials for IFN-α materials, e.g. about $(1-10)\times 10^6$ units per day and, in preparations which are more than 1% pure, up to $5\times 10^7$ units per day. For example, for a convenient dosage form with a substantially homogeneous IFN according to the invention produced by bacteria, for parenteral use, 3 mg of IFN-omega are dissolved in 25 ml of 5% animal serum albumin, preferably horse/dog serum albumin. This solution is then passed through a bacteriological filter and the filtered solution is aseptically distributed between 100 vials, each of which contains $6\times10^6$ units of pure IFN suitable for parenteral administration. Before use the vials are preferably stored under cold conditions (−20° C.). The substances according to the invention may be formulated in known manner in order to obtain pharmaceutically useful compositions, by mixing the polypeptide according to the invention with a pharmaceutically acceptable vehicle. Conventional vehicles and their formulations are described by E. W. Martin in Remington's Pharmaceutical Sciences, to which reference is expressly made. The interferons according to the invention are mixed with a calculated quantity of the vehicle in order to obtain pharmaceutical compositions which are suitable for effective administration to the patient. Preferably they are administered by parenteral route.

With the aid of the present invention it is thus possible for the first time for horses and dogs to be given interferons and the genetic sequences coding for them.

The invention relates specifically to:
proteins:
horse-alpha-interferons, substantially free from other proteins of animal origin.
  In substantially pure form
  Free from native glycosylation
  Containing a leader peptide
  Containing an amino acid sequence according to formula I or II or biologically active variants of these sequences
  Capable of being prepared by the process according to the invention.
Horse omega-interferons substantially free from other proteins of animal origin
  in substantially pure form
  free from native glycosylation
  containing a leader peptide
  containing an amino acid sequence according to formula III or biologically active variants of these sequences
  capable of being prepared by the process according to the invention. Horse β-interferons substantially free from other proteins of animal origin
  in substantially pure form
  free from native glycosylation
  containing a leader peptide
  containing an amino acid sequence according to formula IV or biologically active variants of these sequences
  capable of being produced by the process according to the invention.
Dog alpha-interferons substantially free from other proteins of animal origin
  in substantially pure form
  free from native glycosylation
  containing a leader peptide
  containing an amino acid sequence according to formula V or biologically active variants of these sequences
  capable of being produced by the process according to the invention.
DNA sequences:
  sequences coding for EqIFN-alpha
  sequences coding for EqIFN-alpha or degenerate variations of these sequences which are inserted into the HindIII cutting site of the plasmid pUC9
  the plasmid pAH50
  the plasmid pRH63
  sequences coding for EqIFN-alpha or degenerate variations of these sequences which hybridise with the inserts of the plasmids pAH50 or pRH63 under stringent conditions which show an homology of more than 85%, preferably more than 95%
  sequences for EqIFN-alpha or degenerate variations of these sequences which are contained in an expression vector which is replicatable in microorganisms, preferably in prokaryotes or eukaryotes and in mammalian cells
  the DNA sequence according to formula I or II or degenerate variations of these sequences
  sequences coding for EqIFN-omega
  sequences coding for EqIFN-omega or degenerate variations of these sequences which are inserted in the EcoRI cutting site of the plasmid pUC9
  the plasmid pRH61
  sequences coding for EqIFN-omega or degenerate variations of these sequences which hybridise with the inserts of the plasmid pRH61 under stringent conditions which show a homology of more than 85%, preferably more than 95%
  sequences coding for EqIFN-omega or degenerate variations of these sequences which are contained in an expression vector which is replicatable in microorganisms, preferably in prokaryotes or eukaryotes and in mammalian cells
  the DNA sequence according to formula III or degenerate variations of this sequence
  sequences coding for EqIFN-beta
  sequences coding for EqIFN-beta or degenerate variations of these sequences which are inserted in the HindIII cutting site of the plasmid pAH60
  the plasmid pAH60
  sequences coding for EqIFN-beta or degenerate variations of these sequences which hybridise with the inserts of the plasmid pAH60 under stringent conditions which show a homology of more than 85%, preferably more than 95%
  sequences coding for EqIFN-beta or degenerate variations of these sequences which are contained in an expression vector which is replicatable in microorganisms, preferably in prokaryotes or eukaryotes and in mammalian cells
  the DNA sequence according to formula IV or degenerate variations of this sequence
  sequences coding for CaIFN-alpha
  sequences coding for CaIFN-alpha or degenerate variations of these sequences inserted in the HindIII cutting site of the plasmid pAH2 or pAH4
  the plasmid pAH2
  the plasmid pAH4
  sequences coding for CaIFN-alpha or degenerate variations of these sequences which hybridise with the inserts of the plasmids pAH2 or pAH4 under stringent conditions which show an homology of more than 85%, preferably more than 95%
  sequences coding for CaIFN-alpha or degenerate variations of these sequences which are contained in an expression vector which is replicatable in microorganisms, preferably in prokarytes or eukaryotes and in mammalian cells
  the DNA sequence according to formula V or degenerate variations of this sequence.

Transformed host organisms:

which contain the genetic information coding for EqIFN-alpha, -omega or -beta or the genetic information coding for CaIFN-alpha, preferably prokaryotes, eukaryotes or mammalian cells, particularly E. coli or E. coli JM101 which contain the genetic sequences for the proteins according to the invention in a vector which replicatable in the host organisms.

Plasmids:

plasmid pAH51, characterised in that a DNA fragment 4.2 kb long of the plasmid pAH50 cut with HindII is provided with SphI linkers and after cutting with SphI is circularised plasmid pAH51/2, characterised in that it contains in the HindIII/BglII cutting site of the plasmid pAH51, instead of the longer fragment native to the plasmid, a fragment which has been obtained from the 0.4 kb long PvuII fragment of the plasmid pAH50, after being denatured in the presence of the 15 mer oligonucleotide primer

5'TGTGACCTGCCTCAC, extended with klenow fragment, the oligonucleotide complex

5'AGCTTAAAGATG
3'ATTTCTAC had been ligated and cut with HindIII and BglII.

Expression plasmid parpATER103, characterised in that a 0.47 kb long DNA fragment of the plasmid parpER33 partially cut with EcoRI and partially cut with HindIII is inserted into the EcoRI/HindIII cutting site of the plasmid pAT153.

Expression plasmid pAH52/2, characterised in that instead of the shorter fragment native to the plasmid, the 1.0 kb long HindIII/BamHI fragment of the plasmid pAH51/2 is inserted into the HindIII/BamHI cutting site of the plasmid parpATER103.

Expression plasmid pAH52, characterised in that instead of the shorter fragment native to the plasmid, the HindIII/SchI fragment of plasmid pAH51/2 is inserted into the HindIII/SphI cutting site of the plasmid parpATER103.

Expression plasmid pAH53, characterised in that the 2.4 kb long EcoRI/PvuII fragment of pBR322, straightened with klenow fragment and dephosphorylated, is ligated to a 1.1 kb long EcoRI/SphI fragment of plasmid pAH52 which has been blunted with klenow fragment.

Expression plasmid pAH55, characterised in that the plasmid pAH52/2 contains, instead of the shorter BglII/BamHI fragment native to the plasmid, the 1.0 kb long BglII/BamHI fragment of plasmid pRH63.

Plasmid pAH61, characterised in that, instead of the shorter fragment native to the plasmid, a 1.85 kb long DNA fragment of the plasmid pAH60 cut with HgiAI and straightened with T4-DNA polymerase and provided with SphI linkers and then cut with HindIII and SphI is inserted into the HindIII/SphI cutting site of the plasmid parpATER1.03.

M13pAH61, characterised in that the BamHI/SalI fragment of the plasmid pAH61, 1.3 kb long, is ligated with M13mp9-phage DNA which has been doubly digested with BamHI/SalI.

Expression plasmid pAH62, characterised in that a fragment of pAH61 which has been made double-stranded with the aid of the 15-mer

5'GTGAACTATGACTTG, treated with S1 nuclease, ligated with the oligonucleotide complex

5'AGCTTAAAGATG
3'ATTTCTAC and cut with HindIII and SphI is inserted into the HindIII/SphI cutting site of the plasmid parpATER103 instead of the shorter fragment native to the plasmid.

Expression plasmid pRH100, characterised in that the oligonucleotide complex

5'AGCTTAAAGATGAGCTCATCTTTA
/ ' ATTTCTACTCGAGTAGAAATTCGA is inserted into the HindIII cutting site of the plasmid pER103.

Plasmid pAH104, characterised in that it contains the coding sequence for the CaIFN-alpha1 in the BamHI cutting site of the plasmid pRH100.

Expression plasmid pAH4/2 characterised in that the coding sequence for mature CaIFN-alpha1 is inserted into the blunt ended SacI cutting site of the plasmid pAH104.

Expression plasmid pAH4/3, characterised in that the HindIII/BamHI fragment of plasmid pAH4/2, 0.5 kb long, is inserted into the HindIII/BamHI cutting site of the plasmid parpATER103.

Methods of producing these plasmids are also described:

Processes for preparing the plasmid pAH51, characterised in that the plasmid pAH50 is cut with HindII, the fragment 4.2 kb long is provided with SphI linkers, then cut with SphI and circularised with DNA ligase and the resulting plasmid is transformed for replication in E. coli HB 101 and cultivated.

Process for preparing the plasmid pAH51/2, characterised in that the plasmid pAH50 is cut with PvuII, the fragment 0.4 kb long is denatured in the presence of the 15-mer oligonucleotide primer

5'TGTGACCTGCCTCAC the primer bonded to the single strand is extended with klenow fragment, any possible 3' overhand is eliminated, the oligonucleotide complex

5'AGCTTAAAGATG
3'ATTTCTAC is ligated on, the resulting DNA fragment, after restriction endonuclease digestion with HindIII and BglII, is inserted into the HindIII/BglII cutting site of the plasmid pAH51 instead of the longer fragment native to the plasmid and the resulting plasmid is transformed for replication in E. coli HB 101 and cultivated.

Process for preparing the plasmid parpATER103, characterised in that a 0.47 kb long fragment of the plasmid parpER33 which has been totally cut with HindIII and partially cut with EcoRI is inserted by ligase reaction into the plasmid PAT153 which has been linearised by restriction endonuclease digestion with EcoRI and HindIII, and the resulting plasmid is transformed for replication in *E. coli* HB 101 and cultivated.

Process for preparing the expression plasmid pAH53/2, characterised in that the HindIII/BamHI fragment of the plasmid pAH51/2, 1.0 kb long, is inserted into the HindIII/BamHI cutting site of the plasmid parpTER103 instead of the shorter fragment native to the plasmid and the resulting plasmid is transformed for replication in E. coil HB 101 and cultivated.

Process for preparing the expression plasmid pAH52, characterised in that the HindIII/SphI fragment of the plasmid pAH51/2 is inserted into the HindIII/SphI cutting site of the plasmid parpATER103 instead of the shorter fragment native to the plasmid and the resulting plasmid is transformed for replication in *E. coli* HB 101 and cultivated.

Process for preparing the expression plasmid pAH53, characterised in that the EcoRI/PvuII fragment 2.4 kb long which has been blunted with klenow fragment and dephosorylated is ligated with a 1.1 kb long EcoRI/AphI fragment of the plasmid pAH52 which has been blunted with klenow fragment and the resulting plasmid is transformed for replication in *E. coli* HB 101 and cultivated.

Process for preparing the expression plasmid pAH55, characterised in that the BglII/BamHI fragment of the plasmid pRH63, 1.0 kb long, is inserted into the plasmid pAH52/2 instead of the shorter BglII/BamHi fragment native to the plasmid and the resulting plasmid is transformed for replication in *E. coli* HB 101 and cultivated.

Process for preparing the plasmid pAH61, characterised in that instead of the shorter fragement native to the plasmid a DNA fragment. 1.85 kb long, of the plasmid pAH60 cut with HgiAI which has been straightened with T4-DNA polymerase, provided with SphI linkers and then cut with HindIII and SphI is inserted into the HindIII/SphI cutting site of the plasmid parpATER103 and the resulting plasmid is transformed for replication in *E. Coli* HB 101 and cultivated.

Process for preparing M13pAH61, characterised in that the BamHI/SalI fragment 1.3 kb long of the plasmid pAH61 is ligated with M13mp9-phage DNA doubly digested with BamHI/SalI and transformed for replication in *E. coli* HB 101 and cultivated.

Process for preparing the expression plasmid pAH62, characterised in that a fragment of M13pAH61 which has been made double-stranded with the aid of the 15-mer

5'GTGAACTATGACTTG treated with S1 nuclease, legated with the oligonucleotide complex

5'AGCTTAAAGATG
3'ATTTCTAC and cut with HindIII and SphI is inserted into the HindIII/SphI cutting site of the plasmid parpATER103 instead of the shorter fragment native to the plasmid and the resulting plasmid is transformed for replication in *E. coli* HB 101 and cultivated.

Process for preparing the plasmid pAH4/2, characterised in that the sequence coding for mature CaIFN-alpha1 is inserted into the blunt-ended SacI cutting point of the plasmid pAH104 and the resulting plasmid is transformed for replication in *E. coli* HB 101 and cultivated.

Process for preparing the plasmid pAH4/2, characterised in that the BamHI fragment 0.6 kb long of the plasmid pAH4 is bonded to the oliogonucleotide primer

5'TGCCACCTGCCCGAC, synthesis of the second strand is effected using the klenow fragment, the remaining single strands are removed with SI nuclease, the DNA is cut with PstI and ligated, with the aid of DNA ligase, with the 4.3 kb long fragment of the plasmid pAH104, which is obtained after partial PstI digestion of the SacI fragment made blunt-ended with klenow polymerase.

Process for preparing the expression plasmid pRH100, characterised in that the plasmid pER103 is linearised using HindIII, ligated with the oligonucleotide complex

5'AGCTTAAAGATGAGCTCATCTTTA
3' ATTTCTACTCGAGTAGAAATTCGA, the ligase reaction is digested with SacI and then circularised and the resulting plasmid is transformed for replication in *E. coli* HB 101 and cultivated.

Process for preparing the expression plasmid pAH4/3, characterised in that the 0.5 kb long HindIII/BamHI fragment of the plasmid pAH4/2 is inserted in the HindIII/BamHI cutting site of the plasmid parpATER103 and the resulting plasmid is transformed for replication in *E. coli* HB 101 and cultivated.

The invention further relates to processes for preparing the proteins according to the invention:

Process for preparing EqIFN-alpha, -beta, -omega or CaIFN-alpha, characterised in that a) a host organism , preferably a prokaryote, eukaryote or a mammalian cell, particularly *E. coli* or *Saccharomyces cerevisiae*, is transformed with genetic information coding for EqIFN-alpha, -beta, -omega or CaIFN-alpha, preferably with the sequences from the plasmids pAH50, pAH62, pRH63, pRH61, pAH60, pAH2 or pAH4 coding for the proteins according to the invention or the sequences-hybridizing with these plasmids under stringent conditions which show a homology of more than 85%, preferaby more than 90%, more particularly sequences according to one of Formulae I to V or degenerate variations of these sequences, b) the coding sequence is contained in an expression vector, preferably in one of the expression vectors pAH52, pAH52/2, pAH53, pAH55, pAH62, pAH4/2 or pAH4/3 and this information is expressed in the host organism in order to produce EqIFN-alpha, -beta, -omega or CaIFN-alpha and c) the interferon EqIFN-alpha, -beta, -omega or CaIFN-alpha, preferably an interferon according to one of Formulae I to V, is isolated and purified.

The invention further relates to the use of the proteins according to the invention for therapeutic treatment and compositions for therapeutic treatment which contain an effective quantity of these proteins together with pharmaceutically inert vehicles.

The following examples, which should not restrict the invention, describe it in detail.

MATERIALS

Some of the starting materials were obtained commercially, some came from EMBL in Heidelberg. *E. Coli* JM101, pUC8, PUC9, M13mp8 and M13mp9 were obtained from the Bethesda Research Laboratories, the *E. coli* strains with the surpressor factor sufF, for example *E. coli* NM526, 538 and 539 and the vector lambda-EMBL3 or 3A where obtained from EMBL but in some cases could also be obtained from the firm Stehelin of Basle (Switerland).

A) Isolation of horse DNA

Frozen tissue, e.g. horse liver, was ground to a fine powder in liquid nitrogen and incubated for 3 hours at 55° C. in 0.5EDTA, 10 mM Tris-HCl pH 8.0, 0.5% SDS, 0.1 mg/ml of protease K (20 ml/g of tissue). The viscous solution obtained was freed from protein by phenol extraction and extracting 3 times with phenol/chloroform/isoamyl alcohol (25/24/1 Vol), dialysed with 50 mM Tris-HCl, pH 8.0, 10 mM EDTA, 10 mM NaCl and the DNA was precipitated with 2 volumes of ethanol. After total drying in vacuo, the DNA was put into solution at 4° C. in TE buffer (10 mM Tris-Hcl, pH 8.0, 1 mM EDTA) and centrifuged for 62 hours at 40,000 rpm at 20° C. With 1.273 g of CsCl/ml of solution (Sorvall 50Ti-Rotor). The CsCl gradient was dripped out, the fractions containing DNA were dialysed with TE buffer and the DNA w as then precipitated with 2 volumes of ethanol, washed with 70% ethanol, dried and again dissolved in TE buffer (4° C.).

The finished DNA preparation was free from RNA and longer than 50 kb (determined by electrorhoresis on a 0.45% agarose gel).

B) Partial endonuclease digestion and size fractionation of horse DNA

Twice 50 mcg horse DNA was incubated at 37° C. with 1.6 units of Sau3A in 450 mcl of reaction medium (10 mM Tris-Hcl, pH 7.5, 10 mM MgCl$_2$, 1 mM dithiothreitol). After 15, 25 and 40 minutes, 150 mcl aliquots were taken and mixed with 15 mM EDTA and the reaction was stoped by heating to 70° C. for 10 minutes. After the addition of 0.3M Na acetate pH 6.0, the DNA was precipitated with 2.5 volumes of ethanol. After dissolving in TE buffer again, the DNA was separated according to size by electrophoresis overnight on a 0.45% agarose gel in TBE buffer (10.8 g/l Tris, 5.5 g/l boric acid, 0.93 g/l (Na$_2$EDTA) at about 1 V/cm. Using size markers (lambda-DNA doubly digested with EcoRI and HindIII and digested with HindIII) the gel fragment with DNA 10–23 kb long was cut out, the DNA was electrically eluted from the gel in a dialysis tube for 3 hours at 300 V (buffer 0.1×TBE), purified on an elutip-D column (Schleicher and Schüll) according to the manufacturers' instructions and then precipitated with ethanol.

In order to prevent self-ligation of horse DNA fragments, which may lead on the one hand to artifical hybrids of horse DNA sequences and on the other hand to excessively large DNA fragments which can therefore no longer be packaged in lambda phages, the size-fractionated horse DNA fragments were dephosphorylated.

To do this, the DNA was incubated for 30 minutes at 37° C. in 140 mcl of reaction medium (50 mM Tris-Hcl, pH 9.5, 1.0 mM of MgCL$_2$ 0.1 mM of Zn acetate, 1 mM of spermidine) with 5 units of bovine intestinal phosphatase, a further 5 units of enzyme were added and the whole was incubated for 30 minutes.

After the addition of EDTA to give a final concentration of 25 mM, the DNA was extracted once with phenol/chloroform/isoamyl alcohol (25/24/1 vol), twice with chloroform/isoamyl alcohol (24/1 vol) and 3 times with diethylether, then precipitated with ethanol, dried and dissolved in 0.1×TE buffer.

C) Construction of the horse genome-DNA library

The dephosphorylated horse DNA fragments 10–23 kb long were cloned in a lambda vector, for example lambda-EMBL3 or 3A (3) with G-A-T-C cohesive ends obtained by removing the internal BamHI fragment of the phage DNA.

The vector was grown in an *E. coli* strain with the suppressor factor sup F for example *E. coli* NM526, 538 or 539 (3), in LB broth (20) with 5 mM of MgSO$_4$, precipitated with polyethyleneglycol and purified by CsCl-densitity gradient centrifuging twice (0.71 g of CsCl/ml of solution, 40 hours at 45,000 rpm, 20° C.). After dialysis with TE buffer, the phage DNA was freed from protein by extracting twice with phenol/chloroform/isoamyl alcohol (25/24/1 Vol) and extracting twice with chloroform/isoamyl alcohol (24/1 vol) and concentrated by ethanol precipitation.

In order to obtain the end fragments of EMBL3A, 50 mcg of phage DNA were totally digested with BamHI for two hours at 37° C. in 450 mcl of reaction medium (10 mM Tris-Hcl, pH 7.5, 10 mM MgCl$_2$, 1 mM dithiothreitol) then digested with 15 mM EDTA for 10 minutes, then at 70° C. the reaction was stopped and the DNA was precipitated with ethanol.

In order to avoid re-ligation, the middle fragment was cut again with with EcoRI and the oligonucleotide falling away was eliminated by isopropanol precipitation.

The BamHI-digested lambda-DNA was totally digested for 2 hours with EcoRI at 37° C. in 450 mcl of 10 mM Tris-Hcl, pH 7.5, 100 mM NaCl, 10 mM MgCl$_2$ and the reaction was stopped by adding 15 mM EDTA and heating to 70° C. for 10 minutes. After the addition of Na-acetate to give a final concentration of 0.3M, the three large DNA fragments were precipitated with 0.6 volumes of isopropanol for 15 minutes at 0° C., washed twice, with 0.45M Na-acetate/0.6 volumes of isopropanol and once with 0.3M Na-acetate/2.5 volumes of ethanol and dissolved in 15 mcl of 0.1×TE buffer. The BamHI/EcoRI linkers remain in solution during this procedure.

The EMBL3A fragments (8 mcg) were combined with about 5 mcg of 10–23 kb horse DNA and 10 units of T4-DNA ligase (NEN) and incubated overnight at 14° C. and for 1 day at 4° C. in 50 mcl of ligation medium (66 mM Tris-Hcl, pH 7.2, 0.1M NaCl, 10 mM MgCl$_2$, 1 mM EDTA, 5 nM dithiothreitol, 0.5 mM ATP). The ligated DNA mixture was packed into mature lambda-phage particles using an in vitro lambda packing system (27).

The components of this system, i.e. ultrasound extract (SE), freeze-thaw lysate (ETL), buffer M1 and A were prepared according to reference (27). 10 mcl of aliquots of the ligated DNA mixture were incubated for 2 minutes at ambient temperature with 25 mcl of SE which, like the FTL, had thawed for 30 minutes from ice, then 100 mcl of FTL were added and the mixtured was reincubated for 60 minutes at ambient temperature. The packaging mixture was diluted with 150 mcl of lambda dieluant (100 mM of Tris-HCl, pH 7.5, 10 mM MgSO$_4$, 1 mM EDNA) and stored at 4° C.

A small amount of the packaged lambda phages was tritrated on the *E. coli* strain NM 528 SupF. In all, the process yielded about 1×10$^6$ independent horse DNA recombinants. The remainder of the packaged material was multiplied by plating on NM 528 in a density of 30,000 plaque-forming units (pfu) per 13.5 cm of LB/MgSO$_4$ agar plate.

D) Screening of the horse gene library for interferon genes

In order to identify the recombinant phages which contain dog interferon genes, the nucleotide homology demonstrated by Souther-Blots (17) with radioactively labelled human IFN-alpha genes was used.

10 mcg of high molecular horse DNA was totally digested with EcoRI or HindIII, resolved by electrophoresis on 0.8% agarose gel and transferred to nitrocellulose filters. A P-32-labelled DNA fragment was prepared by conventional methods (25) from an 845 bp HindIII fragment originating from the expression plasmid pER33 (14) and containing the entire protein-coding region for mature human interferon-alpha 2ARG.

For screening for equine beta-interferon genes, a radioactively labelled DNA probe was prepared as above from a 363 pb PstI-BglII fragment of a cDNA clone P1F12 (15) coding for human beta-interferon. This probe codes for amino acids 48–166 of mature beta-interferons.

Figure 1:
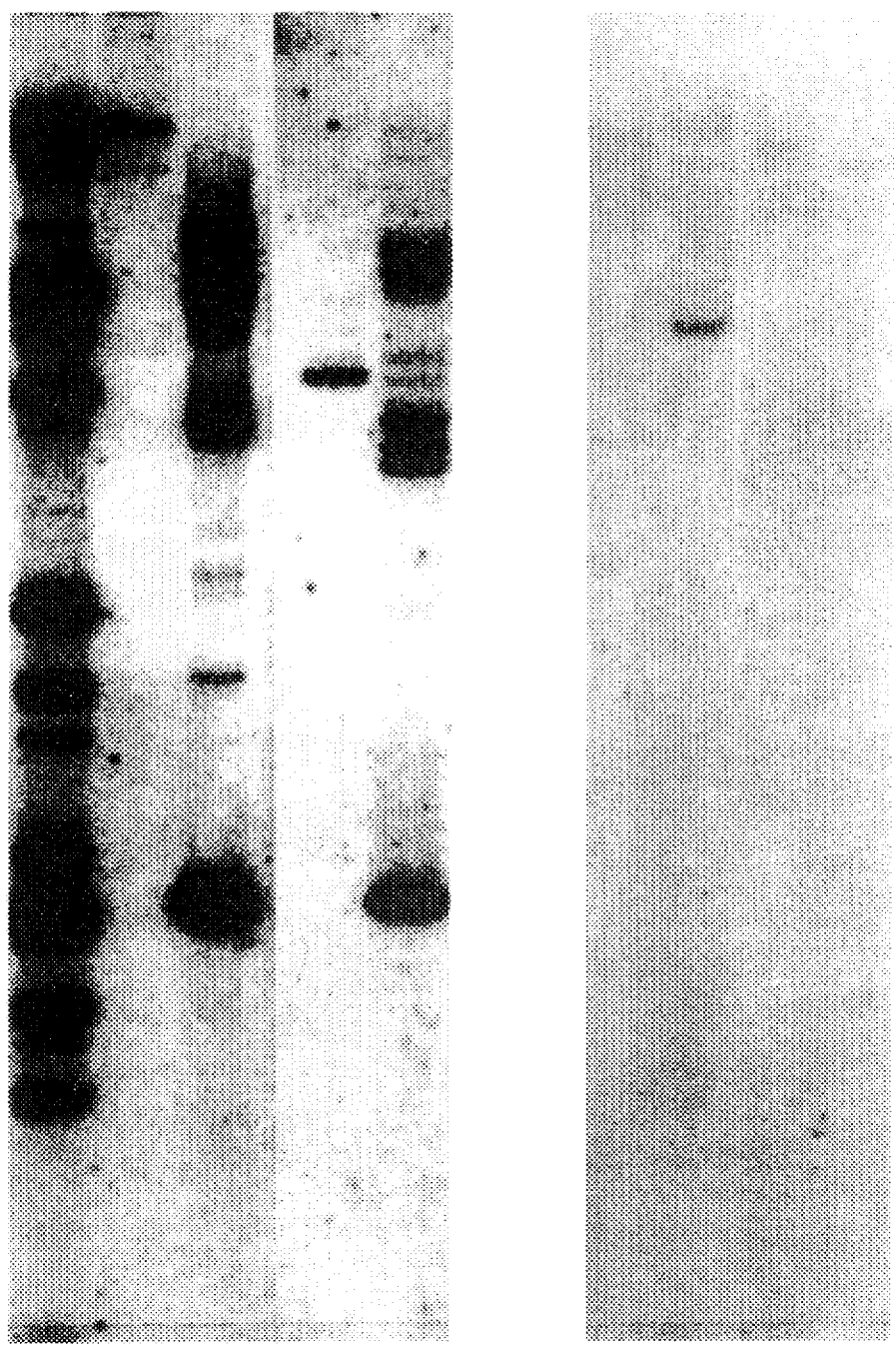
FIG. 1 is an autoradiogramn showing the family of alpha and beta interferon genes in horse, using as a probe the region encoding the mature human interferon α2 and β proteins.
Figure 2B:
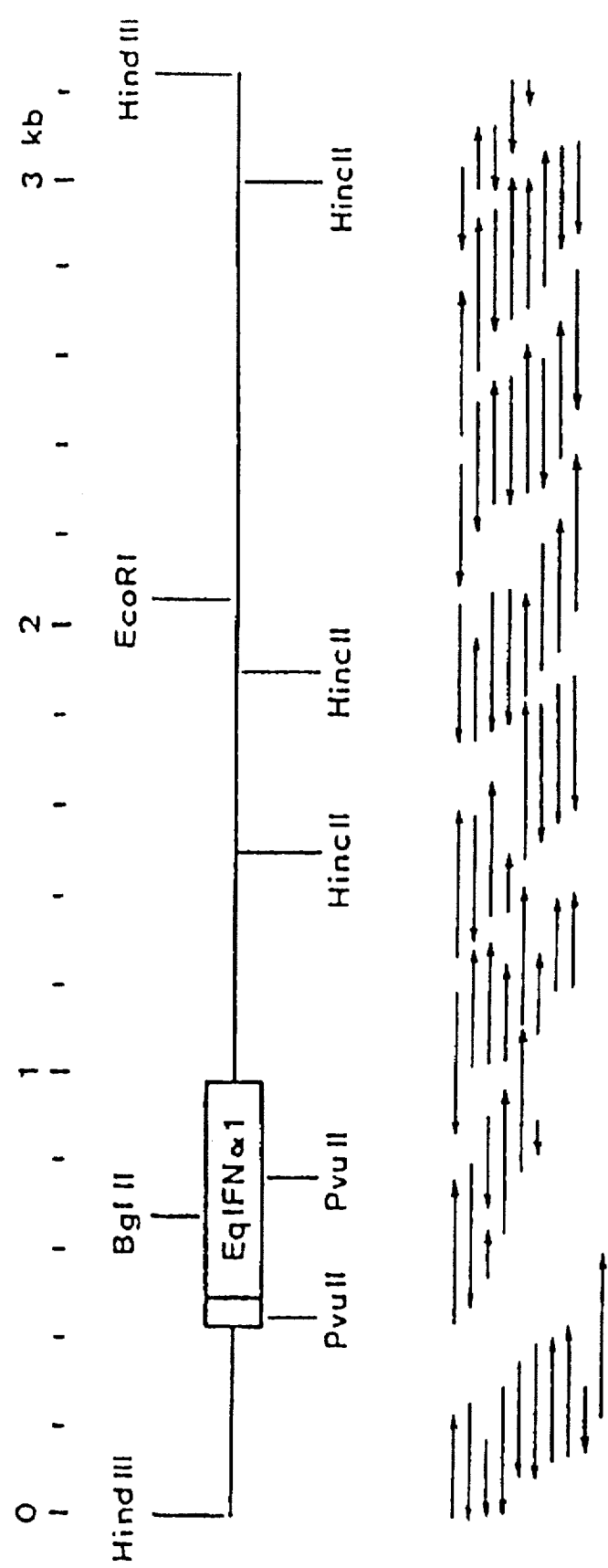

The nitrocellulose filters were prehybridized for 7 hours at 65° C. in 5×SSPE (0.9M NaCl, 50 nM $NaH_2PO_4$, 5 mM EDTA, pH 7.4), 5 x Denhart solution (0.1% ficoll, 0.1% polyvinylpyrrolidone, 0.1% bovine serum albumin), 0.1% SDS, 20 mg/ml of salmon sperm DNA and then hybridized with $13 \times 10^6$ cpm of the labelled probe in the same solution but without the salmon sperm DNA. After incubation over night at 65° C., the filters were washed 4 times for 1 to 1.5 hours in 3×SSC (0.45M NaCl, 45 mM Nacitrate), 0.1% SDS at 65° C. and exposed for 7 days on Kodak X-omat S-X-ray film with Kodak regular intensifier films (FIG. 1). The appearance of several bands indicates a family of alpha-interferon genes in horses, as had earlier been detected in cattle, pigs and humans.

Therefore, the same hybridizing conditions were used for screening the interferon genes in the horse DNA library.

600,000 recombinant lambda phages were plated on *E. coli* NM528 in a density of 30,000 pfu/13.5 cm of plate. Four-fold nitrocellulose replicas were prepared from each plate using the method described by Benton and Davis (19).

After 2 hours' baking at 80° C. the filters were washed for 1.5 hours at 65° C. in 1M NaCl, 10 mM Tris-HCl, pH 8.0, 0.1% SDS, prehybridized overnight as described above and 2 filter replicas from each plate were hybridized for 24 hours with $1.5 \times 10^6$ cpm of radioactive alpha-interferon probe or $1 \times 10^6$ cpm beta-interferon probe per filter. After screening had been repeated 3 times, 8 horse alpha-interferon clones and 6 horse beta-interferon clones were obtained which gave positive hybridization signals.

E) Characterisation of the recombinant phages

Phage DNA was prepared from 7 recombinants hybridizing with human alpha-IFN and 3 recombinants hybridizing with human beta-IFN. The DNA's were digested with EcoRI, BamHI, HindIII, PstI, BglII, SalI and SmaI and separated electrophoretically in a 0.8% agarose gel. The size of the hybridizing fragments was determind by the Southern method. The position of the restriction sites within the lambda insert was determined using a method described by Rackwitz et al. (4) after partial restriction digestion of the lambda DNA, labelling of the right or left sticky ends of the lambda arms with synthetic P-32-labelled oligonucleotides and electrophoresis in 0.45% agarose gels. The resulting restriction maps of the clones Eq-alpha1, Eq-alpha16, Eq-alpha20 and Eq-beta6 are shown in FIGS. 2A–2B, 3A–3B and 9.

F) Subcloning of the horse interferon alpha gene

A restriction fragment of the clone Eq-alpha1, which had hybridized with the human alpha-interferon marker, was subcloned in the multiple restriction enzyme cloning site of the pBR322 derivative pUC9. Insertion of a foreign DNA fragment leads to an interruption in the lac Z gene of beta-galactosidase and thus alters the phenotype of the *E. coli* strain JM101, transformed with the plasmid, from lac+ to lac−. Owing to the non-functioning beta-galactosidase, JM101 induced with isopropyl thiogalactoside (IPTG) cannot cleave the colourless substrate analoge 5-bromo-4-chloro-3-indolyl-β-D-galactoside (BCIG) to give the blue dye. Bacteria colonies with lac− phenotype can therefore be recognised by their white color.

A 3.2 kb HindII fragment of the clone Eq-alpha1 was eluted from an agarose gel, purified on an elutip-D column and ligated in an approximately 10-fold molar excess with 40 mg of pUC9 vector cut with SmaI and dephosphorylated, then transformed in *E. coli* JM101 and poured out with LB top agar with 0.2 mg/ml of BCIG, 0.17 mg/ml of IPTG and 01 mg/ml of ampicillin. White colonies were grown in 5 ml of LB broth with 0.1 mg/ml of ampicillin over night at 37° C. and screened for the inserted fragment by a plasmid minipreparation method (25). A plasmid thus obtained was designated pAH50.

G) DNA sequence of horse alpha-interfron genes from the clone Eq-alpha1

The 3.2 kb HindIII insert of pAH50 (3.2 kb HindIII fragment subclone of Eq-alpha1, FIGS. 3A–3B) was sequenced by the dideoxy method described by Sanger (23) using the shotgun process. 60 mcg of pAH50 plasmid DNA were totally digested with HindIII, the 3.2 kb fragment was isolated from a 1% agarose gel and purified as described above.

15 mcl of this fragment were ligated with itself in 100 mcl of ligation medium with 14 units of $T_4$-DNA ligase overnight at 14° C. and for a further 4 days at 4° C. This ligated DNA was divided into small pieces in an ice bath with ultra sound in 20 second pulses a total of 100–140 seconds. The DNA ends were repaired with 15 units of the large fragment of *E. coli* polymerase I (klenow fragment) for 2 hours at 14° C. in 250 mcl of reaction medium (50 mM Tric-Hcl, pH 7.5, 10 mM $MgCl_2$, 1 mM dithiothreitol, 0.5 mg/ml of bovine serum albumin per 0.1 mM dATP, dGTP, dCTP, dTTP). After concentration by ethanol precipitation, the DNA pretreated in this way was separated on a 1% agarose gel and DNA fragments in the size range from 0.35 to 1.0 kb were isolated and purified. The fragments were ligated in an approximately 10-fold molar excess with the replicative form of bacteriophage M13mp8 (22) cut with SmaI and dephosphorylated, and were then transformed with *E. coli* JM101. The single strand DNA of the recombinant phages thus obtained was isolated and after the bonding of a synthetic oligonucleotide, synthesis of the second strand was carried out in four individual reactions with the klenow fragment of *E. coli* DNA-polymerase I.

The sequences of the inserts of the various recombinant phages were combined with the aid of a computer programme of Staden (24) modified by C. Pieler to form a total sequence which is shown in FIGS. 4A–4C.

H) Subcloning of the horse β-interferon gene

Figure 3B:
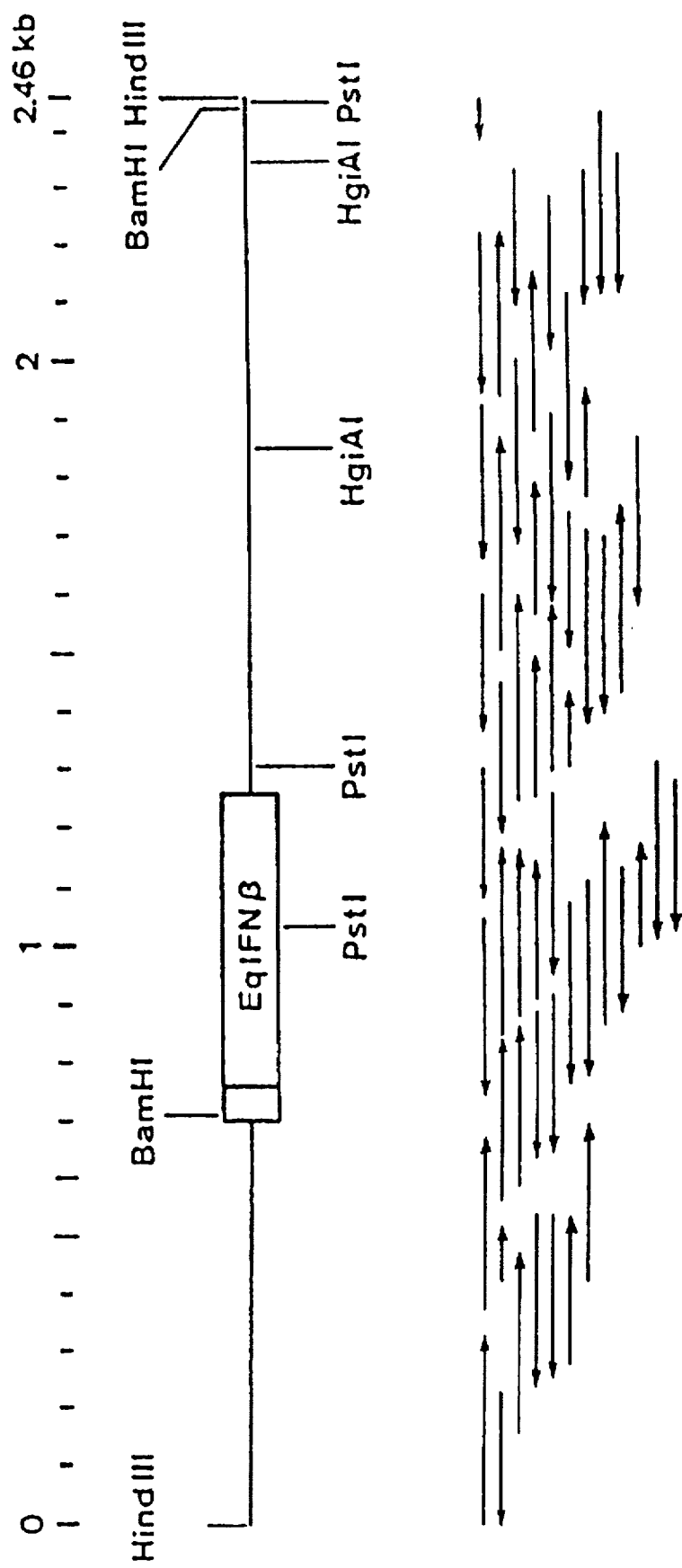

For subcloning of the horse β-interferon gene identified in the lambda clone Eq-beta6, the same procedure was used as in F. A 4.5 kb PvuII fragment which hybridized with the human beta-interferon probe was isolated and purified and ligated into the SmaI restriction site of the plasmid pUC9 with smooth ends and transformed in *E. coli* JM101. A transformant with the desired insert (pAH60) was grown and the plasmid was characterised more precisely by southern analysis. The restriction map obtained is shown in FIGS. 3A–3B. The 2.5 kb HindIII fragment was sequenced analogously to G) using the dideoxy method of Sanger. The total sequence of the 2.5 kb fragment shown in FIGS. 8A–8C was composed of 52 individual sequences.

I) Subcloning and sequencing of the horse interferon gene from clone Eq-alpha16

A 3.3 kb long EcoRI restriction fragment from the lambda clone Eq-alpha16 which had hybridised with a human alpha-IFN marker (see example D, E) was subcloned into the EcoRI site of the plasmid pUC8. A plasmid obtained was designated pRH63. Using a restriction map drawn up (FIG. 9) defined restriction fragments were subclone in controlled manner into M13 phages and the DNA sequence was determined according to the Sanger method (FIGS. 10A–10B).

J) Subcloning and sequencing of the horse interferon gene from clone Eq-alpha20

A 2.2 kb long EcoRI fragment of the lambda clone Eq-alpha20 which had hybridized weakly with the human alpha-IFN probe was subcloned into the EcoRI site of the plasmid Puc9. A clone obtained was designated pRH61 (FIG. 9). The entire 2.2 kb EcoRI insert was isolated and the DNA sequence was determined using the shotgun process by the Sanger method (Example G) (FIGS. 12A–12C).

K) Preparation of the expression plasmid parpATER103

Starting from the expression plasmid parpER33, the "par" sequence responsible for increased plasmid stability in *E. coli* and the tryptophan promoter-operator sequence together with the artificial ribososomal bonding site were inserted into the plasmid vector pAT153 (Amersham). pAT153 is a shortened derivative of the plasmid, pBR322, which lacks a portion required for the mobilizing of DNA (36).

The procedure for preparing the plasmid parpATER103 is shown in FIG. 13. The plasmid parpER33 was completly cut with HindIII and partially cut with EcoRI, the resulting 0.47 kb long DNA fragment was isolated from an agarose gel and purified and ligated with pAT153 which had been doubly cut with EcoRI and HindIII. A plasmid of the desired structure obtained after transformation of *E. coli* HB101and determined by digestion with various restriction enzymes was designated parpATER103.

L) Direct expression of mature Eq-IFN-alpha1 in *E. coli*

The preparation of the expression plasmids pAH52, pAH52/2 and pAH53 and the preliminary stages thereof is shown in FIGS. 14A–14C. 20 mcg of the plasmid pAH50 (Example F) were digested with 30 units of HindII (Boehringer Mannheim) and the 4.2 kb long DNA fragment which contains the entire Eq-IFN-alpha1 gene was isolated from an agarose gel with DE81 paper (Whatman) and purified. To do this, after separation of the DNA fragments in agarose gel, a slot was cut in front of and behind the DNA band which was to be isolated and a strip of DE81 paper was inserted into the slot. Electrophoresis is continued until the desired DNA fragment is totally bonded to the front DE81 strip. The back DE81 strip prevents contamination by larger DNA fragments. The DE81 paper with the bonded DNA fragment is washed twice for 5 minutes in 400 mcl of low salt buffer (0.2M NaCl, 25 mM Tris-HCl, pH 8.0, 1 mM EDTA) and then the DNA is eluted twice from the DE81 paper over a period of 10 minutes with 200 mcl of high salt buffer (1M NaCl, 25 mM Tris-Hcl, pH 8.0, 1 mM EDTA) and precipitated with 1 ml of ethanol. The ends of the HindII fragment were provided with SphI linkers.

For this, 0.2 mcl of SphI linker (Worthington) were incubated with 2 units of polynucleotide kinase in 10 mcl of reaction medium for 45 minutes at 37° C. (70 mM Tris-Hcl, pH 7.6, 10 mM MgCl$_2$, 1 mM ATP, 5 mM dithiothreite). The kinase SphI linkers and the HindII fragment were ligated with 8 units of T4-DNA ligase for 20 hours at 4° C. Then the enzyme was deactivated at 70° C. or and the DNA was digested with 30 units of SphI in a total volume of 100 mcl, extracted with phenol and chloroform and precipitated with ethanol. The DNA was circularised with ligase and transformed with *E. coli* HB101. A plasmid of the desired structure was designated pAH51. It contains the Eq-IFN-alpha1 gene with a shortened 3'-non-translated region and an additional SphI cutting site.

In order to connect the DNA sequence for the mature horse alpha-interferon to the promoter sequence at the correct distance in the final structure, a 0.4 kb long DNA fragment was used as starting material, which was isolated from 20 mcl of plasmid pAH50 cut with PvuII. 1 nmol of synthetic 15 mer oligonucleotide with the sequence 5'-TGTGACCTGCCTCAC was phosphorylated with polynucleotide kinase. It contains the sequence which codes for the first five amino acids of mature Eq-IFN-alpha1 from clone pAH50. The 15 mer was mixed with about 7 pmol of the 0.4 kb PvuII fragment and boiled for 5 minutes in a total volume of 34 mcl in order to denature the DNA double strand. After cooling, the oligonucleotide primer bonded to the single strand was extended with 30 units of klenow fragment for 3 hours at 37° C. in 70 mcl of reaction medium (50 mM Tris-HCl, pH 7.2, 10 mM MgSO$_4$, 0.1 mM dithiothreitol, 50 mcg/ml bovine serum albumin, 1 mM each of dATP, dGPT, dCTP and dTTP. In order to ensure that any remaining 3' overhang was removed, the DNA was then incubated with 16 units of T4 DNA polymerase for 20 minutes at 37° C. in 120 mcl of reaction medium (33 mM Tris-acetate, pH 7.9, 66 mM KAc, 10 mM Mg(Ac)$_2$, 0.5 mM dithiothreitol, 0.1 mg/ml of bovine serum albumin, 1 mM each of dATP, dGTP, dCTP and dTTP). The resulting DNA with blunt ends was extracted with phenol and chloroform and precipitated with 0.45M of Na-acetate and 0.6 parts by volume of 2-propanol for 15 minutes at 0° C. A mixture of 2 phosphorylated oligonucleotides complimentary to each other, namely 12 mer 5'-AGCTTAAAGATG, and 8 mer 5'-CATCTTTA was ligated to this DNA fragment, this mixture producing a HindIII cutting site and the translation start codon ATG. 1 nmol batches of the two oligonucleotides were ligated to the DNA fragment in 20 mcl with 14 units of ligase for 40 hours at 4° C. after deactivation of the enzyme at 70° C., the DNA obtained was cut in 100 mcl with 80 units of HindIII and 20 units of BglII and DNA fragments about 190 bp long were isolated from a 2% agarosegel with DE81 paper and purified. The resulting DNA fragment was ligated with about 50 ng of pAH51 vector doubly cut with HindIII and BglII and transformed with *E. coli* HB101.

Of 65 colonies obtained, a HindIII/BamHI DNA fragment was isolated from four plasmids having the desired restriction pattern and this fragment was sequenced by the Sanger method, whereby two clones having precisely the desired sequence were obtained. Such a plasmid was designated pAH51 /2. It contains the sequence for mature EqIFNα1 with a preceding translation start codon ATG and HindIII cutting site.

Preparation of the expression plasmids pAH52 and pAH52/2

20 mcg of plasmid pAH51/2 were doubly cut with SphI and HindIII, the resulting DNA fragment 1.0 kb long was isolated from an agarose gel and ligated with plasmid parpATER103 doubly cut with 40 ng of HindIII and SphI (Example K). A plasmid of the desired structure obtained after transformation of *E. coli* HB101 was designated pAH52. It contains all the information required for inducible expression of mature EqIFN-α1. Analogously, the plasmid pAH52/2 was prepared from pAH51/2 doubly cut with HindIII and BamHI and parpATER103 cut with HindIII/BamHI. This expression plasmid is about 0.2 kb larger than pAH52 and additionally has a single BamHI cutting sight.

Preparation of the plasmid pAH53

A substantially smaller expression plasmid for preparing mature EqIFN-α1 in *E. coli* in which the tryptophan promoter, the interferon gene, ampicillin resistance gene and replication origin are oriented in one direction was prepared from the plasmids pAH52 and pBR322. 10 mcg of pAH52 were cut with SphI and EcoRI, the enzymes were deactivated at 70° C. and the DNA ends were made blunt with klenow fragment after the addition of 0.15 mM of dATP, dGTP, dCTP and dTTP over a period of one hour at 22° C.

The DNA fragments were fractionated according to size on agarose gel and a fragment 1.1 b long was isolated which contains the promoter and interreron gene. 10 mcg of pBR322 plasmid were doubly digested with EcoRI and PvuII, the ends were blunted with klenow fragment as described above and then dephosphorylated with calves intestinal phosohatase. A DNA fragment 2.4 kb long was isolated from an agarose gel. The two DNA fragments thus obtained were ligated with T4 DNA ligase and *E. coli* HB101 was transformed. A plasmid thus obtained in which two EcoRI recognition sites were created was designated pAH53.

M) Preparation of an expression plasmid for EqIFN-2 (pAH55)

Owing to the high homology of the genes for EqIFN-α1 (pAH50) and EqIIFN-α2 (pRH63, FIGS. 11A–11D) it is possible to prepare an expression plasmid for EqIFN 2 (FIG. 15) from the expression plasmid pAH52/2 (Example L) and the lambda subclone pRH63. 20 mcg of pRH63 plasmid were cut twice with BglII and BamHI and the resulting DNA fragment 1.0 kb long which contains the coding sequence for EqIFN-α2 from the 64 amino acid onwards was isolated from an agarose gel. 10 mcg of the plasmid pAH52/II were also cut with BglII and BamHI, the ends were dephosphorylated with calves' intestinal phosphatase and the larger of the two DNA fragments produced was obtained from an agarose gel. This DNA fragment contains the plasmid vector component, the promoter and the coding sequence for the first 63 amino acids of the mature interferon. The two DNA fragments described were ligated with ligase and *E. coli* HB101 was transformed. A plasmid thus obtained which contains the insert in the correct orientation (capable of being cut with BamHI and BglII) was designated pAH55. This plasmid makes it possible to express mature EqIFN-α2 in *E. coli*.

N) Preparation of an expression plasmid for mature EqIFN-β (pAH62)

Figure 16A:
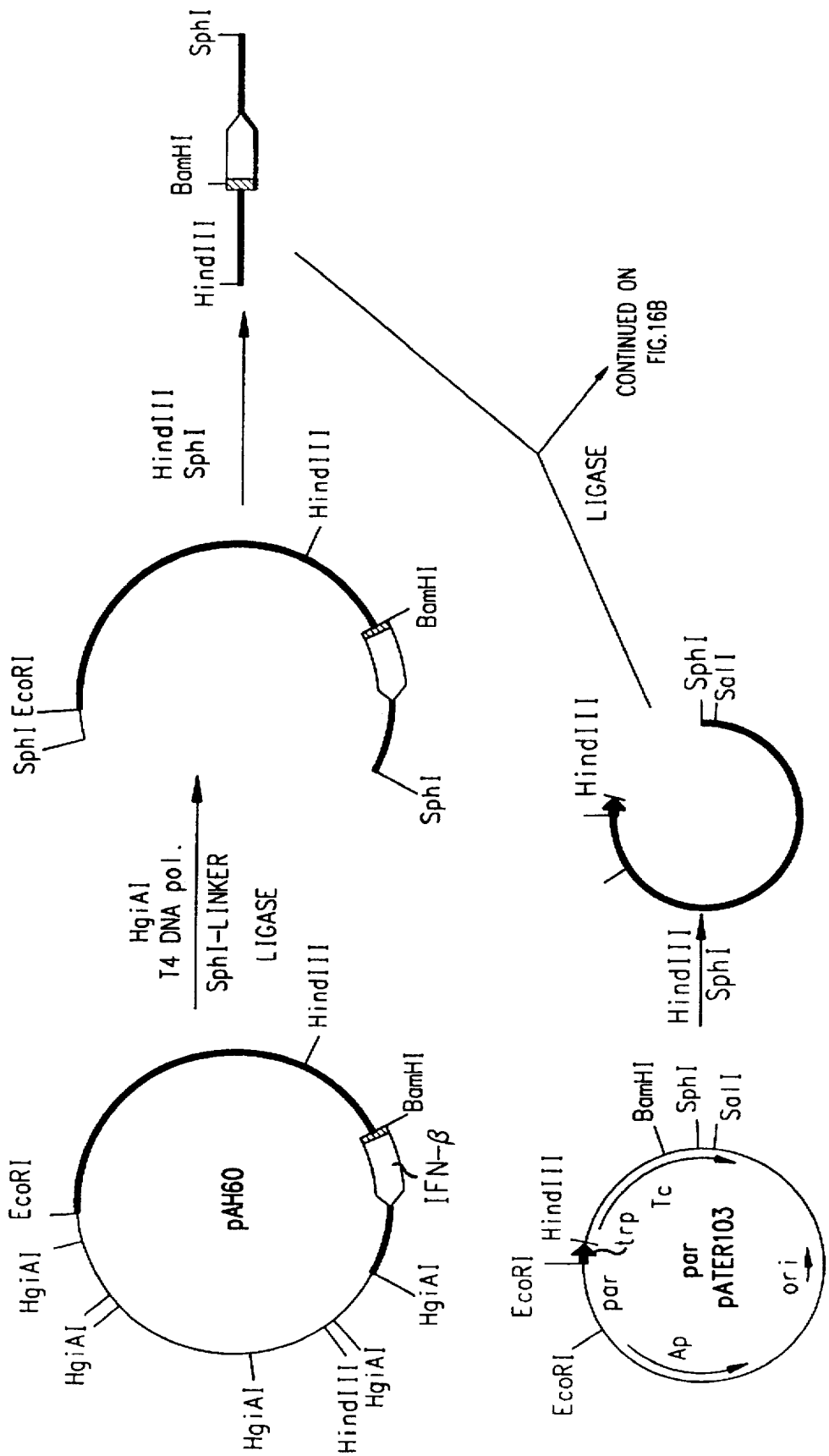
FIGS. 16A, 16B and 16C diagrammatically describe the preparation of an expression plasmid for EqIFN-β starting from pAH60.
Figure 16B:
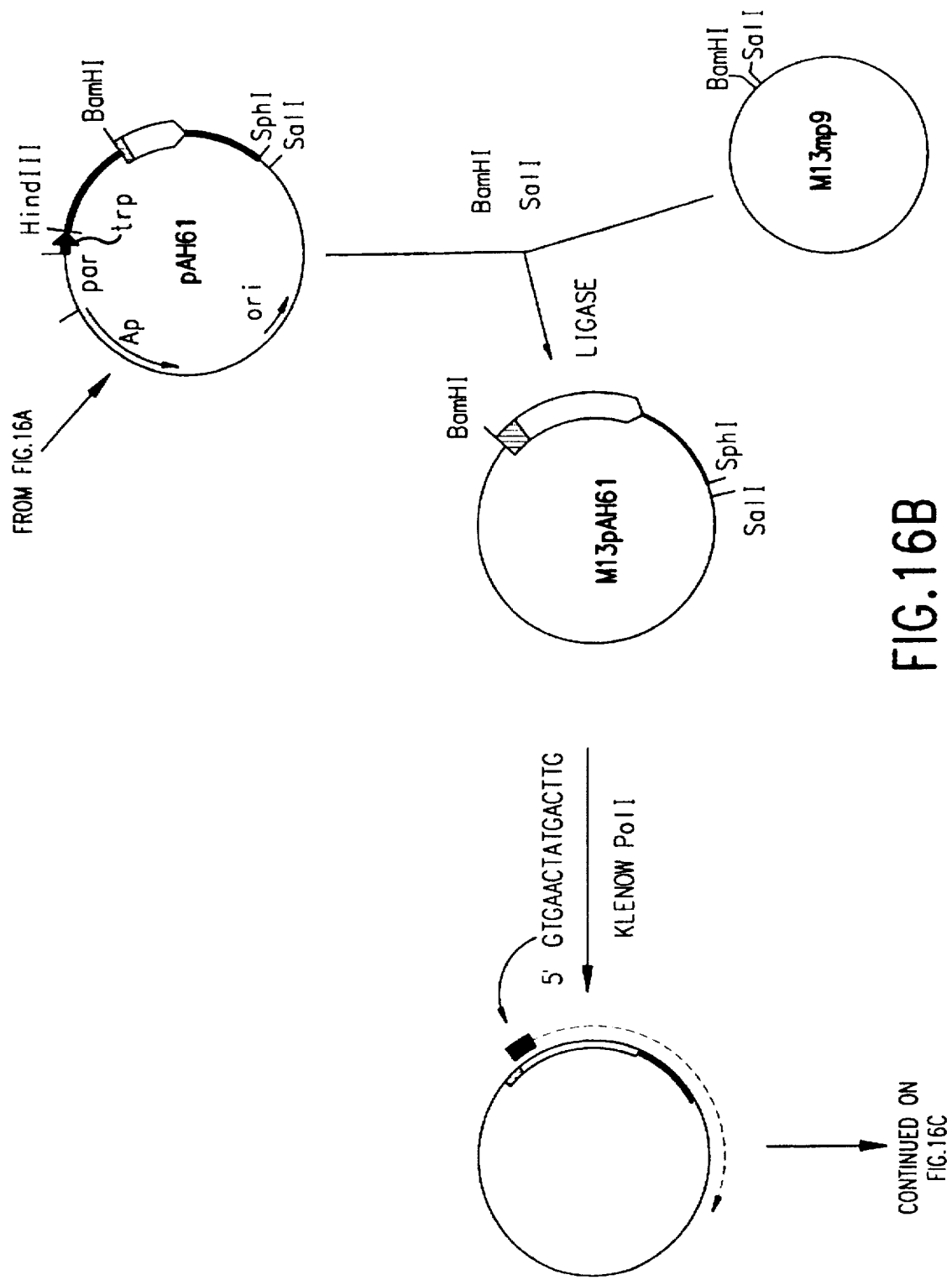
Figure 16C:
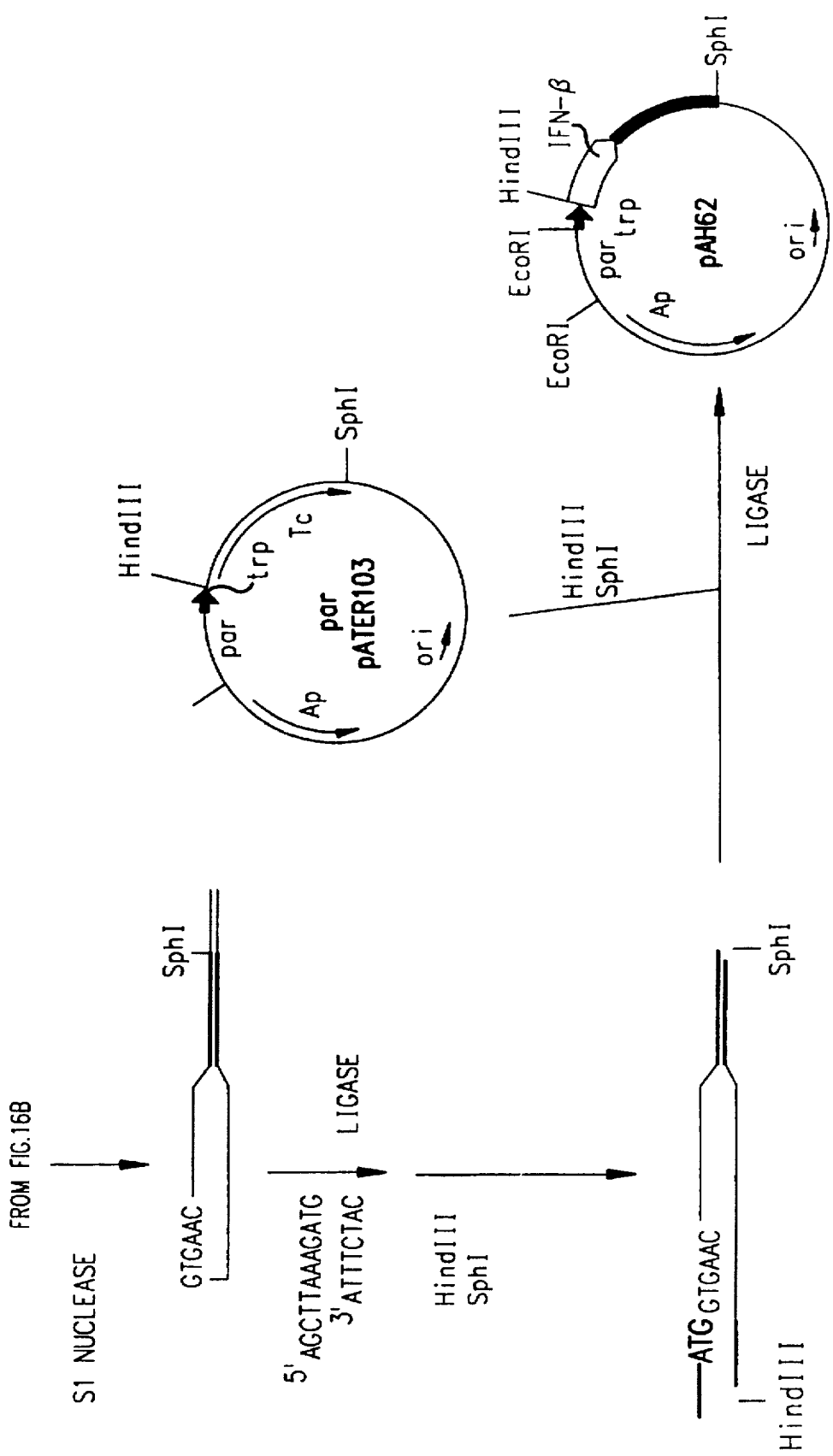

The procedure is schematically shown in FIGS. 16A–16C. 30 mcg of pAH60 plasmid were cut with 30 units of HgiAI in 150 mcl of volume. After deactivation of the enzyme at 70° C., the three prime overhanging DNA ends were straightened for thirty minutes at 37° C. With 7 units of T4 DNA polymerase (addition of 1 mM each of dATP, dGTP, dCTP and dTTP). SphI linkers were ligated to the blunt ends (see Example L) and the resulting DNA was cut with SphI and HindIII. A DNA fragment 1.85 kb long formed was isolated from an agarose gel and ligated with 50 ng of plasmid parpATER103 doubly cut with HindIII and SphI (Example K). A clone with the desired plasmid obtained after transformation of *E. coli* HB 101 was designated pAH61. This plasmid constitutes an intermediate stage for further construction of the expression plasmid. 20 mcg of plasmid pAH61 were cut twice with BamHI and SalI and a resulting DNA fragment 1.3 kb long was isolated from an agarose gel, purified and ligated with M13mp9 phage DNA doubly digested with BamHI/SalI. After transformation of *E. coli* JM101, single-strand phage DNA could be obtained from a recombinant M13-phage (M13pAH61). 3 pmol of this single strand DNA were mixed with 38 pmol of phosphorylated 15 mer oligonucleotide 5'GTGAACTAT-GACTTA in 50 mcl of 20 mM Tris HCl, pH 8.0, 10 mM of MgC12, then heated to 95° C. and slowly cooled to ambient temperature.

The oligonucleotide bonds precisely from the first base of the sequence of the mature β-interferon. The synthesis of the second strand on the basis of the single strand starting from the 15 mer primer was carried out in a volume of 100 mcl after the addition of 3 mM each of dATP, dGTP, dCTP and dTTP and 15 units of klenow fragment over a period of 1 hour at 22° C. After the addition of 20 mM of EDTA the DNA was extracted with phenol and chloroform and precipitated with ethanol.

Remaining single-strand DNA fragments were digested with 150 units of S1 nuclease (Sigma) in 400 mcl of reaction mixture for 2 hours at 14° C. (4 mM ZnAC2, 30 mM NaAC, 250 mM NaCl, 5% glycerine, pH 4.6). The reaction was stopped by the addition of EDTA and extraction with phenol and chloroform and the DNA was precipitated with ethanol. The mixture of the 12 mer and 8mer oligonucleotides 5'-AGCTTAAAGATG and 5'-CATCTTTA was ligated onto the DNA made blunt-ended by this treatment, as in Example H, and the resulting DNA was cut with HindIII and SphI. A DNA fragment with the desired length of 1.1 kb was isolated from an agarose gel and ligated with plasmid parpATER103 doubly cut with HindIII/SphI. After transformation of *E. coli* HB101, 54 colonies were obtained. Of 9 plasmid DNAs isolated therefrom, an EcoRI/SalI fragment 1.3 kb long was isolated and sequenced by the Sanger method. A plasmid obtained therefrom with the required sequence was designated pAH62. This plasmid permits the efficient expression of mature EqIFN-β protein in *E. coli*. A plasmid which carries a deletion of the first base (G) of the mature β-IFN gene was designated pAH62deltaG1. This plasmid permits the expression of a β-IFN shortened at the amino terminus by start of translation at the next ATG (corresponds to amino acid 19 in mature β-IFN), which surprisingly has an antiviral activity, although considerably less than that of the unshortened protein (see Example O).

O) Expression of interferon activity by *E. coli* HB101 containing the plasmid pAH52, pAH52/2, pAH53, pAH55 or pAH62

100 ml of bacterial culture are incubated at 37° C. With vigorous shaking until the optical density specified below is achieved at 600 nm in the following tryptophan-free medium (quantities are per litre of medium): 10 g (NH$_4$)$_2$PO$_4$, 3.5 g KH$_2$PO$_4$ pH 7.3 with NaOH, 0.5 g NaCl, 21 g casamino acids (acidically hydrolysed), 11 g glucose, 1 mM MgSO$_4$, 0.1 mM CaCl$_2$, 1 mg thiamine-HCl, 20 mg L-cysteine, 20 mg of 3-β-indolacrylic acid (IAA, inductor for the tryptophan operon), optionally 50–100 mg of ampicillin. The bacteria are then pelleted by centrifuging for 5 minutes at 4000 rpm, suspended with ¹/₁₀ of the culture volume of ice cold 50 mM Tris-HCl, pH 8.0, 30 mM NaCl and broken up twice for 30 seconds using an ultrasound probe (20 kHz, 100 watt) whilst cooling with ice. The cell debris is removed over a period of 10 minutes at 10,000 rpm (4° C.) and the residue is tested after being filtered sterile for interferon activity in an assay which measures the cytopathic effect (CPE) of vesicular stomatitis virus (VSV) or encephalomyocarditis virus (EMCV).

Test system:
NBL-6 cells (ATCC CCL 57, epidermis cells from horses skin)/
VSV A549 (ATCC CCL 185, human lung cancer cell line)/EMCV

| HB 101 with plasmid | $OD_{600\ nm}$ | IFN activity (units/1 culture) | |
|---|---|---|---|
| | | NBL-6/VSV E/1 | A549/EMV IE/1 |
| pAH52 | 4.2 | $1.8 \times 10^6$ | $5.2 \times 10^4$ |
| pAH52/2 | 6.0 | $2.0 \times 10^6$ | $7.6 \times 10^4$ |
| pAH53 | 5.7 | $1.8 \times 10^6$ | $6.2 \times 10^4$ |
| pAH55 | 5.7 | $1.2 \times 10^6$ | $9.0 \times 10^4$ |
| pAH62 | 3.0 | $1.1 \times 10^9$ | $<10^3$ |
| pAH62deltaG1 | 2.1 | $4.5 \times 10^5$ | $<10^3$ |
| HS12(HuIFN-α2C Standard) | | $5.2 \times 10^2$ | $2.6 \times 10^4$ |

The titre on A 549 cells was standardised to International units using human interferon standard.

P) Detecting the expressed horse interferons by labelling the proteins in maxi cells Plasmid-coded proteins can be selectively labelled in vivo using the maxi cell technique (37). *E. coli* CSR603 was transformed with the expression plasmids by conventional methods and transformed bacteria selected on agar plates containing ampicillin. The preparation of the maxi cells and the labelling of the proteins were carried out as prescribed by A. Sancar (37). The cells were grown in 15 ml of medium (see Example O) without indolacrylic acid at 37° C. until an $OD_{600\ nm}=0.5$ is reached and 10 ml of this culture are irradiated in a Petri dish for 5 seconds from a distance of 50 cm using a UV germicide lamp (15 watts) and incubation was continued for 1 hour at 37° C. The cultures were mixed with 100 mcg/ml of D-cycloserine and incubated for 14 hours at 37° C. and the bacteria were then harvested by centrifuging. The cells were washed twice with 5 ml of Hershey salt solution, suspended in 5 ml of Hershey medium with 20 mcg/ml of indolacrylic acid and incubated for 2 hours at 37° C. 5 micro Ci/ml of $^{35}$S-methionine (1000 Ci/mMol) were added to each culture and it was then shaken for 1 hour at 37° C. The cells were harvested in electrophoresis probe buffer containing SDS and 2-mercaptoethanol, lysed and the proteins were separated on a 15% polyacrylamide gel.

| Hershey salt solution (per liter): | Hershey medium (per 100 ml of Hershey salt solution): | |
|---|---|---|
| 5.4 g NaCl | 2 ml | 20% Glucose |
| 3.0 g KCl 1.1 g | 0.5 ml | 2% Threonine |
| 1.1 g $NH_4Cl$ | 1.0 ml | 1% Leucine |
| 15 mg $CaCl_2.2H_2O$ | 1.0 ml | 2% Proline |
| 0.2 mg $MgCl_2.6H_2O$ | 1.0 ml | 2% Arginine |
| 0.2 mg $FeCl_3.6H_2O$ | 0.1 ml | 0.1% Thiamine |
| 87 mh $KH_2PO_4$ | | |
| 12.1 g Tris + HCl pH 7.4 | | |

FIG. 17 shows the autoradiogram of the dried gel after 2 days' exposure on DuPont Cronex X-ray Film using a Kodak Lanex-Regular Intensifier Film at −80° C. A $^{14}$C-methylated protein mixture (Amersham) was used as the molecular weight standard. The controls used were the plasmid pER103 which contains only the promoter without an interferon gene and the plasmid pER21/1 which contains two copies of the human IFN-α2arg gene. The protein bands at about 18 kd are the interferons expressed by the plasmids.

Q) Detection of sequences hybridising with EqIFN-α, EqIFN-β and EqIFN-omega in genomic horse DNA The following procedure was used to detect the total number of sequences in the horse genome which have high homology with interferon genes of classes IFN-α, IFN-β and IFN-omega. 30 mcg of high molecular horse DNA (Example A) were totally digested with 100 units of the corresponding restriction enzyme in 300 mcl of reaction volume and 10 mcg of this cut DNA per trace were resolved according to size on a 0.8% agarose gel.

After Southern transfer onto nitrocellulose filters, denaturing and fixing of the DNA, each filter was hybridised with about $6 \times 10^6$ cpm of nick-translated probe (17 hours at 65° C., 5×SSPE, 5×Denhardt solution, 0.1% SDS, 20 mcg/ml of denatured salmon sperm DNA). The probe used for EqIFN-α was a HindIII/SphI fragment 1.0 kb long from plasmid pAH52, the probe for EqIFN-β used was a HindIII/SphI fragment 1.1 kb long from plasmid pAH62, containing the coding sequence for the entire mature interferon. The probe used for EqIFN-omega was the 2.1 kb EcoRI insert from plasmid pRH61. The filters were then washed under stringent conditions so that no cross-hybridisation could occur between the 3 interferon sequences: 4 times for 45 minutes at 65° C. With 0.3×SSC (45 mM NaCl, 4.5 mM $Na_3$ citrate), 0.1% SDS. Autoradiography was effected on DuPont Cronex X-ray Film using Kodak Lanex Regular Intensifier Film over a period of 7 days at −80° C.

Legend for FIG. 18: Column headings: M=size marker (lambda×EcoRI/HindIII) E=EcoRI, H=HindIII, Ba=BamHI, P=PstI, B=BglII 1) Isolation of dog DNA Frozen tissue, e.g. dog liver, was ground to a fine powder in liquid nitrogen and incubated for 3 hours at 55° C. in 0.5M EDTA, 10 mM Tris-HCl, pH 8.0, 0.5% SDS, 0.1 mg/ml of protease K (20 ml/g of tissue). The viscous solution obtained was freed from protein by phenol extraction and extracting 3 times with phenol/chloroform/isoamyl alcohol (25/24/1 vol), dialysed with 50 mM Tris-HCl pH 8.0, 10 mM EDTA, 10 mM NaCl, and the DNA was precipitated with 2 volumes of ethanol. After the DNA had been totally dried in vacuo it was put into solution at 4° C. in TE buffer (10 mM Tris-HCl pH 8.0, 1 mM EDTA) and centrifuged for 62 hours at 40.000 rpm at 20° C. With 1.273 g of CsCl/ml solution (Sorvall 50Ti rotor). The CsCl gradient was dripped out, the fractions containing DNA were dialysed with TE buffer and the DNA was then precipitated with 2 volumes of ethanol, washed with 70% ethanol, dried and redissolved in TE buffer (4° C.).

The finished DNA preparation was free from RNA and longer than 50 kb (determined by electro-phoresis on a 0.45% agarose gel).

2) Partial endonuclease digestion and size fractionation of dog DNA

Twice 50 mcg of dog DNA were incubated with 2.0 units of Sau3A in 450 mcl of reaction medium (10 mM Tris-HCl pH 7.5, 10 mM MgCl2, 1 mM dithiothreitol) at 37° C. After 40 and 60 minutes, 225 mcl aliquots were taken and mixed with 15 mM EDTA and the reaction was stopped by heating to 70° C. for 10 minutes. After the addition of 0.3M Na acetate, pH 6.0, the DNA was precipitated with 2.5 volumes of ethanol. After re-dissolving in TE buffer, the DNA was separated according to size by electrophoresis on a 0.45% agarose gel in TBE buffer (10.8 g/l Tris, 5.5 g/l boric acid, 0.93 g/l ($Na_2EDTA$) at about 1 V/cm overnight. Using size markers (lambda DNA doubly digested with EcoRI and HindIII and digested with HindIII) the gel fragment with DNA 10–23kb long was cut out, the DNA was electrically eluted from the gel in an analysis tube for 3 hours at 300 V (buffer 0.1×TBE), purified on an elutip-D column (Schleicher and Schüll) according to the instructions for use and then precipitated with ethanol.

In order to prevent the self-ligation of dog DNA fragments which may result on the one hand in artificial hybrids of dog DNA sequences and on the other hand in excessively large DNA fragments which can therefore no longer be packaged into lambda phages, the size-fractionated dog DNA fragments were dephosphorylated.

To do this, the DNA was incubated for 30 minutes at 37° C. in 140 mcl of reaction medium (50 mM Tris-Hcl, pH 9.5, 1.0 mM of $MgCL_2$ 0.1 mM of Zn acetate, 1 mM of spermidine) with 5 units of bovine intestinal phosphatase, a further 5 units of enzyme were added and the whole was incubated for 30 minutes. After the addition of EDTA to give a final concentration of 25 mM, the DNA was extracted once with phenol/chloroform/isoamyl alcohol (25/24/1 vol), twice with chloroform/isoamyl alcohol (24/1 vol) and 3 times with diethylether, then precipitated with ethanol, dried and dissolved in 0.1×TE buffer.

3) Construction of the dog genome-DNA library

The dephosphorylated dog DNA fragments 10–23 kb long were cloned in a lambda vector, for example lambda-EMBL3 or 3A (3) with G-A-T-C cohesive ends obtained by removing the internal BamHI fragment of the phage DNA.

The vector was grown in an *E. coli* strain with the suppressor factor sup F for example *E. coli* NM526, 538 or 539 (3), in LB broth (20) with 5 mM of $MgSO_4$, precipitated with polyethyleneglycol and purified by CsCl-densitity gradient centrifuging twice (0.71 g of CsCl/ml of solution, 40 hours at 45,000 rpm, 20° C.). After dialysis with TE buffer, the phage DNA was freed from protein by extracting twice with phenol/chloroform/isoamyl alcohol (25/24/1 Vol) and extracting twice with chloroform/isoamyl alcohol (24/1 vol) and concentrated by ethanol precipitation.

In order to obtain the end fragments of EMBL3A, 50 mcg of phage DNA were totally digested with BamHI for two hours at 37° C. in 450 mcl of reaction medium (10 mM Tris-Hcl, pH 7.5, 10 mM $MgCl_2$, 1 mM dithiothreitol) then digested with 15 mM EDTA for 10 minutes, then at 70° C. the reaction was stopped and the DNA was precipitated with ethanol.

In order to avoid re-ligation, the middle fragment was cut again with with EcoRI and the oligonucleotide falling away was eliminated by isopropanol precipitation.

The BamHI-digested lambda-DNA was totally digested for 2 hours with EcoRI at 37° C. in 450 mcl of 10 mM Tris-Hcl, pH 7.5, 100 mM NaCl, 10 mM $MgCl_2$ and the reaction was stopped by adding 15 mM EDTA and heating to 70° C. for 10 minutes. After the addition of Na-acetate to give a final concentration of 0.3M, the three large DNA fragments were precipitated with 0.6 volumes of isopropanol for 15 minutes at 0° C., washed twice, with 0.45M Na-acetate/0.6 volumes of isopropanol and once with 0.3M Na-acetate/2.5 volumes of ethanol and dissolved in 15 mcl of 0.1×TE buffer. The BamHI/EcoRI linkers remain in solution during this procedure.

The EMBL3A fragments (8 mcg) were combined with about 5 mcg of 10–23 kb dog DNA and 10 units of T4-DNA ligase (NEN) and incubated overnight at 14° C. and for 1 day at 4° C. in 50 mcl of ligation medium (66 mM Tris-Hcl, pH 7.2, 0.1M NaCl, 10 mM $MgCl_2$, 1 mM EDTA, 5 mM dithiothreitol, 0.5 mM ATP). The ligated DNA mixture was packed into mature lambda-phage particles using an in vitro lambda packing system (27).

The components of this system, i.e. ultrasound extract (SE), freeze-thaw lysate (FTL), buffer M1 and A were prepared according to reference (27). 10 mcl of aliquots of the ligated DNA mixture were incubated for 2 minutes at ambient temperature with 25 mcl of SE which, like the FTL, had thawed for 30 minutes from ice, then 100 mcl of FTL were added and the mixtured was reincubated for 60 minutes at ambient temperature. The packaging mixture was diluted with 150 mcl of lambda dieluant (100 mM of Tris-HCl, pH 7.5, 10 mM $MgSO_4$, 1 mM EDTA) and stored at 4° C.

A small amount of the packaged lambda phages was tritrated on the *E. coli* strain NM 528 SupF. In all, the process yielded about $1 \times 10^6$ independent dog DNA recombinants. The remainder of the packaged material was multiplied by plating on NM 528 in a density of 30,000 plague-forming units (pfu) per 13.5 cm of $LB/MgSO_4$ agar plate.

4) Screening of the dog gene library for interferon genes

In order to identify the recombinant phages which contain dog interferon genes, the nucleotide homology demonstrated by Southern-Blots (17) with radioactively labelled human IFN-alpha genes was used.

10 mcg of high molecular horse DNA was totally digested with EcoRI or HindIII, resolved by electrophoresis on 0.8% agarose gel and transferred to nitrocellulose filters. A P-32-labelled DNA fragment was prepared by conventional methods (25) from an 845 bp HindIII fragment originating from the expression plasmid pER33 (14) and containing the entire protein-coding region for mature human interferon-alpha 2ARG.

Figure 21:
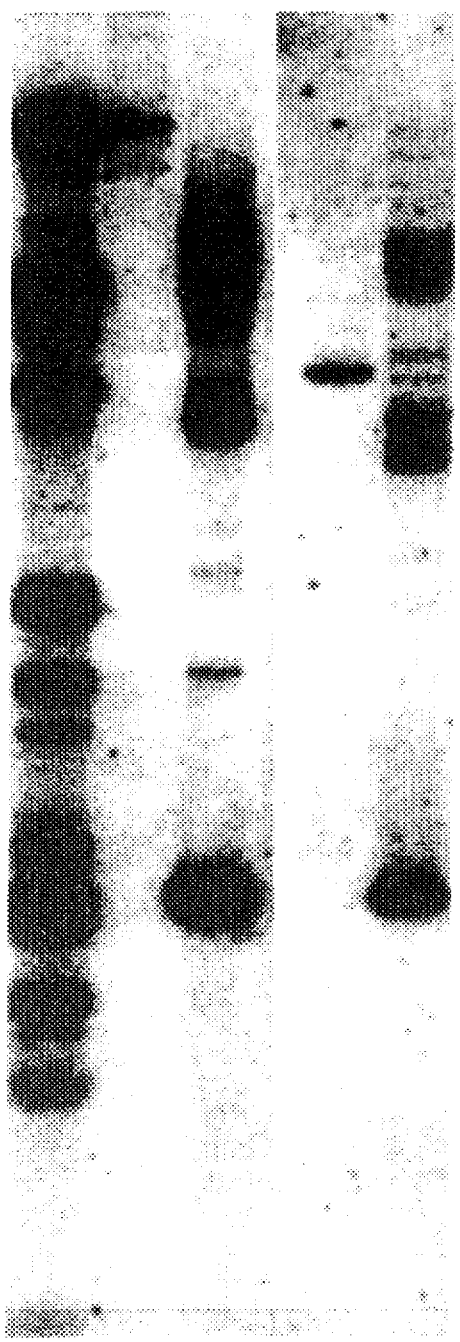
FIG. 21 is an autoradiogram showing the family of interferon genes in dogs, using as a probe the region encoding the mature human interferon-α2 protein.

The nitrocellulose filters were prehybridized for 7 hours at 65° C. in 5×SSPE (0.9M NaCl, 50 nM $NaH_2PO_4$, 5 mM EDTA, pH 7.4), 5×Denhart solution (0.1% ficoll, 0.1% polyvinylpyrrolidone, 0.1% bovine serum albumin), 0.1% SDS, 20 mg/ml of salmon sperm DNA and then hybridized with $13 \times 10^6$ cpm of the labelled probe in the same solution but without the salmon sperm DNA. After incubation over night at 65° C., the filters were washed 4 times for 1 to 1.5 hours in 3×SSC (0.45M NaCl, 45 mM Nacitrate), 0.1% SDS at 65° C. and exposed for 7 days on Kodak X-omat S-X-ray film with Kodak regular intensifier films (FIG. 21). The appearance of several bands indicates a family of alpha-interferon genes in dogs, as had earlier been detected in cattle, pigs and humans.

Therefore, the same hybridizing conditions were used for screening the interferon genes in the dog DNA library.

1,000,000 recombinant lambda phages were plated on *E. coli* NM528 in a density of 30,000 pfu/13.5 cm of plate. Two-fold nitrocellulose replicas were prepared from each plate using the method described by Benton and Davis (19).

After 2 hours' baking at 80° C. the filters were washed for 1.5 hours at 65° C. in 1M NaCl, 10 mM Tris-HCl, pH 8.0, 0.1% SDS, prehybridized overnight as described above and 2 filter replicas from each plate were hybridized for 24 hours with $1.5 \times 10^6$ cpm of radioactive alpha-interferon probe or $1 \times 10^6$ cpm beta-interferon probe per filter. After screening had been repeated 3 times, 9 dog alpha-interferon clones and were obtained which gave positive hybridization signals.

5) Characterisation of the recombinant phages

Phage DNA was prepared from 9 recombinants hybridising with human alpha IFN. The DNA's were digested with EcoRI, BamHI, HindIII, PstI, BglII, SalI and SmaI and separated electrophoretically in a 0.8% agarose gel. The size of the hybridizing fragments was determind by the Southern method. The position of the restriction sites within the lambda insert was determined using a method described by Rackwitz et al. (4) after partial restriction digestion of the lambda DNA, labelling of the right or left sticky ends of the lambda arms with synthetic P-32-labelled oligonucleotides and electrophoresis in 0.45% agarose gels. The resulting restriction map of the clone Ca-alpha-11-2 is shown in FIG. 22.

6) Subcloning of the dog interferon alpha genes

Two restriction fragments of the clone Ca-alpha11-2 which had hybridised with the human alpha interferon marker were subcloned into the multiple restriction enzyme cloning site of the pBR322 derivative pUC9. Insertion of a foreign DNA fragment leads to an interruption in the lac Z gene of beta-galactosidase and thus alters the phenotype of the *E. coli* strain JM101, transformed with the plasmid, from lac+to lac−. Owing to the non-functioning beta-galactosidase, JM101 induced with isopropyl thiogalactoside (IPTG) cannot cleave the colourless substrate analoge 5-bromo-4-chloro-3-indolyl-β-D-galactoside (BCIG) to give the blue dye. Bacteria colonies with lac− phenotype can therefore be recognised by their white colour.

A 3.7 kb HindII fragment of the clone Eq-alpha1 was eluted from an agarose gel, purified on an elutip-D column and ligated in an approximately 10-fold molar excess with 40 mg of pUC9 vector cut with SmaI and dephosphorylated, then transformed in *E. coli* JM101 and poured out with LB top agar with 0.2 mg/ml of BCIG, 0.17 mg/ml of IPTG and 01 mg/ml of ampicillin. White colonies were grown in 5 ml of LB broth with 0.1 mg/ml of ampicillin over night at 37° C. and screened for the inserted fragment by a plasmid minipreparation method (25). A plasmid thus obtained was designated pAH2. Similarly a 2.4 kb SmaI fragment from the same lambda clone was subcloned in pUC9. The resulting plasmid was designated pAH4.

7) DNA sequence of dog alpha interferon genes from clone Ca-alpha11-2

The 1.7 kb HindIII insert of pAH50 (3.2 kb HindIII fragment subclone of Ca-alpha1-2 FIG. 23) was sequenced by the dideoxy method described by Sanger (23) using the shotgun process. 60 mcg of pAH2 plasmid DNA were totally digested with SmaI the 3.7 kb fragment was isolated from a 1% agarose gel and purified as described above.

15 mcl of this fragment were ligated with itself in 100 mcl of ligation medium with 14 units of $T_4$-DNA ligase overnight at 14° C. and for a further 4 days at 4° C. This ligated DNA was divided into small pieces in an ice bath with ultrasound in 20 second pulses, a total of 100–140 seconds. The DNA ends were repaired with 15 units of the large fragment of *E. coli* polymerase I (klenow fragment) for 2 hours at 14° C. in 250 mcl of reaction medium (50 mM Tric-Hcl, pH 7.5, 10 mM $MgCl_2$, 1 mM dithiothreitol, 0.5 mg/ml of bovine serum albumin per 0.1 mM dATP, dGTP, dCTP, dTTP). After concentration by ethanol precipitation, the DNA pretreated in this way was separated on a 1% agarose gel and DNA fragments in the size range from 0.35 to 1.0 kb were isolated and purified. The fragments were ligated in an approximately 10-fold molar excess with the replicative form of bacteriophage M13mp8 (22) cut with SmaI and dephosphorylated, and were then transformed with *E. coli* JM101. The single strand DNA of the recombinant phages thus obtained was isolated and after the bonding of a synthetic oligonucleotide, synthesis of the second strand was carried out in four individual reactions with the klenow fragment of *E. coli* DNA-polymerase I.

The sequences of the inserts of the various recombinant phages were combined with the aid of a computer programme of Staden (24) modified by C. Pieler to form a total sequence which is shown in FIGS. 24A–24C.

Figure 25C:

In just the same way, a 1.9 kb HindIII fragment from the plasmid pAH4 (2.4 kb SmaI subclone from Ca-alpha11-2, FIG. 23) was sequenced (FIGS. 25A–25C).

8) Construction of expression plasmid pRH 100

All enzyme reactions were carried out under the conditions specified by the manufacturers.

7 mcg of plasmid pER 103 (Eva Dworkin-Rastl et al., Gene 21 (1983) 237–248, EP-A-0.115-613) were linearised in 50 mcl of reaction medium with the restriction endonuclease HindIII. After incubation for I hour at 37° C., 50 mcl of 2×CIP buffer were added (2×CIP buffer=20 mM Tris, pH=9.2, 0.2 mM EDTA). After the addition of 2 units of alkaline phosphatase from calves intestine (CIP) the 5' terminal phosphate residues were removed; incubation was carried out for 30 minutes at 45° C. The reaction was stopped by the addition of 4 mcl 0.5 EDTA solution and the addition of 10 mcl of 1M Tris, pH=8.0 solution. The proteins were removed by extracting twice with phenol and once with phenol/chloroform. The DNA was precipitated from the aqueous phase after the addition of 0.1 vol 3M sodium acetate solution pH=5.5 and 250 mcl ethanol and the DNA precipitate after being centrifuged was washed once with 70% ethanol solution. The DNA was dried and the pellet was then dissolved in 20 mcl of TE buffer (10 mM Tris pH=8.0, 1 mM EDTA).

1 mcg batches of the synthetically produced oligodeoxynucleotides d (AGCTTAAAGATGAGCT) and d(CATCTTTA) were phosphorylated in 10 mcl of reaction solution with the addition of 10 units of T4-PNK (polynucleotide kinase) and 1 mM rATP. The reaction took place at 37° C. and lasted 45 minutes. The reaction was stopped by heating to 70° C. for 10 minutes.

5 mcl of the plasmid solution and the phosphorylated oligonucleotide were mixed together and heated to 70° C. for 5 minutes. Then the solution was cooled to 0° C. and 2 mcl of 10×ligase buffer (500 mM Tris, pH=7.5), 100 mM $MgCl_2$ 200 mM DDT (dithiothreitol), 1 mM rATP, 500 mcG/ml BAS (bovine serum albumin), and 2 mcl of water and 10 units of T4-DNA ligase were added. The reaction lasted 40 hours and was carried out at 4° C. It was stopped by heating to 70° C. for 10 minutes. 2 mcl of this ligase reaction were digested in a total of 30 mcl of solution with 10 units of the restriction endonuclease SacI (New England Biolabs) for 3 hours at 37° C. The reaction was stopped by heating to 70° C. for 10 minutes. 5 mcl of this reaction mixture were ligated in a total of 30 mcl by adding 10 units of T4-PNK at 14° C. for 16 hours.

200 mcl of competent *E. coli* Hb101 were mixed with 10 mcl of this ligase reaction. The bacteria were kept on ice for 45 minutes and then heated to 42° C. for 2 minutes in order to allow DNA uptake. Then the bacterial suspension was re-incubated at 0° C. for 10 minutes. Finally the transformed bacteria were spread out on an LB agar containing 50 mcg/ml of ampicillin.

From the bacterial colonies produced, 12 were chosen at random and the plasmids from them were isolated on a microscopic scale (Birnboim and Doly. Nucl. Acids Res. 7 (1979) 1513–1523). The resulting DNA was cut with the restriction endonuclease SacI and the DNA was separated on an agarose gel (1%, 1×TBE buffer). The migration of the DNA as a linear molecule measuring about 4,400 bp confirmed that a SacI recognition site had been inserted into the plasmid. One of these plasmids was randomly selected. *E. coli* HB101 was again transformed with the DNA from the associated mini preparation. From the resulting transformed bacteria, a colony was selected and grown on a larger scale. The plasmid isolated therefrom was cut with the restriction endonucleases EcoRI and BamHI, the DNA was separated on a 1% agarose gel and the smaller fragment was isolated from the gel by electroelution. This EcoRI-BamHI DNA fragment, about 460 bp long, was sequenced according to Sanger (F. Sanger et al., Proc. Natl. Acad. Sci. (1977) 5463–5467). The plasmid analysed in this way was designated pRH 100.

9) Direct expression of mature CaIFN-alpha1 in *E. coli*

The procedure for the construction of the expression plasmid pAH4/2 for mature CaIFN-alpha1 is diagrammatically shown in FIG. 28.

5 mcg of plasmid pRH100 were totally cut with the restriction endonuclease BamHI and then the 5' terminal phosphate residues were removed with calves' intestinal phosphatase (CIP). 30 mcg of plasmid pAH4 (see Example 6) were digested with BamHI. After electrophoretic separation of the DNA in an agarose gel, DNA fragments 0.6 kb long containing the entire coding sequence for CaIFN-alpha1 were isolated from the gel and purified.

About 1 mcg of these 0.6 kb DNA fragments was ligated with 25 ng of cut pRH100 vector DNA in 10 mcl of ligation medium (66 mM Tris-HCl, pH 7.2, 0.1M NaCl, 10 mM $MgCl_2$, 1 mM EDTA, 5 mM dithiothreitol, 0.5 mM ATP) with 10 units of T4 DNA ligase at 14° C. for 24 hours. Competent *E. coli* HB101 was transformed with 5 mcl of this ligase reaction and spread on LB agar containing 50 mcg/ml of ampicillin.

From the resulting bacterial colonies, plasmids were isolated on a microscopic scale and characterised by restriction analysis with various enzymes. A plasmid containing the interferon gene and tryptophan promoter in the same orientation was designated pAH104 (FIG. 28). This plasmid constitutes an intermediate stage for the preparation of the final expression plasmid for mature CaIFN-alpha1.

Preparation of expression plasmid pAH4/2

About 7 pmol of the 0.6 kb long BamHI fragment of plasmid pAH4 were mixed with 1 nmol of synthetic oligodeoxynucleotide (d(TGCCACCTGCCCGAC) which was first provided with a phosphate group at the 5' end by means of T4 polynucleotide kinase, and made up to the total volume of 34 mcl with water. The 15 mer oligonucleotide contains the coding sequence for the N-terminal 5 mino acids of the mature dog alpha interferon. The DNA solution was heated to 100° C. for 5 minutes and then cooled, whilst the oligonucleotide, present in a large excess, bonds to the complementary site of the DNA single strand.

The second strand was synthesised starting from the bound oligonucleotide primer in 70 mcl of reaction medium (50 mM Tris-HCl pH 7.5, 10 mM $MgCl_2$, 1 mM dithiothreitol, 0.5 mg/ml bovine serum albumin, 1 mM each of dATP, dGTP, dCTP, dTTP) with 35 units of klenow fragment of *E. coli* DNA polymerase I for 90 minutes at 22° C. The reaction was stopped by the addition of 20 mM EDTA and the proteins were eliminated by phenol/chloroform extraction. The DNA was precipitated with ethanol after the addition of 0.1 vol 3M sodium acetate solution, pH 6, and washed with 70% ethanol.

The remaining single stranded DNA fragments were removed with S1 nuclease. This was done by dissolving the dried DNA pellet in 300 mcl of 91 reaction buffer (4 mM $Zn(Ac)_2$, 30 mM NaAc, 250 mM NaCl, 5% glycerine, pH 4.6) and incubating with 150 units of S1 nuclease (Sigma) for 2 hours at 14° C. The reaction was stopped by adding 20 mM EDTA. The proteins were removed by extraction with phenol and chloroform. After the addition of 0.15 vol of 3M sodium acetate solution and 0.6 vol isopropanol, the DNA was precipitated from the aqueous phase at 0° C. and washed with 70% ethanol.

The DNA obtained was digested with 60 units of PstI for 2.5 hours at 37° C. and then separated by electrophoresis in a 2% agarose gel. DNA fragments about 300 bp long were isolated and purified. 30 mcg of plasmid pAH104 were digested with 50 units of SacI for 2 hours at 37° C. and the enzyme was deactivated for 10 minutes at 70° C. After the addition of 0.5 mM of all four desoxynucleotides and 30 units of klenow polymerase, the mixture was incubated for 60 minutes at ambient temperature to make the DNA ends blunt. The proteins were removed by extraction with phenol and chloroform and the DNA was precipitated with ethanol. The DNA obtained was partially cut with 20 units of PstI for 40 minutes at 37° C. and the reaction was stopped by the addition of 20 mM EDTA. The DNA was electrophoretically separated in an agarose gel and fragments 4.3 kb long were isolated and purified.

The DNA obtained was ligated with the 0.3 kb long DNA fragment described above in 10 mcl of ligation medium with 10 units of T4-DNA ligase for 20 hours at 14° C. *E. coli* HB101 was transformed with this ligase reaction and plated on LB-agar containing ampicillin.

The bacterial colonies produced were transferred to fresh agar plates and in duplicate to nitrocellulose filters placed on agar plates. After incubation at 37° C. the bacteria were lysed in accordance with the method described by Grunstein and Hogness (M. Grunstein & D. Hogness, Proc. Natl. Acad. Sci. USA (1975) 72, 3961-) and after denaturing the DNA was bonded to the nitrocellulose. The cell debris was removed by incubation for 16 hours at 65° C. in a pre-wash solution (1M NaCl, 50 mM Tris-HCl 1 pH 8.0, 1 mM EDTA, 0.1% SDS). The filters were then hybridised in 10 ml of hybridising solution (0.9M NaCl, 90 mM Tris-HCl pH 7.5, 6 mm EDTA, 0.1% SDS, 0.1 mcg/ml tRNA from *E. coli* (Sigma) with $2 \times 10^7$ cpm with $^{32}$P-labelled oligodesoxynucleotide d(TGCCACCTGCCCGAC) for 3 hours at 47° C.

18 pmol of oligonucleotide were incubated with 18 pmol of [$^{32}$P]ATP (3000 Ci/mmol, Amersham) in 20 mcl of phosphorylating buffer (70 mM Tris-HCl, 7.6, 10 mM $MgCl_2$, 5 mM dithiothreitol) with 10 units of T4-polynucleotide kinase (BRL) for 45 minutes at 37° C. The reaction was stopped by the addition of 25 mM EDTA and the radioactivity not incorporated was removed by exclusion chromatography over a 1 ml Biogel P6-DG (Biorad) column.

The filters were washed 4 times for 30 minutes at 47° C. The wash solution was the same as the hybridising solution but with no added tRNA. The filters were exposed on Kodak X-omat S X-ray film using Kodak X-omat Regular Intensifying Films at −80° C. Plasmid DNA was isolated by a mini preparation process from bacterial colonies which yielded a positive hybridising signal in the autoradiogram. The plasmids were totally cut with HindIII and BamHI. After electrophoretic separation in an agarose gel, 0.5 kb long restriction fragments were isolated and DNA sequence analysis was carried out according to Sanger.

A plasmid having the desired structure was designated pAH4/2. It made it possible to express mature CaIFN-alpha1 in *E. coli*.

10) Preparation of the plasmid pAH4/3

The gene from the plasmid pAH4/2 (Example 9) manipulated for the bacterial expression of CaIFN-alpha1 was subcloned in a modified plasmid vector parpATER103 (Example K) having a higher copy number per cell and increased plasmid stability.

About 0.5 mcg of the HindIII/BamHI fragment of pAH4/2 0.5 kb long (Example 9) were incubated with 25 ng of plasmid vector parpATER103 which had been cut with HindIII and BamHI and gel-purified, in 10 mcl of ligation medium with 5 units of T4-DNA ligase for 3 hours at 22° C. Competent *E. coli* HB101 was transformed with 5 mcl of this ligase reaction and plated on LB agar with 50 mcg/ml of ampicillin.

From the bacterial colonies produced, 6 were chosen at random and the plasmids were isolated from them on a microscopic scale. A plasmid which had the required structure after restriction analysis with various restriction endonucleases was designated PAH4/3.

11) Expression of the interferon activity by *E. coli* HB101 containing the plasmid pAH4/2 or pAH4/3

100 ml of bacterial culture were incubated at 37° C. With vigorous shaking until the optical density specified below was reached at 600 nm in the following tryptophan-free medium (amounts given are per litre of medium):

10 g of $(NH_4)_2PO_4$, 3.5 g of $KH_2PO_4$, pH 7.3 with NaOH, 0.5 g NaCl, 21 g casamino acids (acidically hydrolysed), 1 g glucose, 1 mM $MgSO_4$, 0.1 mM $CaCl_2$, 1 mg thiamine-HCl, 20 mg L-cysteine, 20 mg 3-β-indolacrylic acid IAA, inductor for the tryptophan operon), optionally 50–100 mg of ampicillin.

Then the bacteria were pelleted by centrifuging for 5 minutes at 4000 rpm, suspended with ⅒th of the culture volume of ice cold 50 mM Tris-HCl, pH 8.0, 30 mM NaCl and broken up twice for 30 seconds by ultrasound (20 kHz, 100 watts) whilst cooling with ice. The cell debris was removed for 10 minutes at 10.000 rpm (4° C.) and after being filtered sterile the supernatent was checked for interferon activity in an assay which measures the reduction of the cytopathic effect (CPE) of vesicular virus (VSV).

| Test system: A-72 (ATCC CRL 1542) canine tumour/vesicular stomatitis virus | | |
|---|---|---|
| Plasmid | $OD_{600\ nm}$ | IFN units/1 bacterial culture |
| PAH4/2 | 4.2 | $3.2 \times 10^5$ |
| PAH4/3 | 3.2 | $3.0 \times 10^5$ |

12) Detection of sequences hybridising with CaIFN-alpha1 and EqIFn-omega in genomic dog DNA In order to detect the total number of sequences in the dog genome which have high homology with interferon genes of class IFN-alpha or IFN-omega, the following procedure was used:

20 mcg of high molecular dog DNA (Example 1) were totally digested with 60 units of the corresponding restriction enzyme in 200 mcl of reaction volume and 10 mcg of this cut DNA per trace were separated according to size on a 0.8% agarose gel. After Southern Transfer onto nitrocellulose filters, denaturing and fixing of the DNA, each filter was hybridised with about $6 \times 10^6$ cpm of nick translated DNA probe (17 hours at 65° C., 5×Denhardt solution, 0.1% SDS, 20 mcg/ml of denatured salmon sperm DNA, see Example 4).

The probe used for CaIFN-alpha was a 0.6 kb long BamHI fragment of plasmid pAH4 which contains the entire coding sequence for the interferon. The probe used for EqIFN-omega was the 2.1 kb EcoRI insert from plasmid pRH61.

The filter hybridised with CaIFN-alpha1 was subsequently washed under stringent conditions, 4 times 45 minutes at 65° C. With 0.3×SSC (45 mM NaCl, 4.5 mM $Na_3$ citrate), 0.1% SDS.

The filter hybridised with EqIFN-omega was washed at 65° C. With 2×SSC (0.3M NaCl, 30 mM $Na_3$ citrate), 0.1% SDS, 4 times 45 minutes at 65° C. With 0.3×SSC (45 mM NaCl, 4.5 mM $Na_3$ citrate), 0.1% SDS. The filter hybridised with EqIFN-omega was washed at 65° C. With 2×SSC (0.3M NaCl, 30 mM $Na_3$ citrate), 0.1% SDS. Autoradiography was effected on DuPont Cronex X-ray Film using Kodak Lanex-Regular Intensifying Film for 7 days at −80° C.

The autoradiogram (FIG. 29) shows that apart from the two chains coding for identical alpha-interferons no other sequences can be detected in the dog genome which have a similar high degree of homology with CaIFN-alpha1 such as occurs within an interferon class in other species. With DNA of an equine omega-interferon gene, under rather less stringent conditions, at least one gene can be detected which is different from the alpha-interferons of the dog described.

13) Subcloning and sequencing of a second equine interferon gene (EqIFN-omega2) of lambda-clone Eg-alpha16

Figure 30:
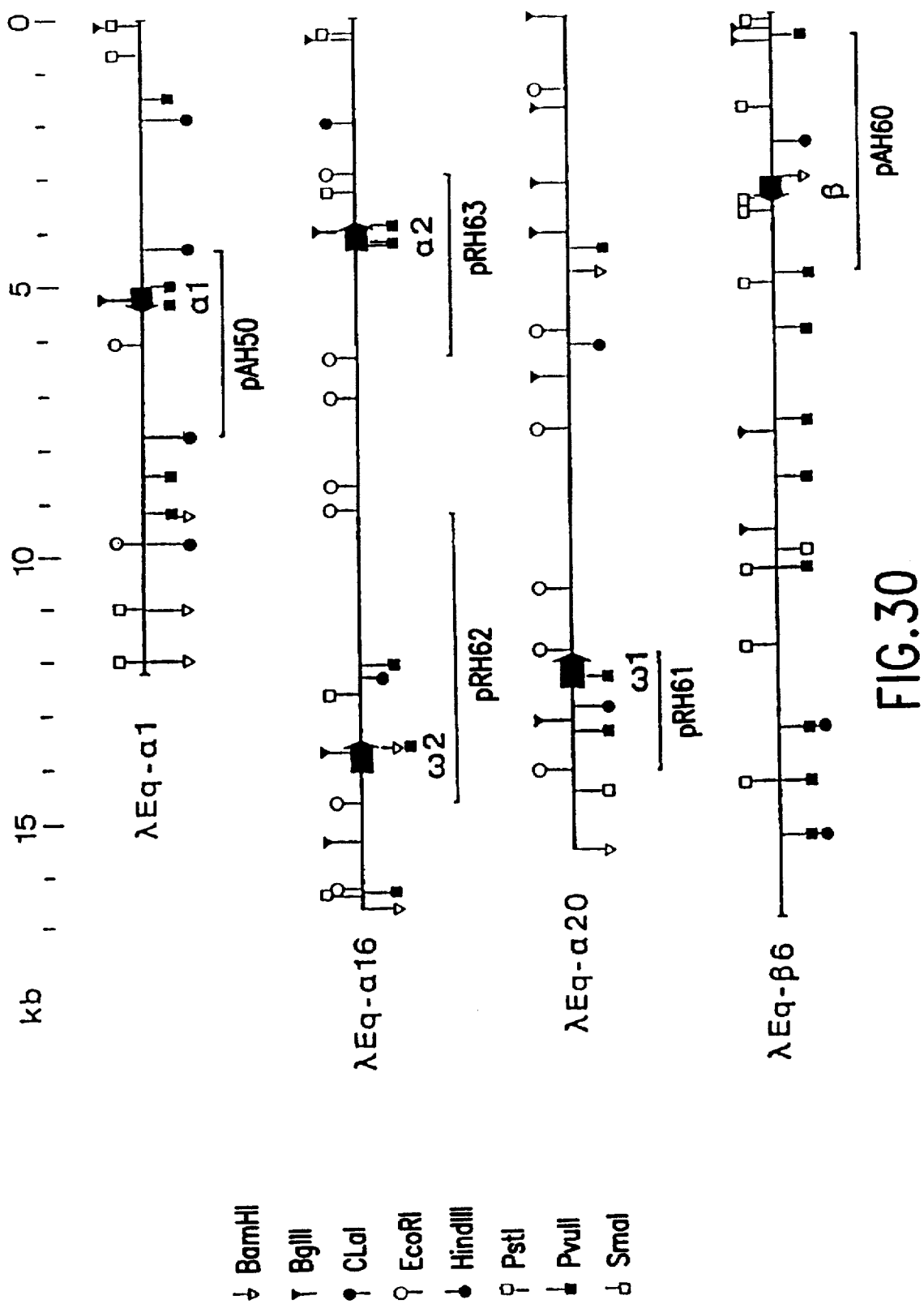
FIG. 30 is a restriction map of clones λEq-α1, λEq-λ16, λEq-α20 and λEq-β6.
Figure 32A:
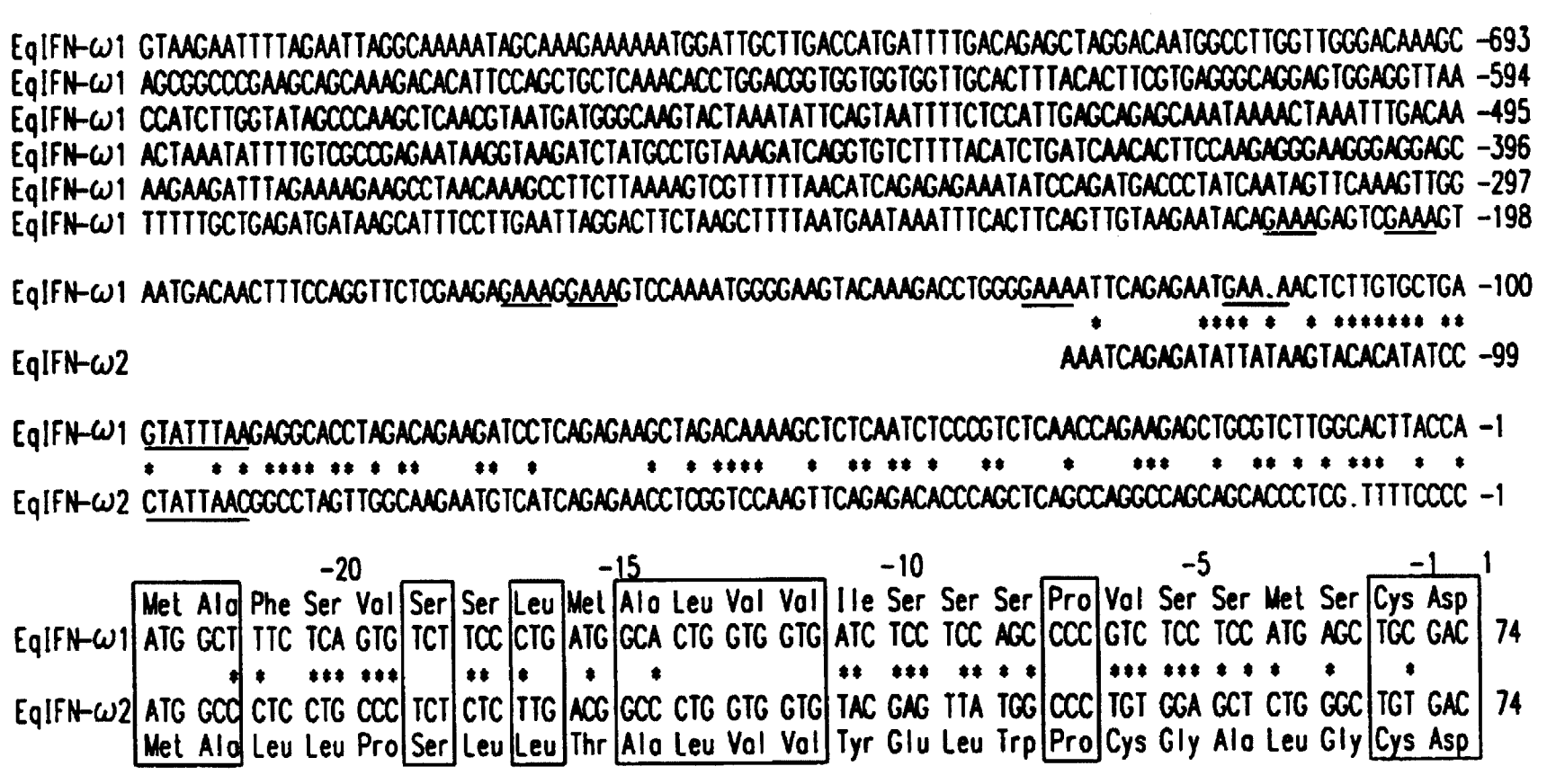
Figure 40:
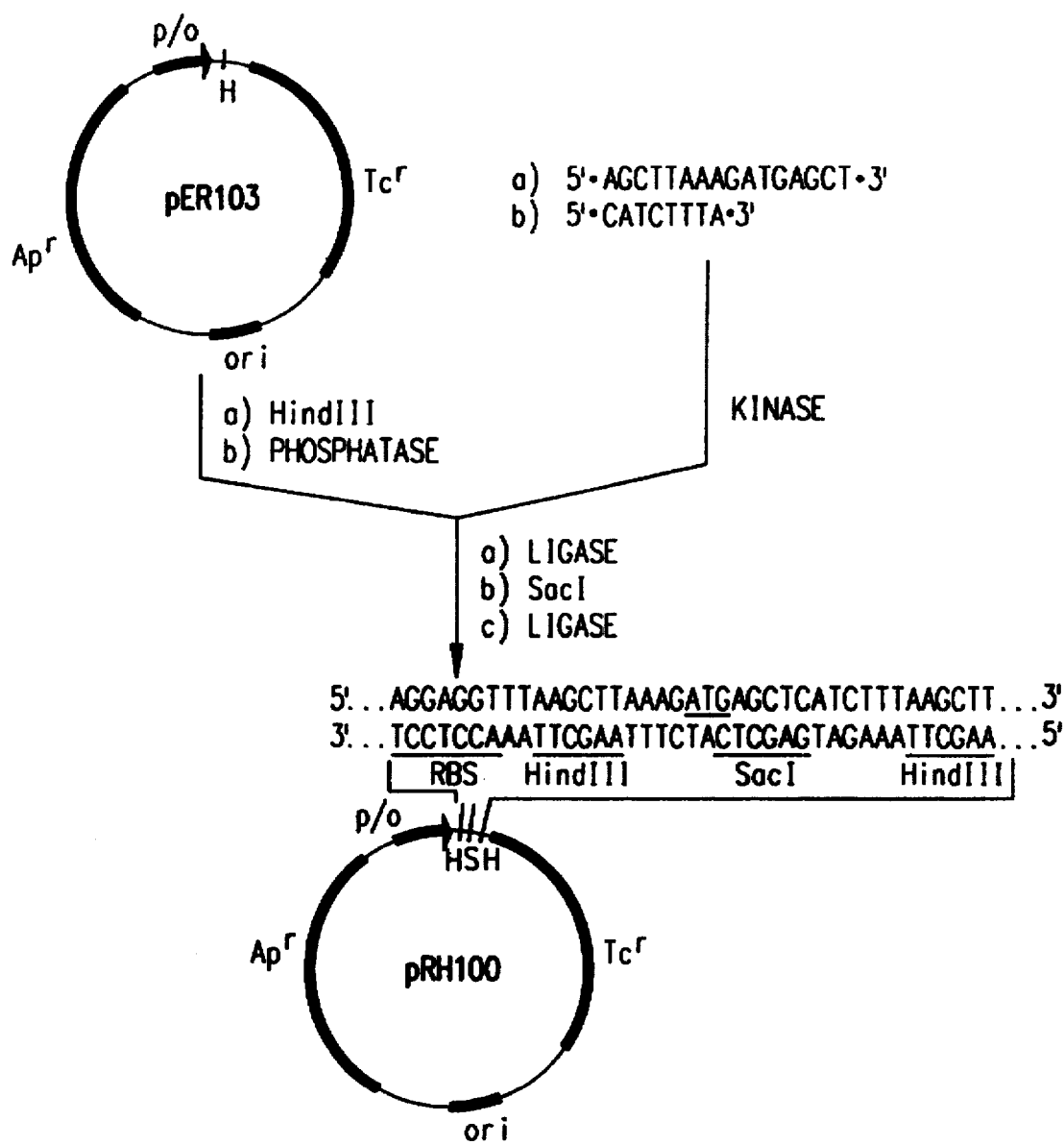
FIG. 40 diagrammatically describes the preparation of expression plasmid pRH100 from pER103.

A 5.5 kb EcoRI restriction fragment of the lambda-clone Eq-alpha 16 (see FIG. 30), which weakly hybridized to a human alpha-IFN probe (examples D, E), was subcloned into the EcoRI site of plasmid pUC8. *E. coli* JM101 was transformed with the ligation mixture. A plasmid obtained, containing the correct insert was named pRH62. The EcoRI insert of the plasmid pRH62 was isolated from an agarose gel and subcloned into M13mp8 using the shotgun-method described in example G. The phage plaques obtained after transformation of *E. coli* JM101 were transfered onto nitrocellulose membranes by the method of Benton and Davis (19) (see example D). The 1.0 kb HindIII fragment of plasmid pRH61, containing the entire coding region of EqIFN-omega1 was used as hybridization probe. Recombinant M13 phages producing a hybridization signal were chosen for isolation of single-stranded DNA and sequencing by the method of Sanger. The determined DNA sequence (FIGS. 31A–31B) contains the entire coding region of a functionally equine interferon gene. It was named EqIFN-omega2, due to the homology to the equine interferon of plasmid pRH61 (example J, FIGS. 32A–32D) and the HuIFN-omega1 (23 amino acids leader peptide in front of the mature interferon with 172 amino acids). EqIFN-omega2 surprisingly contains a fifth cysteine residue at position 86 of the mature protein. The homology between the two equine omega-interferons is very high starting at amino acid 29 of the mature protein. The four cysteine residues as well as the potentially N-glycosylation site at positions 78–80 (Asn-Thr-Thr) are completely conserved (FIGS. 31A–31B and 32A–32D). The amino acid homology to the interferons of the omega-class of cattle and man is higher (61–70%) than to the equine alpha-interferons (57–60%, FIGS. 33A–33B).

14) Subcloning and sequencing of two more equine alpha-interferon genes (EqIFN-alpha 3, EqIFN-alpha 4)

A 3.2 kb HindIII restriction fragment of lambda-clone Eq-alpha 24, which hybridized to a human alpha-IFN probe (examples D, E), was subcloned into the HindIII site of plasmid pUC8. A plasmid with the correct insert, obtained after transformation of *E. coli* JM101 was named pRH83. In the same manner a 2.8 kb HindIII restriction fragment of lambda-clone Eq-alpha 9 was cloned into pUC8 and the obtained recombinant plasmid was named pRH82. The HindIII inserts of these plasmids were subcloned into M13mp8 using the shotgun method described above. The phages obtained after transformation of *E. coli* JM101 were hybridized using the method of Benton and Davis. Phages hybridizing to the 1.0 kb HindIII-BamHI fragment of plasmid pAH52/2 (example G), which contains the coding sequence for mature EqIFN-alpha 1, were used for isolation of single-stranded DNA and sequence analysis by the method of Sanger. The DNA sequences shown in FIGS. 34A–34B and 35A–35B revealed that these fragments contain functionally equine alpha-interferon genes, which were named EqIFN-alpha 3 (from pRH83) and EqIFN-alpha 4 (from pRH82). The genes code for polypeptides consisting of a signal peptide of 23 amino acids and a mature protein of 161 amino acids length. There is a remarkable high degree of homology between the DNA sequences of EqIFN-alpha 1 (pAH50) and EqIFN-alpha 3 (pRH83), and EqIFN-alpha 2 (pRH62) and EqIFN-alpha 4 (pRH82), respectively. The amino acid sequences of the mature proteins of EqIFN-alpha 1 and EqIFN-alpha 3 are identical. Due to the degeneracy of the genetic code, in this case the changes in the nucleotide sequences do not lead to a change in the amino acid sequence. EqIFN-alpha 3 right be an allelic variant of EqIFN-alpha 1.

REFERENCES (1) D. W. Leung, D. J. Catpon, D. V. Goeddel The structure and bacterial expression of three distinct bovine interferon-beta genes. Gene cloning transmission and expression in *Escherichia coli* Bio/Technology (1984) 2.5.458–464

(2) Q. J. Capon, D. V. Goeddel, GENENTECH Tierische Interferone Offenlegungsschrift DE 33 08 030 A1, Jul. 3, 1983

(3) A. M. Frischauf, H. Lehrach, A. Poustka, N. Murray Lambda replacement vectors carrying polylinker sequences J. Mol. Biol., (1983),173,827–842

(4) H. R. Rackwitz, G. Zehetner, A. M. Frischauf, H. Lehrach A protocoll for rapid restriction mapping of sequences cloned into lambda vectors Gene (1984). 30. 195–200

(5) D. Skup et al. Molecular cloning of partial cDNA copies of two distinct mouse IFN beta-mRNs Nucl. Acids Res; (1982),10, 10, 3069–3084

(6) Y. Higashi et al. Structure and expression of a cloned cDNA for Mouse Interferon-beta J. Biol. Chem. (1983), 258, 9522–9529

(7) V. Wilson, A. J. Jeffreys, P. A. Barrie, P. G. Boseley, P. M. Slocombe, A. Easton, D. C. Burke A comparison of vertebrate interferon gene families detected by hybridization with human interferon DNA J. Mol. Biol. (1963) 166, 457–475

(8) S. C. Tsai, M. J. Appel Hyporesponsiveness to dog interferon induction in vitro J. gen. Virol. (1983), 64, 2007–2012

(9) R. Dijkema, F. Pouwels, A. de Reus, H. Schellekens Structure and expression in *Escherichia coli* of a rat interferon-alpha gene Nucl. Acids Res., (1984), 12, 2, 1227–1242

(10) G. D. Shaw, W. Boll, H. Taira, N. Mantei, P. Lengyel, C. Weissmann Structure and expression of cloned murine IFN-Alpha genes Nucl. Acids Res., (1983), 11, 3, 555–573

(11) H. Bielefeldt Ohmann, L. A. Babiuk Effect of bovine recombinant alpha-1 interferon on inflammatory responses of bovine phagocytes J. Interferon Res., (1984), 4, 2, 249–263

(12) H. Bielefeldt Ohmann, J. E. Gilchrist, L. A. Babiuk Effect of recombinant DNA-produced bovine interferon alpha (BoIFN-_1) on the interaction between bovine alveolar macrophage and bovine Herpesvirus type 1 J. gen. Virol., (1984), 65, 1487–1495

(13) Y. Higashi, Y. Sokawa, Y. Watanabe, Y. Kawade, S. Ohno, C. Takaoka, T. Taniguchi Structure and expression of a cloned cDNA for mouse interferon-beta J. biol. Chem., (1983), 258 , 15, 9522–9529

(14) E. Dworkin-Rastl, P. Swetly, M. B. Dworkin Construction of expression plasmids producing high levels of human leukocyte-type interteron in *Escherichia coli* Gene, (1983), 237–248

(15) E. Dworkin-Rastl, M. B. Dworkin, P. Swetly Molecular cloning of human alpha and beta interferon genes from Namalwa cells J. Interferon Res., (1982), 2, 4, 575–585

(16) D. V. Goeddel, D. W. Leurg, T. J. Dull, M. Gross, R. M. Lawn, R. McCandliss, P. H. Seeburg, A. Ullrich, E. Yelverton, P. W. Gray The structure of eight distinct cloned human leukocyte interferon cDNAs Nature, (1981), 290, 20–26

(17) E. M. Southern Detection of specific sequences among DNA fragments separated by gel electrophoreses J. Mol. Biol., (1975), 93, 503-

(18) Blin, N. and Stafford, D. W. A general method for Isolation of high molecular weight DNA from eukaryotes Nucl. Acids Res. (1976), 3, 2303–2308

(19) W. D. Benton, R. W. Davies Screening lambda gt recombinant clones by hybridization to single plaques in situ Science, (1977), 196, 180–182

(20) Miller (1972) Experiments in Molecular Genetics, Cold Spring Harbor Laboratory, Cold Spring Harbor, N.Y.

(21) W. E. Stewart II (1979) The Interferon System, Springer-Verlag, N.Y.

(22) J. Messing et al. Gene. (1982), 19, 269–276

(23) F. Sanger, S. Nicklen, A. R Coulson DNA Sequencing with chain-terminating inhibitors Proc. Natl. Acad. Sci. USA. (1977), 74, 5463–5467

(24) R. Staden Automation of the computer handling of gel reading data produced by the shotgun method of DNA sequencing Nucl. Acids Res., (1982), 10, 4731–4751

(25) T. Maniatis, E. F. Fritsch, J. Sambrook Molecular Cloning, Cold Spring Harbor, N.Y.

(26) Birnboim and Doly Nual. Acids Res., (1979), 7, 1513

(27) Scalenghe, F., Turco, E., Edström, J. E., Pirotta, V. and Melli, M. Microdissection and cloning of DNA from a specific region of Drosophila melanogaster polytene chromosomes Chromosoma (1981), 82, 205–216

(28) K. Todokoro, D. Kioussis, C. Weissmann Two nonallelic human interferon alpha genes with identical codin regions EMBO J., (1984), 3, 8, 1809–1812

(29) B. Hohn, K. Murray Packaging recombinant DNA molekules into bacteriophage particles in vitro Proc. Natl. Acad. Sci. USA. (1977), 74, 3259–3263

(30) Hohn, B. In vitro packaging of lambda and cosmid DNA Meth.Enzymology (1979), 68, 299–309

(31) J. M. Messing, R. Crea, P. H. Seeburg A system for shotgun sequencing Nucl. Acids Res., (1981), 9, 309–321

(32) Tovey, M. G., Bandu, M. T., Begon-Lours, J., Brouty-Boye, D. and Gresser, I. Antiviral activity of bovine Interferons on primate cells J. Gen. Virol. (1977), 36, 341–344

(33) Hauptmann, R. and Swetly, P. A novel class of human type I interferons Nucl Acids Res. (1985), 13, in press

(34) Capon, D. J., Shepard, H. M. and Goeddel, D. V. Two distinct families of human and bovine interferon-alpha genes are coordinately expressed and encode functional poly-peptides Mol. Cell. Biol. (1985), 5, 768–779

(35) Feinstein, S. L, Mory, Y., Chernajovsky, Y., Maroteaux, L., Nir, U., Lavie, V. and Revel, M. Family of human alpha-interferon-like sequences Mol. Cell. Biol. (1985), 5, 510–517

(36) Twigg, A. J. and Sherratt, D. J. Trans-complementable copy-number mutants of plasmid ColE1 Nature (1980), 283, 216–218

(37) Sancar, A., Hack, A. M. and Rupp, W. D. Simple method for identification of plasmid-coded proteins J. Bacteriol. (1979), 137, 692–693

(38) Velan, B., Cohen, S., Grosfeld, H., Leitner, M. and Shafferman, A. Bovine Interferon alpha genes. Structure and expression J. Biol. Chem. (1985), 260, 5498–5504

(39) Zwarthoff, E. C., Mooren, T. A. and Trapman, J. Organization, structure and expression of murine Interferon alpha genes Nucl. Acids Res. (1985), 13, 791–803

We claim:

1. A substantially pure DNA molecule comprising the nucleotide sequence of a molecule selected from the group consisting of:
   (a) a DNA molecule coding for a protein selected from the group consisting of:
      (i) the amino acid sequence of EqIFN-α1 as shown in FIGS. 4A–4C;
      (ii) the amino acid sequence of EqIFN-α2 as shown in FIGS. 10A–10B;
      (iv) the amino acid sequence of EqIFN-ω1 as shown in FIGS. 12A–12C;
      (v) the amino acid sequence of EqIFN-ω2 as shown in FIGS. 31A–31C; and
      (vi) the amino acid sequence of CaIFN-α1 as shown in FIGS. 25A–25C;
   (b) the complement of a DNA molecule hybridizing to one of the DNA molecules of paragraph (a) under conditions of stringency which select for greater than 85% homology and coding for an interferon protein found in a horse or a dog; and
   (c) a DNA molecule which is degenerate with any DNA molecule of paragraphs (a) or (b).

2. A DNA molecule according to claim 1, wherein said DNA molecule codes for a protein having the amino acid sequence of EqIFN-α1 as shown in FIGS. 4A–14C.

3. A DNA molecule according to claim 1, wherein said DNA molecule codes for a protein having the amino acid sequence of EqIFN-α2 as shown in FIGS. 10A–10B.

4. A DNA molecule according to claim 1, wherein said DNA molecule codes for a protein having the amino acid sequence of EqIFN-β as shown in FIGS. 8A–8C.

5. A DNA molecule according to claim 1, wherein said DNA molecule codes for a protein having the amino acid sequence of EqIFN-ω1 as shown in FIGS. 12A–12C.

6. A DNA molecule according to claim 1, wherein said DNA molecule codes for a protein having the amino acid sequence of EqIFN-ω2 as shown in FIGS. 31A–31C.

7. A DNA molecule according to claim 1, wherein said DNA molecule codes for a protein having the amino acid sequence of CaIFN-α1 as shown in FIGS. 25A–25C.

8. A DNA molecule according to claim 1, wherein said conditions of stringency select for greater than 90% homology.

9. A method for producing an EqIFN or CaIFN protein comprising:
   (a) preparing a DNA molecule according to claim 1;
   (b) transforming an appropriate host cell with said DNA molecule;
   (c) culturing said host cell under conditions suitable for the expression of the heterologous DNA; and
   (d) collecting said protein.

10. The method of claim 9, wherein said DNA molecule codes for a protein having the amino acid sequence of EqIFN-α1 as shown in FIGS. 4A–4C.

11. The method of claim 9, wherein said DNA molecule codes for a protein having the amino acid sequence of EqIFN-α2 as shown in FIGS. 10A–10B.

12. The method of claim 9, wherein said DNA molecule codes for a protein having the amino acid sequence of EqIFN-β as shown in FIGS. 8A–8C.

13. The method of claim 9, wherein said DNA molecule codes for a protein having the amino acid sequence of EqIFN-ω1 as shown in FIGS. 12A–12C.

14. The method of claim 9, wherein said DNA molecule codes for a protein having the amino acid sequence of EqIFN-ω2 as shown in FIGS. 31A–31C.

15. The method of claim 9, wherein said DNA molecule codes for a protein having the amino acid sequence of CaIFN-α1 as shown in FIGS. 25A–25C.

16. The method of claim 9, wherein said DNA molecule is a plasmid selected from the group consisting of pAH50; pAH62; pRH63; pRH61; pAH60; pAH2; and pAH4.

17. A recombinant DNA molecule which is a plasmid selected from the group consisting of pAH50; pAH62; pRH63; pRH61; pAH60; pAH2; and pAH4.

18. A substantially pure DNA molecule comprising
   (a) a DNA sequence encoding an interferon protein found in a horse or a dog, wherein a DNA molecule having the complement of said sequence hybridizes under conditions of stringency selecting for at least 85% homology to the DNA insert of any one of the plasmids of claim 8, or
   (b) the complement of the sequence of paragraph (a).

19. A DNA molecule according to claim 18, wherein said conditions of stringency select for at least 90% homology.

20. A host cell transformed with a recombinant DNA molecule, said recombinant DNA molecule comprising the nucleotide sequence of a DNA molecule selected from the group consisting of:
   (a) a DNA molecule coding for a protein selected from the group consisting of:
      (i) the amino acid sequence of EqIFN-α1 as shown in FIGS. 4A–4C;
      (ii) the amino acid sequence of EqIFN-α2 as shown in FIGS. 10A–10B;
      (iii) the amino acid sequence of EqIFN-β as shown in FIGS. 8A–8C;
      (iv) the amino acid sequence of EqIFN-ω1 as shown in FIGS. 12A–12C;
      (v) the amino acid sequence of EqIFN-ω2 as shown in FIGS. 31A–31C; and
      (vi) the amino acid sequence of CaIFN-α1 as shown in FIGS. 25A–25C;
   (b) the complement of a DNA molecule hybridizing to one of the DNA molecules of paragraph (a) under conditions of stringency which select for greater than 85% homology and coding for an interferon protein found in a horse or a dog; and
   (c) a DNA molecule which is degenerate with any DNA molecule of paragraphs (a) or (b).

21. A host cell according to claim 20, wherein said DNA molecule codes for a protein having the amino acid sequence of EqIFN-α1 as shown in FIGS. 4A–4C.

22. A host cell according to claim 20, wherein said DNA molecule codes for a protein having the amino acid sequence of EqIFN-α2 as shown in FIGS. 10A–10B.

23. A host cell according to claim 20, wherein said DNA molecule codes for a protein having the amino acid sequence of EqIFN-β as shown in FIGS. 8A–8C.

24. A host cell according to claim 20, wherein said DNA molecule codes for a protein having the amino acid sequence of EqIFN-ω1 as shown in FIGS. 12A–12C.

25. A host cell according to claim 20, wherein said DNA molecule codes for a protein having the amino acid sequence of EqIFN-ω2 as shown in FIGS. 31A–31C.

26. A host cell according to claim 20, wherein said DNA molecule codes for a protein having the amino acid sequence of CaIFN-α1 as shown in FIGS. 25A–25C.

27. A host cell according to claim 20, wherein said conditions of stringency select for at least 90% homology.

28. A host cell according to claim 20, wherein said host is selected from the group consisting of prokaryotes, eukaryotes, and mammalian cells.

29. A host according to claim 28, wherein said host is a prokaryote selected from the group consisting of *E. coli*, *Bacillus subtilis*, *Salmonella typhimurium* and *Serratia marcescens*.

30. A host according to claim 28, wherein said host is a eukaryote selected from the genus Saccharomyces.

31. A host cell transformed with a recombinant DNA molecule, said recombinant DNA molecule comprising a plasmid selected from the group consisting of pAH50, pAH62, pRH63, pRH61, pAH60, pAH2 and pAH4.

* * * * *